US008038616B2

(12) United States Patent
Angelsen et al.

(10) Patent No.: US 8,038,616 B2
(45) Date of Patent: Oct. 18, 2011

(54) ACOUSTIC IMAGING BY NONLINEAR LOW FREQUENCY MANIPULATION OF HIGH FREQUENCY SCATTERING AND PROPAGATION PROPERTIES

(75) Inventors: Bjørn A. J. Angelsen, Trondheim (NO); Rune Hansen, Stadsbygd (NO); Øyvind Krovel-Velle Standal, Trondheim (NO)

(73) Assignee: SURF Technology AS, Trondheim (NO)

( * ) Notice: Subject to any disclaimer, the term of this patent is extended or adjusted under 35 U.S.C. 154(b) by 1400 days.

(21) Appl. No.: 11/204,492

(22) Filed: Aug. 16, 2005

(65) Prior Publication Data

US 2006/0052699 A1 Mar. 9, 2006

Related U.S. Application Data

(63) Continuation-in-part of application No. 11/189,350, filed on Jul. 25, 2005, now abandoned, which is a continuation-in-part of application No. 10/864,992, filed on Jun. 10, 2004, now Pat. No. 7,641,613, which is a continuation of application No. 10/851,820, filed on May 21, 2004, now abandoned.

(60) Provisional application No. 60/475,222, filed on May 30, 2003, provisional application No. 60/590,444, filed on Jul. 23, 2004.

(51) Int. Cl.
*A61B 8/00* (2006.01)
*G01N 29/22* (2006.01)

(52) U.S. Cl. .......................................... 600/437; 73/586

(58) Field of Classification Search .................. 600/437, 600/458, 448, 440–447, 453–457; 73/599, 73/602, 625, 626; 367/7, 11, 130, 138, 140; 702/2, 10, 16, 17; 22/68; 601/2; 310/311
See application file for complete search history.

(56) References Cited

U.S. PATENT DOCUMENTS 4,081,783 A 3/1978 Honda et al.
(Continued)

FOREIGN PATENT DOCUMENTS

EP 0 279 314 8/1988
(Continued)

OTHER PUBLICATIONS

XP 000621081 Fukukita et al. "Ultrasound pulse reflection mode measurement of nonlinearity parameter B/A and attenuation coefficient" pp. 2775-2782, Nov. 7, 1996.

(Continued)

*Primary Examiner* — Unsu Jung
*Assistant Examiner* — Lawrence N Laryea
(74) *Attorney, Agent, or Firm* — Cohen Pontani Lieberman & Pavane LLP

(57) ABSTRACT

Methods of acoustic imaging provide images with reduced reverberation noise and images of nonlinear scattering and propagation parameters of the object, and estimation methods of corrections for wave front aberrations produced by spatial variations in the acoustic propagation velocity. The methods are based on processing of the received signal from transmitted dual frequency band acoustic pulse complexes with overlapping high and low frequency pulses. The high frequency pulse is used for the image reconstruction and the low frequency pulse is used to manipulate the nonlinear scattering and/or propagation properties of the high frequency pulse. Through filtering in the pulse number coordinate and corrections for nonlinear propagation delays and optionally also amplitudes, a linear back scattering signal with suppressed pulse reverberation noise, a nonlinear back scattering signal, and quantitative nonlinear forward propagation and scattering parameters are extracted.

93 Claims, 16 Drawing Sheets

U.S. PATENT DOCUMENTS 4,483,345 A 11/1984 Miwa
4,532,812 A 8/1985 Birchak et al.
4,610,255 A 9/1986 Shimura et al.
4,686,659 A 8/1987 Yamamoto et al.
4,844,082 A 7/1989 Fukukita et al.
4,936,308 A 6/1990 Fukukita et al.
5,928,151 A * 7/1999 Hossack et al. ............... 600/443
5,961,464 A * 10/1999 Poland .......................... 600/458
6,186,951 B1 2/2001 Lizzi et al.
6,226,228 B1 * 5/2001 Hossack et al. ............... 367/138
6,238,342 B1 5/2001 Feleppa et al.
6,312,383 B1 * 11/2001 Lizzi et al. ................... 600/437
6,401,539 B1 6/2002 Langdon et al.
6,423,007 B2 7/2002 Lizzi et al.
6,485,423 B2 * 11/2002 Angelsen et al. ............. 600/458
6,488,626 B1 12/2002 Lizzi et al.
6,494,839 B1 * 12/2002 Averkiou ...................... 600/443
6,514,204 B2 2/2003 Alam et al.
6,533,726 B1 3/2003 Lizzi et al.
6,676,599 B2 1/2004 Torp et al.
6,682,487 B1 1/2004 Savord
6,726,627 B1 4/2004 Lizzi et al.
6,789,018 B1 9/2004 Khan
6,846,290 B2 1/2005 Lizzi et al.
7,198,601 B2 4/2007 Kanda et al.
2002/0032382 A1 * 3/2002 Averkiou ...................... 600/447
2002/0040188 A1 * 4/2002 Averkiou ...................... 600/458
2002/0122352 A1 9/2002 Khan et al.
2002/0161300 A1 10/2002 Hoff et al.
2003/0073905 A1 4/2003 Bernardi
2003/0114758 A1 * 6/2003 Jensen et al. .................. 600/437
2004/0030251 A1 * 2/2004 Ebbini et al. .................. 600/443
2004/0236222 A1 * 11/2004 Mao et al. ..................... 600/458
2004/0267129 A1 12/2004 Angelsen et al.
2006/0058677 A1 3/2006 Okada et al.

FOREIGN PATENT DOCUMENTS

JP 3 110491 5/1991
RU 2 205 425 5/2003
WO WO 2006/009469 1/2006

OTHER PUBLICATIONS

XP 001205482 Nightingale et al. "Investigation of Real-Time Remote Palpation Imaging" pp. 113-119, Feb. 21, 2001.

XP 000032893 Flax et al. "Phase-Aberration Correction Using Signals From Point Reflections and Diffuse Scatterers: Basic Principles" pp. 758-767, Nov. 1988.

Notice of Allowance dated Nov. 30, 2009 issued in corresponding U.S. Appl. No. 10/864,992.

Office Action dated Apr. 30, 2009 issued in corresponding U.S. Appl. No. 10/864,992.

Office Action dated Sep. 3, 2008 issued in corresponding U.S. Appl. No. 10/864,992.

* cited by examiner

ACOUSTIC IMAGING BY NONLINEAR LOW FREQUENCY MANIPULATION OF HIGH FREQUENCY SCATTERING AND PROPAGATION PROPERTIES

CROSS REFERENCE TO RELATED APPLICATIONS

This application is a continuation-in-part of application Ser. No. 11/189,350, filed Jul. 25, 2005, which is a continuation-in-part of application Ser. No. 10/864,992, filed Jun. 10, 2004, which is a continuation of U.S. patent application Ser. No. 10/851,820, filed May 21, 2004, which claimed priority from U.S. Provisional Patent Application Ser. No. 60/475,222, filed May 30, 2003.

BACKGROUND OF THE INVENTION

1. Field of the Invention

This invention relates to methods and systems for imaging of spatial variation of acoustic parameters of an object and particularly gas bubbles and high density scatterers in the object. The methods have applications in a variety of fields with a variety of objects, for example ultrasound imaging of biological tissues and fluids, acoustic imaging of geologic structures, and detection of objects in water with SONAR.

2. Description of the Related Art

Acoustic imaging is used in a variety of applications, such as medical ultrasound imaging of internal organs, SONAR imaging of fish, sea animals and other objects in the sea, imaging of geologic structures for various purposes such as studies of archeological digs and surveillance of oil wells. A wide range of frequencies of the transmitted acoustic pulse are used for different applications, ranging from infrasound for imaging of some geological structures to ~100 MHz ultrasound imaging of some biological and microscopic structures. Despite this spread of applications and imaging frequencies the imaging methods are very similar for all applications. In this patent we therefore refer to these imaging methods in general as acoustic imaging, whereas a large part of the applications, especially medical applications, will use inaudible ultrasound frequencies from ~20 kHz to well into the ~100 MHz range. Where the imaging frequencies are in the ultrasound range, such as medical imaging, we also will use the term ultrasound imaging, not limiting the methods to ultrasound frequencies and medical applications only.

Despite the widespread use of acoustic imaging, current images are noisy, require large skills for the interpretation, and provide limited quantitative information about the objects. This provides problems for differentiation of object structures and estimating quantitative object properties. With SONAR imaging in water it is for example often difficult to differentiate objects close to or on the sea bed, like fish or other sea animals or mines, from the seabed echoes. Similarly, in geologic imaging it can be difficult to determine material compositions of the geologic structures. In medical applications it can be difficult to differentiate structures like a tumor or atherosclerotic tissue from normal tissue. Important reasons for this are described below.

Spatial variations in the linear acoustic properties of the object (mass density and compressibility) are the physical basis for acoustic imaging. However, with large variations of the acoustic properties in complex structures, the following effects will degrade the images:

i) Interfaces between materials with large differences in acoustic properties can give so strong reflections of the acoustic pulse that multiple reflections get large amplitudes. Such multiple reflections are termed pulse reverberations, and add a tail to the propagating acoustic pulse, which shows as noise in the acoustic image.

ii) Variations of the acoustic velocity within the complex object structures produce forward propagation aberrations of the acoustic wave-front, destroying the focusing of the beam main lobe and increasing the beam sidelobes.

The reduced focusing of the beam main lobe by the wave-front aberrations reduces the spatial resolution in the acoustic imaging system. The pulse reverberations and the increase in beam side lobes by the wave-front aberrations, introduce additive noise in the image, which reduces the ratio of the strongest to the weakest scatterer that can be detected in the neighborhood of each other, defined as the contrast resolution in the image. This noise is termed acoustic noise as it is produced by the transmitted acoustic pulse itself. Increasing the transmitted pulse power will hence not improve the power ratio of the signal to the noise of this type, contrary to what is found with electronic receiver noise.

In echocardiography for example, pulse reverberation noise can obscure images of the apical region of the heart, making it difficult to detect apical thrombi, and reduced contraction of the apical myocardium. Further by example, in carotid imaging reverberation noise can obscure detection and delineation of a carotid plaque. Similar to these examples, the pulse reverberation noise limits the detection of weak targets and differentiation of small differences in image contrast in all aspects of acoustic imaging.

$2^{nd}$ harmonic imaging is a method to reduce the image degrading effect of the pulse reverberations in structures close to the acoustic source like the human body wall, because the $2^{nd}$ harmonic content in the pulse accumulates as a function of depth and is hence very low as the pulse passes the near source structures like the body wall. However, the sensitivity with $2^{nd}$ harmonic imaging is less (~–20 dB) than with $1^{st}$ harmonic imaging, which limits maximal image depth, particularly in dense objects like geologic structures and biological objects like the liver, kidneys, breast, etc, and for blood velocity imaging. For real time 3D imaging one wants a broad transmit beam that is covered with many parallel receive beams to increase volume image rate. Such broad $2^{nd}$ harmonic transmit beams are difficult to obtain due to reduced $1^{st}$ harmonic amplitude in broad beams, which produces problems for $2^{nd}$ harmonic imaging with multiple parallel receive beams used in real time 3D imaging. This is especially true for sparse acoustic arrays where the number of elements that generates the transmit beam is limited.

In medical applications, tissue diseases like tumors and atherosclerosis of an artery wall, affect the acoustic parameters of the tissue, such as the shear modulus, the bulk compressibility, and the acoustic absorption. The variations of these properties are mainly produced by in-growth of foam cells, fat, or connective tissue fiber molecules, but also through segregation of calcium in the tissue. The in-growth of connective tissue increases the acoustic absorption and the shear modulus, the latter producing an increased stiffness to palpation that can be observed by touching the tissue. Much work has been done on estimation of the shear modulus by using ultrasound bulk waves to register the displacement of shear waves in the tissue in methods often referred to as elastography, also referred to as remote ultrasound palpation. However, to date these methods have found limited clinical application, and there is still a great need for improved differentiation of such tissue changes with ultrasound.

In breast tumors, segregated micro-calcifications are today detected with X-Ray mammography, as an indication of a malignant tumor. These micro-calcifications are so small that the scattered ultrasound signal from them is buried in the signal from surrounding tissue, and they are not detected with current ultrasound imaging. Hence, it is a need to improve ultrasound imaging to also detect such micro-calcifications. Micro-calcifications in atherosclerotic plaque also give information about the stability of the plaque and improved imaging of these micro-calcifications are needed.

Several diseases also affect the blood perfusion through the tissue, for example through angiogenesis or necrosis of the micro-vasculature in malignant tumors, or reduced blood flow due to vascular stenosis or thrombosis both in the coronary arteries of the heart and in peripheral vessels. The blood velocities in the micro-vasculature and small vessels are so small that they cannot be detected with ordinary, non-invasive ultrasound Doppler techniques. Ultrasound contrast agents in the form of solutions of small micro-bubbles (diam ~3 μm) have therefore been developed to improve ultrasound imaging of the micro-vasculature and also to estimate the blood perfusion through the tissue. The micro-bubbles are injected into the blood stream and provide highly increased and nonlinear scattering of the ultrasound from the blood. They hence highly increase the nonlinear scattering from the tissue that contains such micro-bubbles, where in special cases single micro-bubbles can be visualized in dense tissues and provides a potential for molecular ultrasound imaging with tissue specific targeted contrast bubbles. Such micro-bubbles can also provide useful image enhancement when injected into other body fluids, for example the insterstitial fluid to trace lymphatic drainage to sentinel lymph nodes, or in the urinary system for targeted attachment of bubbles to tumor tissue, or other. During decompression in diving and space activities, micro gas bubbles often form spontaneously in the tissue causing decompression sickness, and it is a need for early detection of such gas bubbles to improve decompression profiles and avoid decompression sickness in personnel under such operations, and even to monitor formation of such bubbles as an early warning during activity.

During production in an oil well, one for example wants to monitor changes in the geological structures around the oil wells, for example to monitor the amounts of oil or gas in the sand stone, observe the boundary between gas/oil and water, and observe any structural slides in the neighborhood of the well. The acoustic properties of the structures, and particularly the nonlinear component of the acoustic properties, are influenced by the amount of gas, oil, or water in the porous rock. Acoustic imaging of the structures surrounding the oil well can be done from acoustic transducers in the oil well. Utilizing imaging methods that provide quantitative acoustic data from the object hence allows detections of the amount of gas, oil, or water in the structures surrounding the oil well.

In detection of fish or sea animals or other objects close to the seabed it is often difficult to differentiate between the echoes from the seabed and the object, particularly with side looking beams. The swimming fish or sea animals has a gas filled bladder or lungs that has quite different and nonlinear acoustic properties compared to those of the seabed. These differences in acoustic properties can with methods according to the current invention be used to differentiate overlapping echoes from such objects and the seabed. The methods can also be used to enhance small solid structures, like a mine, on a softer seabed or in soil, similar to detection of micro-calcifications in a tumor.

There is hence a great need for improved acoustic imaging that reduces the image noise, and enhances the image contrast for variations in object properties, Methods according to the current invention reduce the image noise, and enhance the image contrast for variations in object properties by transmitting dual frequency band acoustic pulse complexes composed of overlapping high and low frequency pulses into the object. Dual frequency band ultrasound pulses have previously been used in medical ultrasound imaging for various purposes, where in M-mode and Doppler [Br Heart J. 1984 January; 51(1):61-9] simultaneous transmission was used of a 3 MHz pulse and a 1.5 MHz pulse with fixed phase relation between the pulses, for optimal M-mode imaging of the heart (3 MHz pulse) and Doppler blood velocity measurements (1.5 MHz pulse) to interrogate cardiac defects. A concentric annular transducer arrangement was used, where the 3 MHz M-mode ultrasound pulse was transmitted and received by the central transducer disc, while the 1.5 MHz Doppler ultrasound pulse was transmitted and received by a surrounding annular element.

The use of dual band transmitted pulses is also described in U.S. Pat. No. 5,410,516, for improved detection of ultrasound contrast agent micro-bubbles. In this patent, simultaneous transmission of two ultrasound pulses with different center frequencies is described, where the scattered pulses from the micro-bubbles contain sums and differences of the transmitted frequencies produced by the nonlinear scattering from the micro-bubbles, and these sum and difference frequencies are used for the detection of the micro-bubbles.

A similar use of dual band pulses is described in U.S. Pat. No. 6,312,383 for detection of ultrasound contrast agent, where the phase between the two bands is changed between transmissions. This can be viewed as a special case of U.S. Pat. No. 5,410,516, where the change in phase of the low frequency pulse can be viewed as a beat between the low frequency and the pulse repetition frequency.

However, although both the last two patents use nonlinear scattering with dual band pulses for detection of contrast agent in tissue, the presented patents both fail to recognize the nonlinear effect of the low band pulse on the forward propagation velocity of the high band pulse, which in the practical situation will limit the suppression of the tissue signal in relation to the contrast agent signal. The patents also do not recognize how the nonlinear scattering from ordinary tissues or other objects can be retrieved. Accumulative nonlinear forward propagation effects will produce similar signal characteristics for the strong, linear scattering from the tissue, as for the local, nonlinear scattering from micro-bubbles and tissues. This effect will mask the local, nonlinear scattering from micro-bubbles and other object parts and limit the contrast to tissue signal power ratio (CTR). Presence of gas and micro-bubbles in a region also heavily increases the forward, accumulative, nonlinear propagation effect and makes the linear scattering from the object beyond such a region highly mask the scattering from gas and micro-bubbles in the object. This phenomenon for example highly affects imaging of contrast agent in myocardium with pulses that passes the ventricle with contrast agent before entering the myocardium, and can for example falsely indicate perfusion in an ischemic myocardium. It will also affect the differentiation between gas and oil past a region with gas in geologic structures.

The current invention differs from the prior art in that it utilizes the nonlinear effect on the propagation velocity for the high frequency pulse by the low frequency pulse, and an understanding of this effect, in the formation of image signals based on the high frequency propagated and scattered signals. This allows a separation of the accumulative nonlinear effect on the signals from the effect of the local nonlinear object parameters, hence allowing estimation of local nonlinear object parameters, which is not possible by prior art. The invention further devices a method for separation of the accumulative effect of acoustic absorption on the signals, enabling the estimation of the local acoustic absorption parameters of the object.

SUMMARY OF THE INVENTION

The methods have applications to acoustic imaging both with back-scatter signals, and computerized reconstruction imaging based on angular scattering and/or forward transmission measurements.

Dual band acoustic pulse complexes with pulse components both in a low and a high frequency band that overlaps in the time domain, are transmitted towards the region of the object to be imaged. The nonlinear manipulation of the object scattering and propagation properties for the high frequency pulse by the low frequency pulse is utilized in the process of forming image signals. The high frequency components of the received signals are processed to give the image parameters/signals, and the low frequency components in the received signals can be removed through filtering, for example directly in the receive transducer array.

The processing according to the invention is part of the complete processing necessary to form images, where additional processing that is necessary to form the final image but not disclosed in this invention, is part of the open knowledge. For backscatter imaging, the methods are used to form radial image lines where 2D and 3D images are obtained by lateral beam scanning according to known methods. The radial image lines can be the signal envelope for structural images, Doppler measurements of radial scatterer displacement and displacement velocities, radial displacement strain or displacement strain rates of relative scatterer movements, or fast time (depth time) spectral parameters for object characterization. Parallel transmit and/or receive beams can be used to obtain multiple radial image lines in parallel to speed up the frame rate. With computer tomographic (CT) image reconstruction the methods provide improved measurements for the reconstruction, with reduced pulse reverberation noise and nonlinear image parameters that provide complementary information.

The invention devices several methods for improved imaging with increasing number of pulses required to form an image, with a complementary reduction in image frame rate, but with increasing image quality. The invention therefore further devices an instrument for operation of two or more of the methods and procedures for optimal selection of the methods for best performance of the instrument under given constraints, such as frame rate, image quality, a combination of frame rate and image quality, etc.

In a $1^{st}$ method according to the invention, the high frequency pulse propagates on a negative spatial gradient of the low frequency pulse oscillation, so that the back of the high frequency pulse gets a higher propagation velocity than the front of the pulse, due to the nonlinear effect on the propagation velocity by the low frequency pulse. This produces a cumulative spatial compression of the high frequency pulse as it propagates into the object, increasing the frequency and the bandwidth (i.e. shortens the length) of the high frequency pulse, in addition to the nonlinear self-distortion of the high frequency pulse producing harmonic components in the pulse. This increase in frequency given by the pulse length reduction, is counteracting the lowering of the pulse center frequency by the frequency dependent absorption in the object, hence providing a higher received center frequency than when this method is not utilized.

As the amplitude of the low frequency pulse is greatly reduced in the first reflection, multiple scattered pulses will not have this same length compression from the nonlinear effect on the propagation velocity for the high frequency pulse by the low frequency pulse, and will due to absorption drop to lower frequencies than first order scattered pulses with the same propagation lag, and can hence be filtered away producing a markedly suppression of the pulse reverberation (multiple scattering) noise, similar to $2^{nd}$ harmonic imaging but with $1^{st}$ harmonic sensitivity allowing deeper imaging and the use of higher acoustic imaging frequencies than with $2^{nd}$ harmonic imaging, improving spatial resolution. It is also simpler to obtain broader transmit beams allowing the use of more parallel receive beams, compared to $2^{nd}$ harmonic imaging, allowing higher image frame rates for 2D and especially 3D imaging. This is especially true when sparse arrays are used for the transmit beam, where it is difficult to obtain high enough amplitudes for adequate harmonic pulse self-distortion due to the limited number of array elements. The nonlinear pulse compression is also interesting when the $2^{nd}$ harmonic band of the received signal is used for imaging, as the frequency down-sliding of absorption is counteracted, providing higher frequencies and shorter pulses at deep ranges with improved resolution. The invention also devices this type of pulse compression for observation pulses of object displacement from radiation force push pulses, for frequency separation between the observation and the push pulses. The invention also devices placement of the high frequency pulse close to a peak in the low frequency pulse of a transmitted pulse complex, to allow for higher transmitted amplitude of the high frequency pulse with limitations in the Mechanical Index (MI) in the object.

In a $2^{nd}$ method according to the invention one transmits two or more dual band pulse complexes in sequence for each radial image line, where the high frequency pulse is found close to the peak or trough of the low frequency pulse, and where the frequency and/or phase and/or amplitude of the low frequency pulse vary for each transmission, to nonlinearly manipulate the acoustic scattering and forward propagation properties of the object for the high frequency components. The nonlinear manipulation of the forward propagation velocity is also with this method utilized in the process of forming image signals.

One can for example with this method also form a $1^{st}$ image signal, Eq. (14), with highly suppressed pulse reverberation noise with $1^{st}$ harmonic sensitivity, to be utilized with the same advantages as for the single pulse described above. The invention further devices to estimate the nonlinear propagation delays, which provides a $1^{st}$ quantitative nonlinear image parameter, Eq. (27), which is a quantitative nonlinear forward propagation parameter, as a combination of the differential of the estimated nonlinear propagation delays and an estimate of the amplitude of the low frequency pulse. The frequency of this pulse can be chosen so low (typically ~1/5-1/20 of the high, imaging frequency) that differences in acoustic power absorption between different objects and individuals can be neglected, and the low frequency pulse amplitude can be estimated from simulations or measurements in water or oil mixtures. The invention further devices a method of estimation of the local absorption coefficient through a combination of the estimated nonlinear propagation delays according to the $2^{nd}$ method (and also according to the $3^{rd}$ and $4^{th}$ method described below), and the radial gradient of the nonlinear propagation delay, and the center frequency in the high frequency received signal under the $1^{st}$ method, and the radial gradient of said center frequency.

The reduced reverberation noise in the received signals according to the invention greatly helps the estimation of corrections for wave front aberrations, for example as described in U.S. Pat. No. 6,485,423, U.S. Pat. No. 6,905,465 and U.S. patent application Ser. No. 10/894,387, in conjunction with the current invention. The invention also gives an approximate estimate of delay corrections for the wave front aberrations, derived from the nonlinear propagation delays estimated for the signals from each element or sub-aperture signal further defined in the specification below.

The invention further devices to correct the received high frequency signals with the nonlinear propagation delay estimates in the process of forming image signals. One is then able to highly suppress the linearly scattered signal from the object in the process and provide a $2^{nd}$ image signal, Eq. (19, 28) which is the nonlinearly scattered signal that shows local, nonlinear properties of the object on a scale less than the high frequency wave length, whereas the nonlinear propagation parameters show nonlinear object properties on a scale larger than a couple of high frequency wave lengths. The nonlinear signal then provides image contrast to rapid changes in object structures with improved differentiation of the structures. The nonlinear scattering is specially high at interfaces between materials with large differences in compliance, such as at interfaces between soft biological tissue and stiffer tissue like connective or muscular tissue or solid materials like calcifications, or between low and high compliance object parts like fat or micro gas bubbles in biological tissues, gas in porous rock, and fish swim-bladder or sea animal lungs and surrounding water and tissue, hence improving the characterization of the object structures.

Gas bubbles are often found naturally in the object as for example a fish swim bladder or sea animal lung, gas bubbles in porous rock, micro bubbles formed spontaneously during decompression in tissue, or micro bubbles injected into the object as a contrast agent. The bubble compression dynamics with acoustic pressure waves is described by a differential equation, providing a resonant acoustic scattering with a frequency dependent phase lag between the incident and the scattered wave, contrary to scattering from solids or fluids where the frequency variation of this phase is practically negligible. The resonance frequency and hence this phase lag of the scattered signal for the high frequency pulse from a gas-bubble is also manipulated by the low frequency pulse, in addition to the amplitude of the signal, which allows extraction of most of the scattered power from the gas-bubbles with this $2^{nd}$ method (not only the harmonic components), and significantly increases the CNR (Contrast to Noise Ratio) relative to existing methods. With good estimation of the nonlinear propagation delay corrections and also amplitude corrections, the methods according to the invention will strongly suppress the linearly scattered signal from the object, and significantly increase the COR (Contrast to Object Ratio) relative to existing methods. Contrary to state-of-the-art contrast agent detection methods, like harmonic imaging, pulse inversion, or power Doppler, the methods according to the current invention can use higher acoustic frequencies relative to the resonance frequency of the bubble, with improved spatial resolution. One can also use lower pulse amplitudes (lower Mechanical Index (MI)), which avoids destruction of medical contrast agent bubbles. This is important for imaging of tissue-specific targeted micro-bubbles where a limited group of micro-bubbles adheres to selected tissues, for example tumor tissues, atherosclerotic plaque, thrombi, etc. where it is important to image the bubbles without destruction.

A cloud of micro-bubbles in biological tissue, fluids, or porous rock will have strong, nonlinear effect on the propagation velocity of a through-passing pulse, and in such cases it is especially important to provide corrections for the nonlinear propagation delays for good suppression of the linearly scattered object signal beyond the cloud of bubbles. With this delay correction, the invention provides a separation between the accumulated nonlinear forward propagation delay, and the local, nonlinear scattering, contrary to what is found with other methods like harmonic or pulse inversion imaging, and provides a great advantage for suppression of object image signal when imaging gas-bubbles past the cloud, for example in the distal myocardium in medical imaging, detection of gas past a gas region in geological imaging, or detection of fish or sea animals past a school of fish or sea animals. If no or limited corrections for the nonlinear propagation effects are done in these cases, the linearly scattered signal from objects in regions beyond gas bubbles will show similar properties as the scattering from the gas bubbles, hence masking the detection of gas bubbles in these regions. This can for example falsely indicate blood perfusion in an ischemic region of myocardium, gas in geological structures, and fish or other sea animals in the water.

Aside from the multiple medical use of imaging of ultrasound contrast agent micro-bubbles, imaging of micro-bubbles according to this method in decompression situations found in diving and space activities, can be used to monitor formation of such bubbles to study and develop decompression profiles, or as an early safety alarm against sickness during decompression.

In further processing according to this $2^{nd}$ method, the delay corrected high frequency signals are combined along the pulse number coordinate to provide a $3^{rd}$ image signal, Eq. (17,29), the linearly scattered signal. This linearly scattered signal has the same attenuation due to power absorption as the $2^{nd}$ image signal, the nonlinearly scattered signal. Through a combination of the nonlinearly and the linearly scattered signals and the estimate of the low frequency pulse amplitude presented above, the invention presents a $2^{nd}$ quantitative nonlinear image parameter, Eq. (30), which is a quantitative nonlinear scattering parameter. This $2^{nd}$ quantitative nonlinear parameter then represents the spatial fluctuations in the nonlinear object parameters on a scale~smaller than the high band wave length, while the $1^{st}$ quantitative nonlinear parameter, Eq. (27), reveal a spatial average of the nonlinear object parameters on a scale~larger than the high band wave length. The backscatter and the forward propagation hence reveal two different quantitative image parameters that can be visualized for increased information about the object characteristics. The quantitative nonlinear parameters hence improve differentiation of object structures, and also open for object characterization with the method, which is useful in diagnosing tumors and atherosclerotic plaque in medical applications, assessing gas, oil or water in geologic structures, and assessing amount and size of fish and sea animals in water. Calibration of the thermal variation of these quantitative parameters also opens for local temperature estimation with ultrasound, for example to be used for guidance of hyper- or hypo-thermal treatment of tumors in medicine. It further provides new methods of quantifying contrast agent volume in tissue, blood perfusion through the tissue, and relative volume of gas and oil in geological structures.

With non-moving, temporary stationary objects, one can for example transmit two pulses with different frequency and/or phase and/or amplitude of the low frequency components, and combine the scattered or transmitted signals from these pulses to suppress the pulse reverberations and estimate the nonlinear object parameters. When the object and acoustic probe move relative to each other, it is advantageous to transmit more than two pulses for each radial image line to adequately suppress the linearly scattered signal or suppress the pulse reverberation noise with multiple pulses. For example, one can transmit a set of K pulses, all with the same phase of the high frequency components, but with different frequencies and/or phases and/or amplitudes of the low frequency components for each pulse. The back-scattered signals from these pulses are combined in a pulse-to-pulse high pass filter that suppresses the pulse reverberations and lets through the 1st order scattered signal components. With estimations and corrections for the nonlinear propagation delays, and optionally also amplitude corrections, before the high pass filter, one can extract the local, nonlinearly scattered signal from the object or the scattered signal from gas bubbles, and quantitative nonlinear propagation and scattering parameters of the object.

In this 2nd method the pulse reverberation noise (and to a small degree the nonlinear signal components themselves), introduce errors in the estimates of the nonlinear propagation delays. These errors limit the suppression of the linearly scattered signal when estimating the nonlinearly scattered signal. To efficiently remove the effect of the pulse reverberation noise on the estimation of the nonlinear delay corrections, one can use the 2nd harmonic component of the scattered signals with the 2nd method according to the invention, or one can according to a 3rd method of the invention transmit at least three pulses with different frequencies and/or phases and/or amplitudes of the low frequency pulse, as described in relation to Eqs. (42-44). The 3rd method still has influence of the nonlinear scattering in the estimation of the nonlinear propagation delays. In a 4th method according to the invention described in relation to Eqs. (45-48) one transmits at least 4 pulses with 4 different levels of frequencies and/or phases and/or amplitudes of the low frequency pulse, enabling the estimation of the nonlinear propagation delays, the linearly scattered signal, and the nonlinearly scattered signal, with minimal interference between each other and from reverberation noise.

It is also possible to use the 2nd harmonic band (or any harmonic band) of received signal both for the image formation according to any of the 2nd, 3rd, and 4th methods, instead of the 1st harmonic band of the received signal as described above. The advantage is added suppression of the pulse reverberation noise both in the image signals, and in the estimation of the nonlinear propagation delay as described above. The disadvantage is less sensitivity at deeper ranges reducing the image depth for the same image frequency.

With electronic steering of the beam direction one would typically use the same beam direction and transmit focus for all the transmit pulses for each radial image line and depth range, where the received signals are combined to suppress the linearly scattered object signal for that image line. Typical filtering schemes that are used are FIR-type filters or filters with time variable impulse response like orthogonal decomposition using for example Legendre polynomials, with filtering along the pulse number coordinate for each depth.

With mechanical scanning of the beam direction, as with annular arrays or 3D imaging, one would typically transmit pulses with variations in the frequency and/or phase and/or amplitude of the low frequency pulse as the beam direction is swept continuously, feeding the signal for each depth to a high pass filter along the pulse number coordinate. The outputs of the high pass filters are then sampled for each depth and radial image line to estimate the signals and image parameters to be used for image reconstruction along that radial image line in the depth range.

The invention further presents basic designs of imaging instruments that operate according to the methods according to the invention. As the number of pulses per radial image line, together with image quality and information, increases with the order of the methods, the frame rate decreases with the order of the methods. In a most advanced version, the instrument can operate more than one of the methods with procedures for optimal selection of the methods for best performance of the imaging under given constraints. Typical constraints are a minimal frame rate, minimal requirements on image quality etc.

As a last point, the invention provides a design procedure of transducer arrays that minimize the nonlinear effect on the propagation delay of the high frequency pulse by the low frequency pulse. With low amplitudes (~50 kPa) of the low frequency pulse components, such transducer arrays can allow imaging of medical ultrasound contrast agents or decompression micro bubbles with a limited but still interesting suppression of the linearly scattered signal from the object, without correcting for the nonlinear propagation delays of the high frequency pulse produced by the low frequency pulse.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1A:
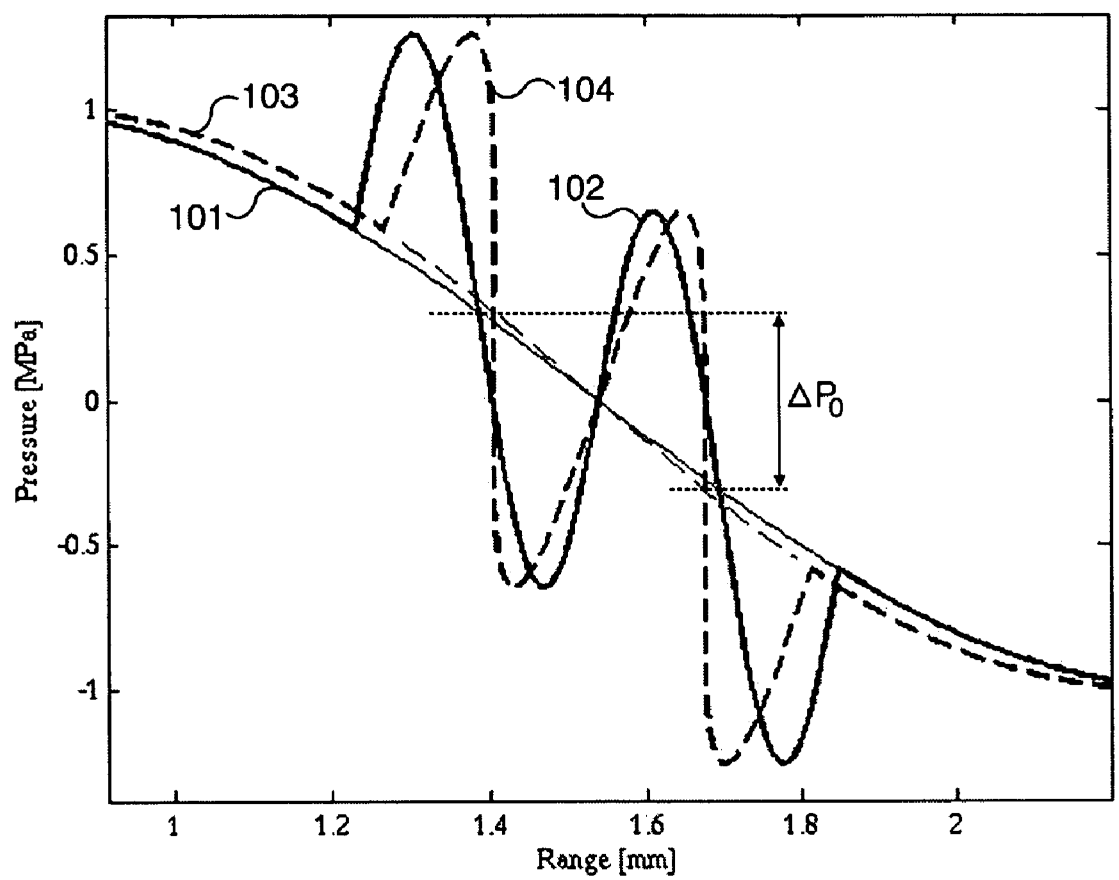
FIG. 1 illustrates a first type of transmit pulses according to the invention containing both a low and a high frequency pulse where the high frequency pulse is located at a spatial gradient of the low frequency pulse.

Acoustic bulk waves in homogeneous materials are in the linear regime governed by a linear wave equation where the bulk wave propagation velocity $c_0$ is determined by the mass density $\rho_0$ and the bulk compressibility $\kappa_0$ of the homogeneous propagation medium. The bulk compressibility is in the linear approximation of bulk elasticity defined through the relative volume compression of the material as $$\frac{\delta V}{\Delta V} = -\nabla\underline{\psi} = \kappa_0 p \tag{1}$$

where $\delta V$ is the relative volume compression of a small volume $\Delta V$ subject to the pressure p, and $\psi$ is the particle displacement in the material so that $-\nabla\underline{\psi}$ is the relative volume compression.

The scattering of acoustic bulk waves from objects is produced by spatial fluctuations in the compressibility and mass density of the object. We denote the spatially varying mass density and compressibility for low pressure amplitudes as $\rho_0(\underline{r})$ and $\kappa_0(\underline{r})$, where $\underline{r}$ is the spatial coordinate. The linear back-scattering coefficient from a local point $\underline{r}$ is then $$k^2\upsilon_0(\underline{r};\underline{e}_i\underline{e}_s) = k^2\left(\frac{\kappa_0(\underline{r}) - \kappa_{0a}(\underline{r})}{\kappa_{0a}(\underline{r})} + \frac{\rho_0(\underline{r}) - \rho_{0a}(\underline{r})}{\rho_0(\underline{r})}\underline{e}_i\underline{e}_s\right) \tag{2}$$

where $\rho_{0a}(\underline{r})$ and $\kappa_{0a}(\underline{r})$ are spatial averages of the mass density and bulk compressibility on a scale~a couple of wave lengths $\lambda$ of the acoustic pulse, and $\underline{e}_i$ is the unit vector in direction of the incoming wave, and $\underline{e}_s$ is unit vector in the direction one observes the scattered wave, as illustrated in FIG. 9. The scalar product $\underline{e}_i\underline{e}_s = \cos\gamma_{is}$ where $\gamma_{is}$ is the angle between the direction of the incoming wave and the scattering direction. For back-scattering $\gamma_{is}=\pi$ and $\underline{e}_i\underline{e}_s=-1$. The wave number of the incident wave is $k=\omega/c=2\pi/\lambda$ with $\omega$ as the angular frequency and c as the acoustic propagation velocity. The linearly back-scattered signal at $\underline{r}$ from a pressure wave with amplitude $p_1(\underline{r},\omega)$ at the angular frequency $\omega$ is then proportional to $k^2\upsilon_0(\underline{r})\,p_1(\underline{r},\omega)$. The imaging is typically done with a transmitted pulse with center frequency $\omega_1$ and bandwidth $B_1$ where the image signal is band pass filtered version of $k^2\upsilon_0(r)$ in the range (r) coordinate around $2k_1=2\omega_1/c$ and bandwidth $2B_1/c$. As a softer material (increased compressibility) usually has a lower density, the compressibility and mass terms in Eq. (2) usually have opposite signs so that for back scattering the magnitudes add constructively, where the compressibility term dominates the back-scattering by a factor ~2.5 over the mass density term.

The spatial variation in the average mass density and bulk compressibility, $\rho_{0a}(\underline{r})$ and $\kappa_{0a}(\underline{r})$, produces a spatial variation in the acoustic propagation velocity as $$c_{0a}(\underline{r}) = \frac{1}{\sqrt{\rho_{0a}(\underline{r})\kappa_{0a}(\underline{r})}} \tag{3}$$

This spatial variation of the propagation velocity is responsible for aberrations of the wave front, in biological imaging specially found in the body wall, but also throughout the whole of some objects, like the breast and glands that contain regions of fat or connective tissue. In geologic imaging large variations in the propagations velocity is often found throughout the whole object.

Typical values for soft tissues and fluids are $\kappa_0\sim 400\cdot10^{-12}$ $Pa^{-1}$ with a typical acoustic pulse amplitude of $p\sim10^6$ Pa, which gives $\delta V/\Delta V\sim 0.4\cdot10^{-3}$. A volume compression produces an increase in the mass density as $\delta\rho/\rho_0=\kappa_0 p\sim 0.4\cdot10^{-3}$. Rock shows lower compressibility, while water and oils shows similar compressibilities as tissues. Similarly, when the object is compressed, there is a decrease in the bulk compressibility which together with acoustic absorption in the object modifies Eq. (1) as [1]

$$\frac{\delta V}{\Delta V} = -\nabla\underline{\psi} = (1 - \beta_n\kappa_0 p)\kappa_0 p + h \underset{t}{\otimes} \kappa_0 p \tag{4}$$

where $\beta_n=(1+B/2A)\sim 5$ is a nonlinearity parameter related to the commonly defined parameters B and A for the nonlinear bulk modulus [1]. The temporal convolution between the pressure waveform and h represents the frequency dependent acoustic power absorption in the material. The first term describes a nonlinear bulk compressibility influenced by the pressure where a differentiation of this term a reference pressure $p_0$ gives $$\kappa = \frac{1}{\Delta V}\frac{\partial\Delta V}{\partial p} = (1 - 2\beta_n\kappa_0 p_0)\kappa_0 \tag{5}$$

which gives a relative variation of the compressibility with pressure as $\delta\kappa_n/\kappa_0=-2\beta_n\kappa_0 p_0$. The nonlinear variation in bulk compressibility is hence $2\beta_n\sim 10$ times higher than the nonlinear variation in mass density produced by the pressure, where for p~1 MPa we get $\delta\kappa_n/\kappa_0=-2\beta_n\kappa_0 p_0\sim 4\cdot10^{-3}$.

The nonlinear variation of the mass density and the compressibility produces a nonlinear modification of both the scattering and the forward propagation velocity of the wave, and the invention utilizes these effects to reduce pulse reverberation noise, increase image contrast for various object structures, micro-calcifications, and gas bubbles, and produce quantitative acoustic image parameters of the object, micro calcifications, gas bubbles and gas filled regions. In the following we describe example embodiments of the invention with reference to the Figures.

In a $1^{st}$ method according to the invention, we utilize time compression and expansion of the high frequency pulse by the low frequency pulse to manipulate the center frequency and the bandwidth of the forward propagating pulse within the object. This time compression is produced by the pressure dependency of the forward propagation velocity, which can be approximated as $$c_a = c_{0a}\sqrt{1 + 2\beta_{na}\kappa_{0a}p - 2\beta_{na}^2(\kappa_{0a}p)^2} \approx c_{0a}(1 + \beta_{na}\kappa_{0a}p) \tag{6}$$

where $\beta_{na}$ and $\kappa_{0a}$ are local, spatial average values over a couple of wavelengths at zero pressure as defined above. To further illustrate this principle, we refer to FIG. 1*a* which shows a transmitted pulse that is composed of a low frequency component 101 with amplitude $p_0$ and an added high frequency component 102 with amplitude $p_1$, where the high frequency component is riding on the negative spatial gradient of the low frequency pulse, centered around the zero of the low frequency pulse for the example. The high frequency pulse is used for the imaging, and in the receiver, the low frequency pulse is removed through filtering, for example in the receiver transducer itself, or as discussed below.

Figure 1B:
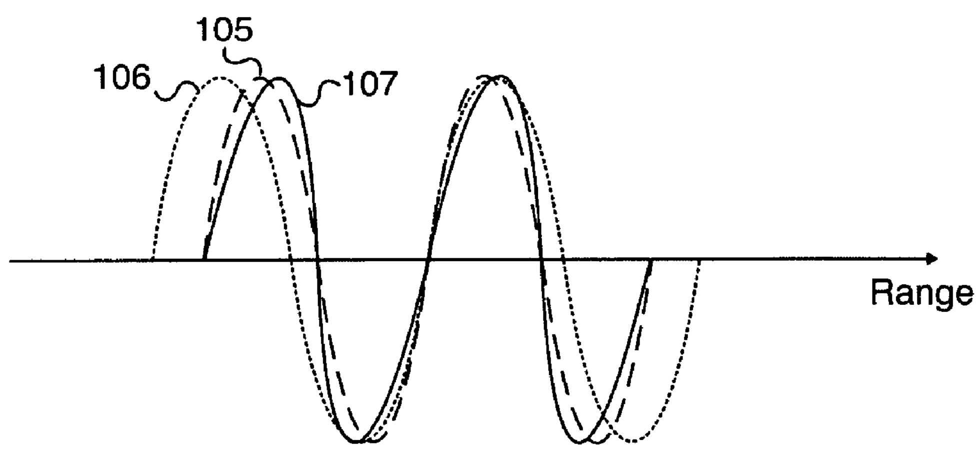

The pressure dependent propagation velocity produces an accumulatively increasing forward propagation distortion of the pulse determined by the actual pulse pressure, which is the sum of the low and the high frequency pulse pressures, which after a propagation distance r produces the distorted low frequency pulse 103 with the distorted high frequency pulse 104. The distortion of the high frequency pulse can be separated into a pulse length compression of the zero points of the high frequency pulse produced by the local low frequency pulse pressure, and a pulse shape self distortion produced by the instantaneous high frequency pressure itself. 105 in the FIG. 1*b* illustrates the time compression distorted pulse (dashed lines) where the undistorted high frequency pulse 106 is shown (dotted lines) for comparison, and the added pulse self distortion produces the fully distorted pulse 107. The pulse compression occurs since the higher low frequency pressure at the high frequency pulse tail gives a higher propagation velocity of the tail of the pulse, compared to the propagation velocity with the lower low frequency pressure at the head of the high frequency pulse. This pulse compression produces an increase in the center frequency and the bandwidth of the high frequency pulse, while the pulse shape distortion introduces harmonic components of the fundamental frequency band of the high frequency pulse, which both are utilized in this $1^{st}$ method according to the invention. The propagation distortion of the low frequency pulse produces harmonic components of the transmitted low frequency band.

This nonlinear forward propagation distortion of the pulse, is the same effect that produces harmonic components in the forward propagating pulse, that is linearly back scattered from the object, and is used in harmonic imaging of objects, further discussed in relation to Eqs. (10-14) and FIG. 9. The amplitude of the harmonic components in the pulse first increases with propagation distance, for later to decay with increasing propagation distance due to the acoustic power absorption of the high frequency pulse, and beam divergence. The low frequency band can be chosen so low (~1/5-1/20 of the high frequency) that the absorption of the low frequency pulse is practically negligible over actual image ranges. Reduction in the low frequency pulse amplitude is then mainly given by beam divergence, which can be limited by array design, and the nonlinear propagation effect of the low frequency pulse on the high frequency pulse can therefore by array design be made high throughout the whole image range, also with other situations according to the invention as for example shown in FIG. 3. This provides increased sensitivity at deep ranges with methods according to this invention, compared to $2^{nd}$ harmonic imaging, a phenomenon we return to in relation to Eq. (14) and FIG. 7*c*. In some situations it can be advantageous to use the $2^{nd}$ harmonic band of the received high frequency signals together with the methods according to this invention, for improved suppression of pulse reverberation noise in the images and in the estimation of image parameters, as discussed below.

To clarify the essential concepts, we first analyze a situation with no beam divergence (i.e. plane waves) and no ultrasound absorption. The pressure difference of the low frequency pulse across a wavelength $\lambda_1$ of the high frequency pulse is $\Delta p_0=\lambda_1 \partial p_0/\partial r$. This gradient produces a difference in propagation velocity over a high frequency wavelength of $\Delta c_a=-\beta_{na}\kappa_{0a}c_{0a}\Delta p_0$ which produces a compression of the wave with propagation distance r. We note that the same $\Delta c_a$ produces an increase with r in the low frequency pressure gradient proportional to the reduction in the high frequency wavelength, so that the pressure drop along the compressed high frequency wavelength is maintained as $\Delta p_0$ as illustrated in FIG. 1*a*. After a propagation time $t=r/c_{0a}$ we hence get a compression of the high frequency wave length of $\Delta\lambda_1=\Delta c_a t=r\Delta c_a/c_{0a}=-\beta_n\kappa_{0a}\Delta p_0 r$. With no absorption and beam divergence we get $\Delta p_0=\lambda_1\partial p_0/\partial r=p_{00}k_{00}\lambda_{10}=2\pi p_{00}\lambda_{10}/\lambda_{00}$, where $p_{00}$ is the amplitude, $k_{00}=2\pi/\lambda_{00}$ is the wave number, and $\lambda_{00}$ is the wavelength of the transmitted low frequency pulse at the array surface before propagation distortion. After a propagation time $t=r/c_{0a}$ we hence get a compression of the high frequency wave length of $\Delta\lambda_1=-\beta_n\kappa_{0a}\Delta p_0 r=-\beta_n\kappa_{0a}p_{00}k_{00}\lambda_{10}r$, which produces a compression increase in the high frequency of $$f_{1p}=\frac{\lambda_{10}}{\lambda_{10}+\Delta\lambda_1}f_{10}=\frac{1}{1-\beta_{na}\kappa_{0a}p_{00}k_{00}r}f_{10} \quad \text{a)} \tag{7}$$

$$\Delta f_{1p}=f_{1p}-f_{10}=\frac{\beta_{na}\kappa_{0a}p_{00}k_{00}r}{1-\beta_{na}\kappa_{0a}p_{00}k_{00}r}f_{10} \quad \text{b)}$$

The compression/expansion is accompanied by a proportional change in the pulse bandwidth (~inverse pulse length). According to these formulas, the frequency becomes infinite for $z_{sh}=1/\beta_{na}\kappa_{0a}p_{00}k_{00}$ which is a phenomenon called acoustic shock, where the negative gradient of the low frequency oscillation becomes infinite. In the practical situation acoustic power absorption prevents this situation.

The acoustic absorption also produces a down sliding of the high frequency pulse center frequency while preserving the pulse bandwidth. The compression increase in frequency is only found for the outgoing pulse where the amplitude of the low frequency pulse is sufficiently large, while the absorption down sliding is found both for the outgoing and scattered pulse, which for back scattering gives a propagation distance of 2r. For a Gaussian pulse envelope the down sliding in frequency is given as $$\Delta f_{1a}=-0.36\alpha B_1^2 r \tag{8}$$

where $B_1$ is the 6 dB bandwidth of the high frequency acoustic pulse, and $\alpha$=dBatt/8.686 (mmMHz)$^{-1}$ is the average, local frequency constant of the absorption coefficient with linear frequency dependency of the absorption. With dBatt=0.05 dB/mmMHz we get $\alpha=5.76\cdot10^{-3}$ (mmMHz)$^{-1}$. We should note that with transmission computed tomography imaging, which is discussed in relation to FIG. 9, we have only one-way propagation where the absorption down-sliding of the frequency is half of that in Eq. (8).

The typical imaging range, R, for backscatter imaging is limited by the acoustic absorption that increases linearly with frequency. The range R is therefore related to the high frequency acoustic wavelength $\lambda_1=c_{0a}/f_1$ as $R\sim200\lambda_1$-$300\lambda_1$. For $p_0$=1 MPa, $\beta_n=5$, $\kappa_{0a}=400\cdot10^{-12}$ Pa$^{-1}$, $R=250\lambda_1$ and $\lambda_{10}/\lambda_{00}=10$, we get $\Delta f_{1p}=0.458f_{10}$, which for $f_{10}$=10 MHz gives $\Delta f_{1p}$=4.58 MHz. The acoustic shock is found for $z_{sh}/\lambda_{10}=796$ which is 2.65 times the maximal image range. For $B_{10}$=5 MHz we get an absorption down sliding of the high center frequency according to Eq. (8) of $\Delta f_{1a}$=4 MHz, which balances the compression up-conversion of the frequency, so that the received frequency for the first order back scatter in the absorbing medium is approximately $f_{10}$=10 MHz for all depths, i.e. as transmitted.

As the pulse compression is produced by the low frequency pulse where as described above the power absorption can be neglected for actual imaging ranges, the pulse length compression with the corresponding increase in the bandwidth is practically independent of the absorption over actual imaging ranges. The absorption down sliding of the center frequency of the high frequency pulse, however, is produced by the absorption of the high frequency pulse. The frequency down sliding is proportional to the square of the absolute bandwidth $B_1$ of the pulse, and the absorption down-sliding preserves the bandwidth. Hence, the combined effect of the nonlinear pulse compression and the absorption down conversion in the above example is a pulse with approximately constant center frequency which maintains the lateral resolution (beam width), but with bandwidth (~inverse pulse length) that increases with depth which improves the range resolution with depth. Note from Eq. (8) that the increase in $B_1$ width depth produces accelerating absorption down-sliding with depth. We return to more detailed analysis of this situation in relation to Eqs. (35,36).

The forward propagation up-conversion of the high band pulse frequency can be used to improve image resolution at deeper ranges. It can also be used to increase penetration with better resolution at deep ranges where for example one transmits a fairly low frequency that is increased to a higher frequency at deeper ranges by the low frequency pulse, hence reducing the total absorption along pulse path for the obtained high band pulse frequency at the deep ranges. It can also in this aspect be utilized a sliding between the phase of the low and high frequency pulses with propagation distance, with special designs of the low frequency beam profile in relation to the high frequency beam profile as discussed in relation to FIG. 8 below. This sliding for example makes it possible that the high frequency pulse is found at the negative spatial gradient of the low frequency oscillation in the near/mid range to slide towards zero or even positive spatial gradient of the low frequency oscillation in the far range. This reduces the pulse compression to zero or even introduces a stretching of the high frequency pulse by the low frequency pulse at the deep ranges, which (also combined with absorption down sliding) reduces the center frequency and bandwidth of the high band pulse for the deep ranges with increased penetration.

Figure 2:
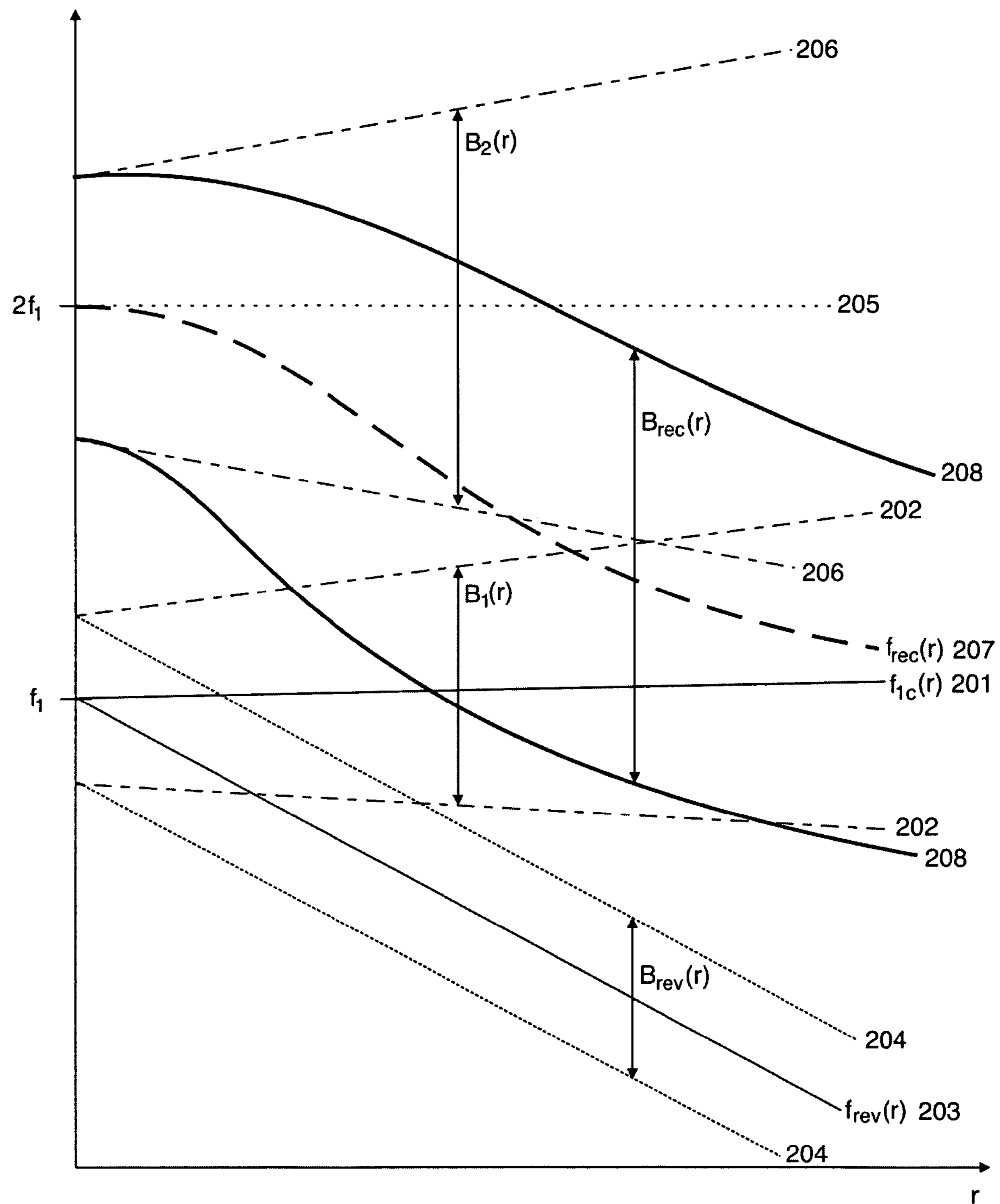
FIG. 2 shows how depth variable band pass filtering of the received signal from a pulse as in FIG. 1 can be used to highly suppress pulse reverberation noise.

The amplitude of the low frequency pulse drops heavily at the first reflection, and the compression/expansion effect on the high frequency pulse by the low frequency pulse is practically negligible after the first reflection as discussed in relation to FIG. 7 below, while the absorption down sliding of the high center frequency prevails for the whole propagation distance of the multiply scattered pulse. Hence the frequency distance between the $1^{st}$ order scattered signal (single scattering) and the pulse reverberation (multiple scattering) noise can be made to increase with depth in the image, as illustrated in FIG. 2. In this F*igure* 201 shows an anticipated variation of the center frequency of the $1^{st}$ harmonic component of the $1^{st}$ order back scattered signal, with a signal bandwidth $B_1(r)$ that increases with depth illustrated by the boundary lines 202 produced by compression of the high frequency pulse by the low frequency pulse. The center frequency of the pulse reverberation noise decreases with depth due to absorption and exemplified as the line $f_{rev}(r)$ shown as 203 in the Figure. The strongest sources for pulse reverberation noise are usually found close to the acoustic source giving a bandwidth $B_{rev}(r)$ of the pulse reverberation noise that is practically the same as the transmitted high frequency pulse bandwidth, and is indicated by the limit lines 204. The $2^{nd}$ harmonic band of the $1^{st}$ order back scattered signal due to the self distortion of the forward propagating pulse (104) is shown with its center frequency $2f_1(r)$ as 205 and bandwidth $B_2(r)>B_1(r)$ by the limit lines 206. The amplitude of the $2^{nd}$ harmonic component first increases with depth followed by a drop with depth due to absorption and beam divergence of the $1^{st}$ harmonic high frequency components.

A $1^{st}$ image signal with strong suppression of the pulse reverberation noise, can according to the invention now be obtained with a receiver filter which suppresses lower frequencies with a cut-off frequency that slides with depth range. In FIG. 2 is shown by way of example a receiver bandpass filter with a sliding center frequency $f_{rec}(r)$, exemplified by the line 207 with bandwidth $B_{rec}(r)$ that can vary with depth as illustrated by the boundary lines 208 in the Figure. In the near to mid range, the frequency difference between the pulse reverberation noise and the $1^{st}$ harmonic band of the $1^{st}$ order scattered signal is so low that one can not separate the two components in the frequency domain. However, the $2^{nd}$ harmonic band of the $1^{st}$ order scattered signal quickly increases in amplitude and has low reverberation noise, so that placing the receive filter frequency around the $2^{nd}$ harmonic band for low to mid depths as shown in the Figure, provides a received signal with strong suppression of the pulse reverberation noise for these depths. The $1^{st}$ image depth is usually a distance into the object where $2^{nd}$ harmonic components of the transmitted high frequency pulse have developed. Otherwise the receiver filter could let through $1^{st}$ harmonic components at the real low depths and sweep to $2^{nd}$ harmonic components in the near to mid image range. As z increases, the frequency separation between the $1^{st}$ harmonic component of the $1^{st}$ order scattered signal and the pulse reverberation noise increases, and one can slide down the receiver filter in frequency, and possibly also increase the filter bandwidth, as shown in the Figure, to include in the received signal frequency components from the $1^{st}$ harmonic band of the $1^{st}$ order scattered signal. This will give higher amplitude of the received signal, as the $1^{st}$ harmonic components are stronger and less attenuated with depth than the $2^{nd}$ harmonic components, hence preserving the sensitivity of the imaging system for deeper depths. $B_{rec}$ can increase with depth because the $1^{st}$ harmonic pulse bandwidth increases due to the described pulse length compression, and also to include both $1^{st}$ and $2^{nd}$ harmonic components for increased signal power, or one can for deep ranges decide to reduce the bandwidth to reduce receiver noise. Also, with transducer arrays where the high frequency pulse slides from the negative to the positive spatial gradient of the low frequency pulse as described above, i.e. from pulse compression to expansion, the pulse bandwidth reduces which can be matched with a reduced $B_{rec}$. One should note that the pulse reverberation noise is in the low frequency range, so that one can use a receiver high pass filter instead of the band pass filter, where the high pass filter cut-off frequency slides with z to include more of the $1^{st}$ harmonic band maintaining strong suppression of the pulse reverberation noise.

With this method one is hence able to preserve $1^{st}$ harmonic sensitivity for deep ranges with a suppression of the pulse reverberation noise similar to $2^{nd}$ harmonic imaging, allowing deeper imaging of dense objects like the liver, the kidneys, the breast, etc with higher frequencies and better resolution. The compression reduction in the high frequency pulse length also improves the range resolution in the image in a way not previously seen. With a beam profile design as discussed above, where the phase between the low and the high frequency pulse slides with depth so that the high frequency pulse is expanded for large depths, it is still possible with proper design to keep the pulse reverberation noise sufficiently separated from the $1^{st}$ order scattering in the frequency domain, so that the pulse reverberation noise can be sufficiently suppressed with the receiver filter. This modification of the method will hence provide deeper penetration, while maintaining high frequencies for better resolution in the mid to near field. One should however note that in some applications it can be advantageous to use the $2^{nd}$ harmonic band of the received signal throughout the whole image range, for best suppression of the pulse reverberation noise and also best spatial resolution in the image. The advantage of the pulse compression is then improved range resolution at deep ranges due to the pulse length compression, and also increased $2^{nd}$ harmonic frequencies at deep ranges producing narrower beams and better lateral resolution. The improved separation between the $2^{nd}$ harmonic band and the band of the pulse reverberation noise at deep ranges also improves the suppression of the pulse reverberation noise compared to standard $2^{nd}$ harmonic imaging.

The received high frequency signal is retrieved from the total scattered/transmitted signal (also including the low frequency components) by filtering, for example directly in the receiver transducer. However, the nonlinear propagation distortion of the low frequency pulse component, as illustrated in FIG. 1a, produces harmonic components of the low frequency band, and with low separation between the low and the high frequency bands, these harmonic components might produce energy from the low frequency pulse in the high frequency band. Such harmonic components can be removed by transmitting a low frequency pulse without the high frequency pulse, and storing the received signal in the high frequency band. This received signal is then subtracted from the received signals with a high frequency pulse present in the transmitted pulse complex. This procedure can be used also with the other methods according to this invention, to reduce received energy from the transmitted low frequency pulse in the high frequency band.

By placing the high frequency pulse at the positive peak of the low frequency pulse in the transmitted complex, one reduces the Mechanical Index (MI) of the high frequency pulse (due to lower negative amplitude of the total pulse complex), which allows transmission of higher high frequency amplitudes. This produces higher harmonic distortion of the high frequency pulse, increasing the sensitivity with harmonic imaging with the high frequency pulse, where the receiver filter above is set to select the harmonic bands of the high frequency pulse to suppress pulse reverberation noise.

It should be evident that one for each beam direction can transmit more than one of the pulse complexes in FIG. 1 with a subsequent processing of the received signal from each pulse as in FIG. 2, where said processed received signals are used with known further processing to produce image signals, such as for structural anatomic images, Doppler velocity images of moving scatterers and all signals derived therefrom, and frequency analysis in depth/time for characterization of the scatterers, etc., known to anyone skilled in the art. 2D and 3D images are formed by lateral scanning of the beam with possible parallel transmit and/or receive beams. One do not have the same limitations on the width of the transmit beam as with $2^{nd}$ harmonic imaging, which allows the use of wider transmit beams and more parallel receive beams for higher frame rate 2D and 3D imaging as compared to harmonic imaging.

The method of pulse compression of the high frequency pulse is also useful in situations where the radiation force of ultrasound pulses is used to push the object locally, for example to measure the shear deformation related to the shear modulus of the object, or to improve attachment of targeted contrast agent bubbles to selected tissues. With the current method one can increase frequency separation between the push pulses and the observation pulses, by placing the observation pulses at the negative spatial gradient of the low frequency pulse to increase the receive frequency of the observation pulses. The push pulses can be transmitted as longer pulses with zero low frequency pulse, or a sequence of short high frequency push pulses placed close to a positive spatial gradient of the low frequency pulse for stretching and frequency down conversion of the high frequency push pulses. In both situations the observation pulses gets higher frequencies than the push pulses and can be transmitted shortly after or during a sequence of push pulses, where the separation of the echoes from the observation pulses and the push pulses are done by filtering in the depth (fast) time domain as above.

In a $2^{nd}$ method according to the invention one transmits two or more pulse complexes with frequency components in a low and a high band which overlap in time, and where the amplitude and/or the phase and/or the frequency of the low frequency pulses vary from pulse to pulse. The method provides another type of received signal with highly suppressed pulse reverberation noise similar to the previous method according to the invention, and also allows imaging of nonlinear scattering parameters in the object, especially imaging of micro calcifications, gas bubbles, and gas filled regions, and also provides quantitative nonlinear scattering and propagation parameters of the object. We start describing the method with reference to FIG. 3a, which shows a transmitted pulse that is composed of a low frequency component 301 and a high frequency component 302, where the high frequency component is riding on the positive ridge of the low frequency pulse with amplitude $p_0$. The high frequency pulse is used for the imaging, and in the receiver, the low frequency pulse is removed through filtering. As these two pulses propagate together through the object, the amplitude of the low frequency pulse influences the scattering coefficient of the object for the high frequency components through the nonlinear variation of the compressibility and mass density as $$
\begin{aligned}
k^2\upsilon(\underline{r};\underline{e}_i\underline{e}_s) &= k^2\upsilon_0(\underline{r};\underline{e}_i\underline{e}_s) + k^2\upsilon_n(\underline{r};\underline{e}_i\underline{e}_s)p_0 \\
\upsilon_n(\underline{r};\underline{e}_i\underline{e}_s) &= -2\frac{\beta_n(\underline{r})\kappa_0^2(\underline{r}) - \beta_{na}(\underline{r})\kappa_{0a}^2(\underline{r})}{\kappa_{0a}(\underline{r})} + \\
&\quad \frac{\kappa_0(\underline{r})\rho_0(\underline{r}) - \kappa_{0a}(\underline{r})\rho_{0a}(\underline{r})}{\rho_0(\underline{r})}\underline{e}_i\underline{e}_s
\end{aligned}
\tag{9}
$$

The nonlinear compressibility term is now $\sim 2\beta_n \cdot 2.5 \sim 25$ times larger than the nonlinear mass density term and the two terms generally have opposite signs. Imaging with high frequency pulses centered at $\omega_1$, will produce a band pass filter in the range coordinate of this parameter in the frequency range around $2k_1 = 2\omega_1/c$ as described above.

Figure 3A:
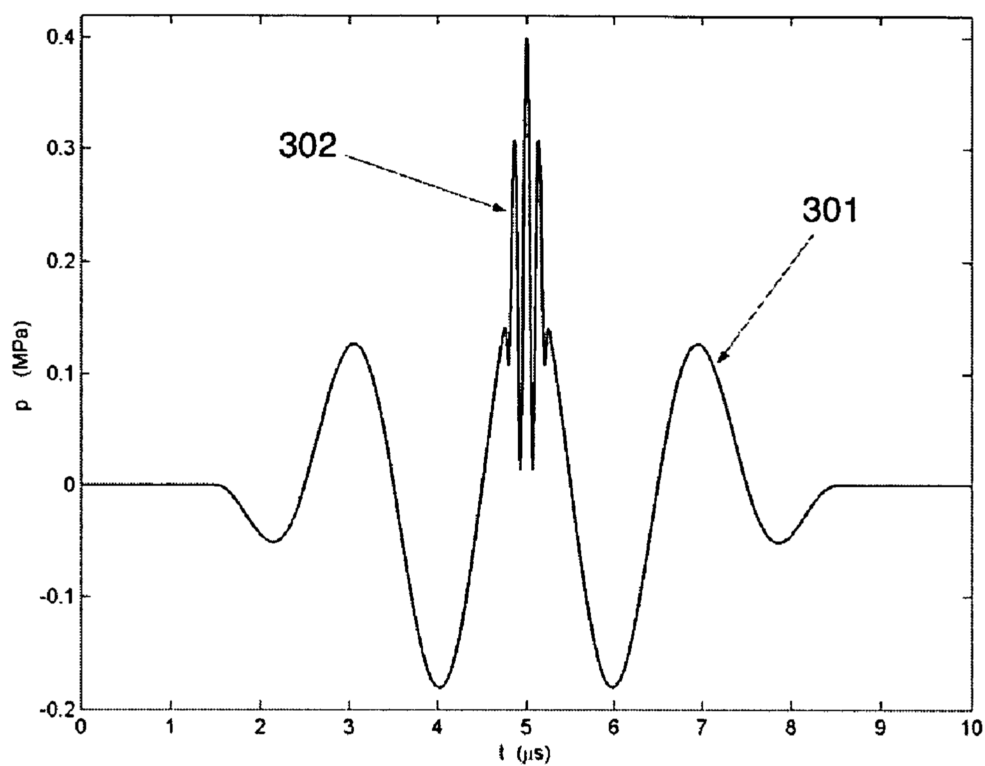
FIG. 3 illustrates a second type of transmit pulses according to the invention containing both a low frequency pulse and a high frequency pulse where the high frequency pulse is by way of example placed in the peak positive or peak negative period of the low frequency pulse.
Figure 3B:
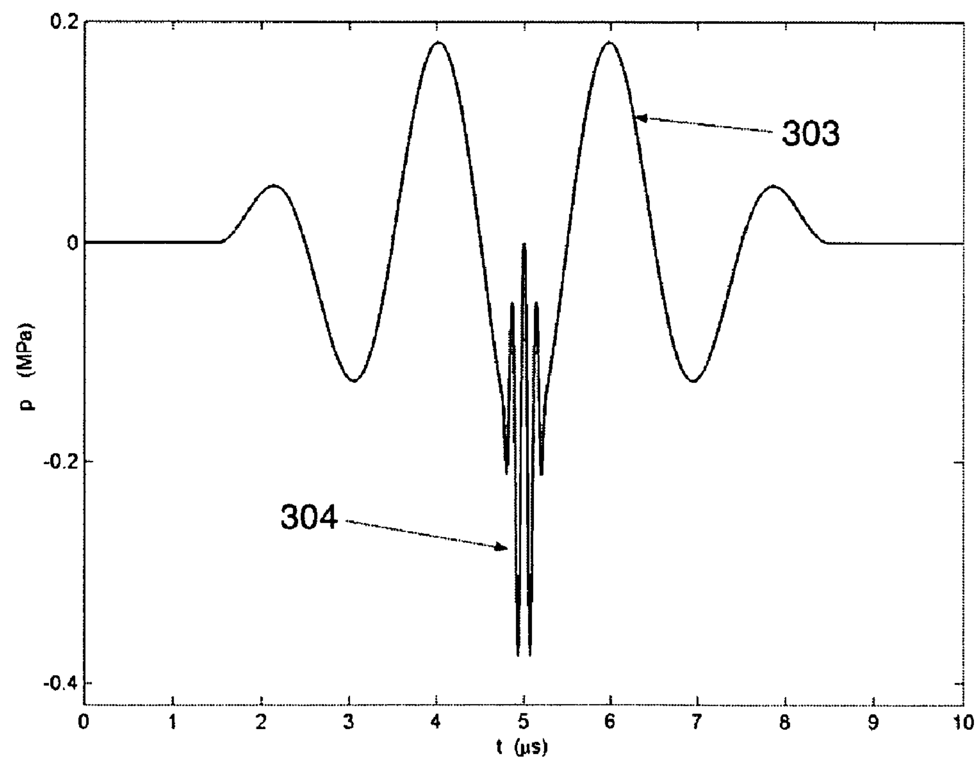

Further by example, we transmit a $2^{nd}$ pulse as illustrated in FIG. 3b, where the polarity of the low frequency pulse 303 is reversed compared to the pulse 301, while the high frequency pulse 304 has the same time position in the pulse complex as 302 in FIG. 3a, so that the low frequency amplitude at the location of the high frequency pulse is now $-p_0$. As the nonlinear scattering parameter in Eq. (9) is linear in the added pressure, $\pm p_0$, the nonlinear scattered signal from the high frequency pulse 304 in FIG. 3*b* has opposite sign to the nonlinear scattering from the high frequency pulse 302 in FIG. 3*a*. At the same time, the linear component of the high frequency scattering from the object, as given by Eq. (2), is not influenced by the low frequency pulse.

Due to the nonlinear variation of the propagation velocity with the pressure as given in Eq. (6), the propagation velocity of the high frequency pulse will vary between the pulses in FIGS. 3*a* and *b* as $\Delta c/c_{0a}=2\beta_{na}\kappa_{0a}p_0$. The back-scattered signal from the high frequency pulses are therefore time shifted for the positive and negative polarities of the low frequency pulses. The propagation velocity $c_{0a}$ for soft tissues, water, and oils have average values of ~1.5 mm/μsec. Rock shows higher velocities by a factor ~2. The time lag of the back-scattered signal from a scatterer at range r is $$t(r) = t_0(r) + \tau(r) \tag{10}$$

$$t_0(r) = 2\int_0^r \frac{ds}{c_{0a}(s)}$$

$$\tau(r) = -\int_0^r \frac{ds}{c_{0a}(s)}\beta_{na}(s)\kappa_{0a}(s)p_0(s)$$

where s is the distance along the beam axis, $t_0(r)$ is the time lag for $p_0=0$, $\tau(r)$ is the added nonlinear propagation time lag due to the nonlinear manipulation of the propagation velocity for the high frequency pulse by the low frequency pulse, and $p_0(s)$ is the amplitude of the low frequency pulse at the location of the high frequency pulse as a function of depth. We shall in the following refer to t(r) as the nonlinear propagation time lag or nonlinear propagation delay.

The high frequency pulse will also have an accumulative self-distortion as described in relation to FIG. 1*b*, which increases the harmonic bands of the high frequency pulse for a certain distance followed by reduction due to the absorption of the high frequency pulse at deeper ranges. Due to the low frequency of the low band pulse (typically 1/5-1/20 of the high frequency) the nonlinear propagation lag imposed by the low frequency pulse will prevail for much larger depths. The factor 2 in $t_0(r)$ stems from the sum of the propagation time lag of the outbound, transmitted pulse, and the time lag of the back-scattered pulse. The low frequency component will only have high enough amplitude to affect the propagation velocity of the outbound pulse, and hence this factor of 2 is not found in $\tau(r)$. As the nonlinear time lag manipulation is done on the outbound pulse, this time lag manipulation is the same for the scattered signal in all directions, also in the forward direction, which is a manipulation of the forward propagation velocity that we return to in relation to FIG. 9.

Figure 4:
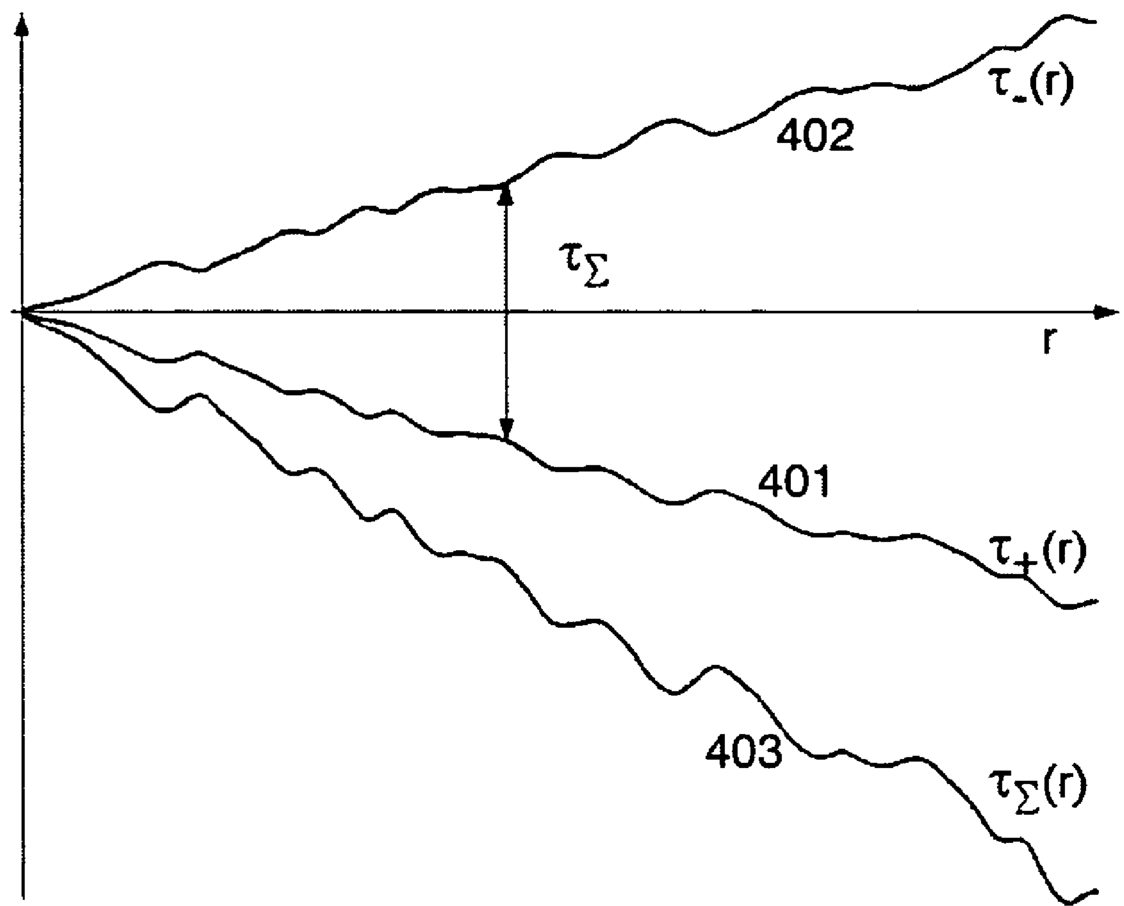
FIG. 4 illustrates the forward propagation lags of the high frequency pulse that is produced by the low frequency pulse of FIG. 3.

When the phase relations of the high and low frequency components are practically constant along the beam, this time shift will vary monotonously with the local spatial average of $\beta_{na}\kappa_a$, as shown in FIG. 4, where 401 shows $\tau_+(r)$ where the high frequency pulse rides on the positive ridge of the low frequency pulse, and 402 shows $\tau_-(r)$ where the high frequency pulse rides on the negative valley of the low frequency pulse. $\tau_\Sigma(r)$ is the difference delay between these two pulses, shown as 403.

For an amplitude of the low frequency pulse of $p_0$~1 MPa we get $\Delta c/c_{0a}=\beta_{na}\kappa_{0a}p_0\sim 2\cdot 10^{-3}$, which for a range $R=300\lambda_1=300c_{0a}T_1$ where $T_1=1/f_1$ is the period of the high frequency pulse, we get an added time lag from Eq. (10) of $\tau(R)$ up to ~$0.6T_1$, i.e. close to the period at the high band center frequency. This image range is typical for medical ultrasound imaging, while in water one can have larger ranges, and in geological applications the maximal image range can be below this value. We should note that the difference in nonlinear propagation lag for the positive and negative low frequency pulse in FIG. 3 is twice this value. Hence, even with lower amplitudes of $p_0$ down to for example $p_0$~50 kPa, one gets considerable nonlinear propagation delay according to Eq. (10), which must be compensated for to adequately extract the nonlinearly scattered signal as described below. With transmission computed tomography imaging, we have only one way propagation with no signal reduction in the scattering process, which allows for at least twice the image range with transmission computed tomography, and hence also twice the end magnitude of the nonlinear propagation delay, which we return to in relation to FIG. 9.

We now describe how the invention establishes image signals by the nonlinear manipulation of the scattering and propagation parameters of the object for the high frequency pulse, by the low frequency pulse, according to the $2^{nd}$ method of the invention. We first examine the situation with back scatter imaging and let $x_k(t)$ denote the received back scattered signal from transmitted pulse no k, where examples are given in FIG. 5. The time t reflects the depth of the scatterers and is denoted the fast time, while the pulse number coordinate k samples slower variations in the object, and is referred to as the slow time coordinate. The sample rate along the slow time coordinate is the pulse repetition frequency $f_{prf}=1/T_{prf}$, where $T_{prf}$ is the time interval between transmit pulses, and is typically chosen a little longer than the time $T_{max}$ required to collect scattered signal from the deepest image range lag. For medical imaging $T_{max}\sim 300T_1$, while for imaging in water we get larger values and for geological imaging one can even have lower values of $T_{max}$. The Figure schematically illustrates received signals for 5 slow time samples 501-505 as a function of the fast time. The signals vary as a function of the slow time coordinate due to the following effects:

- Variations in the low frequency pulse $p_{0k}$ as a function of k. In some situations according to the invention, the amplitude of the low frequency pulse is $p_{0k}\sim(-1)^k$. This gives a variation of the received signal in the slow time coordinate for fixed t produced by the nonlinear scattering and propagation with a slow time frequency ~$f_{prf}/2$, as described below.
- Movements between the scatterers and the transducer array in the range direction of the high frequency beam. This produces a Doppler shift of the received signal in the slow time coordinate for fixed t.
- Movement between the scatterers and the transducer array lateral to the beam direction. This phenomenon is for example found with lateral mechanical direction scanning of the acoustic beam or the movement of scatterers like cardiac wall or flowing oil, and produces a frequency broadening of the signal along the slow time coordinate.

A mathematical model of the back-scattered $1^{st}$ harmonic band of the high frequency signal $x_k(t)$ where the low frequency pulse switches polarity between transmit pulses, i.e. $p_{0k}\sim(-1)^k$, and the scatterers are moving, can be written as $$\hat{x}_k(t) = \{u_{1k}(t-(-1)^k\tau(t)) + (-1)^k u_{nk}(t-(-1)^k\tau(t))\} e^{i\omega_1 t + i\omega_d T_{prf}k - i\omega_1\tau(t)(-1)^k} \tag{11}$$

where $\omega_d=-2\omega_1 v_r/c_0$ is the average Doppler shift for scatterers moving with average radial velocity $v_r$ away from the transducer in each range cell along the beam. $u_{1k}(t)$ is the complex envelope of the linearly back-scattered scattered signal and $u_{nk}(t)$ is the complex envelope of the nonlinearly back-scattered signal from high frequency pulse no k with positive amplitude $p_0$ of the low frequency pulse. The envelopes vary with the pulse number coordinate k because scatterers and the beam move relative to each other, and scatterers within the range cell can move with different velocities, both producing a frequency broadening of the signal in the slow time coordinate. □(t) is the nonlinear propagation lag as a function of the fast range-time coordinate for positive amplitude of the low frequency pulse. For simplicity, we have used the analytic form $\hat{x}_k(t)$ of the received signal where the physical, radio frequency acoustic signal $x_k(t)=\mathrm{Re}\{\hat{x}_k(t)\}$. The analytic signal can be obtained from the physical signal as $\hat{x}_k(t)=x_k(t)+iH\{x_k(t)\}=x^0/k^0(t)\exp\{i\omega_1 t\}$ where $H\{\ \}$ denotes the Hilbert transform of the signal, and $\tilde{x}_k(t)$ is the complex envelope of the signal.

The $2^{nd}$ harmonic band can be represented by a similar formula as Eq. (11) where the angular frequency is $2\omega_1$, the Doppler frequency is $2\omega_d$, and the nonlinearly scattered signal is very low and can be neglected except for scattering from micro bubbles. The $2^{nd}$ harmonic band has suppressed pulse reverberation noise which can help in the estimation of the nonlinear propagation delay which we return to in relation to Eq. (21).

The pulse-to-pulse switching of the nonlinear delay, $(-1)^k\tau(t)$, has strongest effect in the phase as the phase switching $(-1)^k\omega_1\tau(t)$ compared to the delay switching of the envelopes, $t-(-1)^k\tau(t)$, because the bandwidth of the signal is limited. To visualize the effect of the delay switching on the envelopes we separate the envelopes in an even and an odd function around t, which allows us to express the complex envelope of the received signal as $$\tilde{x}_k(t)=\{(u_{1k}{}^e(t,\tau(t))-u_{nk}{}^o(t,\tau(t)))+(-1)^k(u_{nk}{}^e(t,\tau(t))-u_{nk}{}^o(t,\tau(t)))\}e^{i\omega_d T_{prf}k-i\omega_1\tau(t)(-1)^k} \tag{12}$$

$$u^e_{qk}(t,\tau)=\frac{1}{2}\{u_{qk}(t+\tau)+u_{qk}(t-\tau)\} \qquad q=1,n$$

$$u^o_{qk}t,\tau)=\frac{1}{2}\{u_{qk}(i+\tau)-u_{qk}(t-\tau)\}$$

where the superscript e denotes the even components and o denotes the odd components in τ around t. The even component is unchanged by a change in sign of □, while the odd component changes sign. We note that $(-1)^k=\exp\{i\pi k\}=\exp\{ikT_{prf}\omega_{prf}/2\}$, where $\omega_{prf}=2\pi/T_{prf}$ is the angular pulse repetition frequency and hence the angular sampling frequency in the slow time coordinate. Introducing this expression we can further develop Eq. (12) to $$\tilde{x}_k(t)=\left\{\underbrace{(u^e_{1k}-u^o_{nk})\cos\omega_1\tau(t)}_{A}-\underbrace{i(u^e_{nk}-u^o_{1k})\sin\omega_1\tau(t)}_{D}\right\}e^{i\omega_d T_{prf}k}+ \tag{13}$$
$$\left\{\underbrace{(u^e_{1k}-u^o_{nk})\cos\omega_1\tau(t)}_{A}-\underbrace{i(u^e_{1k}-u^o_{nk})\sin\omega_1\tau(t)}_{B}\right\}e^{i(\omega_d+\omega_{prf}/2)T_{prf}k}$$

Figure 6A:
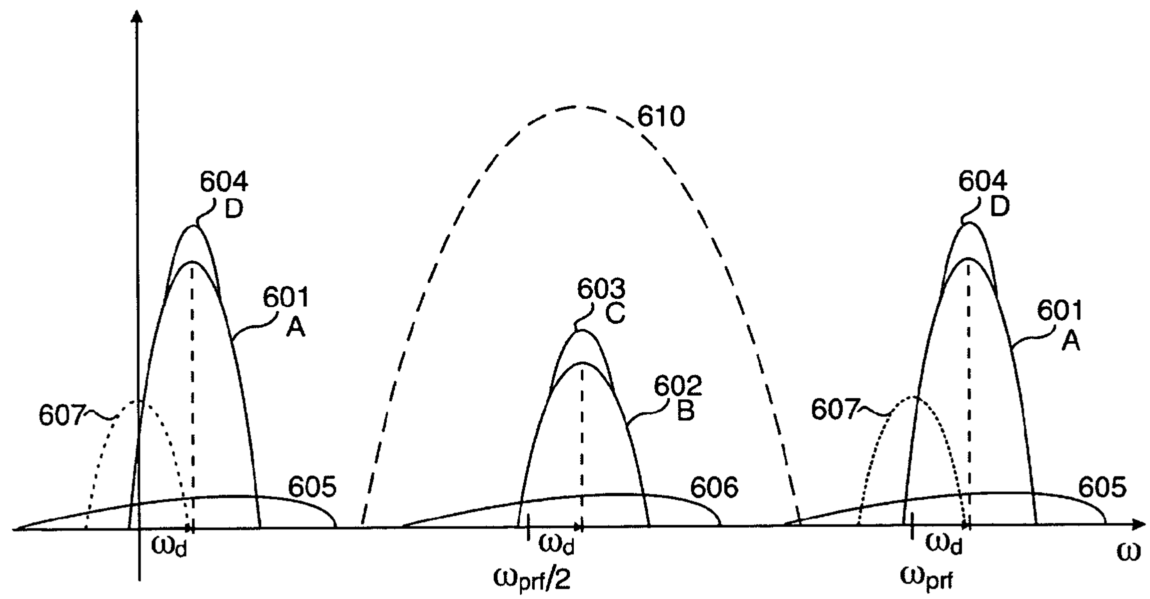
FIG. 6 illustrates received linear and nonlinear frequency lines along the slow time frequency coordinate.

For fixed fast time t, the signal is in the slow time coordinate k composed of 4 components (frequency lines) as illustrated in FIG. 6*a*, where 601 shows the frequency line A of $(u^e_{1k}-u^o_{nk})\cos\omega_1\tau(t)\exp\{i\omega_d T_{prf}k\}$ centered around the average Doppler shift $\omega_d$, 602 shows the line B of $-i(u^e_{1k}-u^o_{nk})\sin\omega_1\tau(t)\exp\{i(\omega_d+\omega_{prf}/2)T_{prf}k\}$ centered around $\omega_d+\omega_{prf}/2$, 603 shows the line C of $(u^e_{nk}-u^o_{1k})\cos\omega_1\tau(t)\exp\{i(\omega_d+\omega_{prf}/2)T_{prf}k\}$ centered around $\omega_d+\omega_{prf}/2$, and 604 shows the line D of $-i(u^e_{nk}-u^o_{1k})\sin\omega_1\tau(t)\exp\{i\omega_d T_{prf}k\}$ centered around $\omega_d$.

The lines are generated through a mixing of linear and nonlinear scattering with the pulse to pulse switching of the nonlinear propagation delay, $(-1)^k\tau(t)$. With no nonlinear delay switching, i.e. τ=0, the odd components become zero and the even components are equal to the original envelopes. The lines 602 and 604 disappear and all the linearly scattered power is contained in the line 601 centered around $\omega_d$, while the nonlinear scattered power is contained in the line 603 centered around $\omega_d+\omega_{prf}/2$.

The effect of the nonlinear propagation delay switching is strongest in the phase of the signal because the limited signal bandwidth, where it produces a frequency mixing with a shift $\omega_{prf}/2$. It also produces a frequency mixing with a shift of $\omega_{prf}/2$ by its participation in the envelopes as $t-(-1)^k\tau(t)$ through the odd components of the envelopes for the linear scattering, $u^o_{1k}(t)$, and the nonlinear scattering, $u^o_{nk}(t)$, while the envelope delay switching has no frequency shift effect on the even components of the envelopes. The delay shifting in the phase produces a shifting of part of the linearly scattered power from centered around $\omega_d$ to the line 602 centered around $\omega_d+\omega_{prf}/2$ represented by the even component $u^e_{1k}$. A combined switching in the phase and the envelope shifts part of the power from centered around $\omega_d$ to centered around $\omega_d+\omega_{prf}/2$ and back to centered around $\omega_d$ as part of line 604 represented by the odd component $u^o_{1k}$. Similarly, the nonlinear delay switching shifts part of the nonlinear scattered power from line 603 to 604 through the switching in the phase and represented by the even component $u^e_{nk}$, while a combined switching in the phase and the envelope shifts part of the power from centered around $(\omega_d+\omega_{prf}/2$ to centered around $\omega_d$ and back to centered around $\omega_d+\omega_{prf}/2$ as part of line 602 represented by the odd component $u^o_{nk}$.

We note that as τ increases, the amplitude of the line 601 drops ~cos $\omega_1\tau(t)$, while the amplitude of the line 602 increases ~sin $\omega_1\tau(t)$ and becomes maximum when $\omega_1\tau(t)=\pi/2$, which also gives zero for the line 601. This means that most of the linearly scattered power is moved from being centered around $\omega_d$ to being centered around $\omega_d+\omega_{prf}/2$ by the delay switching in the phase, but some linearly scattered power is mixed back to centered around $\omega_d$ as part of line 604 through the odd component of $u_{1k}(t)$. The same effect is found for the nonlinear scattering, where as τ increases the amplitude of the line 603 drops ~cos $\omega_1\tau(t)$, while the amplitude of the line 604 increases ~sin $\omega_1\tau(t)$ and becomes maximum when $\omega_1\tau(t)=\pi/2$, which also gives zero for the line 603. Most of the nonlinearly scattered power is moved from centered around $\omega_d+\omega_{prf}/2$ to centered around $\omega_d$ by the delay switching in the phase, but some nonlinear power is mixed back to centered around $\omega_d+\omega_{prf}/2$ as part of line 602 through the odd component of $u_{nk}(t)$.

If the range cell also covers moving blood or other fluids like oil, the linear scattering from moving fluid will produce additional and usually wider spectra where the power is divided between 605 with the original Doppler shifts $\omega_d=-2\omega_1 v_r/c$ where $v_r$ is the spread fluid velocity, and 606 with frequencies $\omega_d+\omega_{prf}/2$. The mixing of the fluid signal with the switching in the nonlinear propagation delay follows the same rules as for the linear scattering from the object in lines 601 and 602. The nonlinear scattering from the fluid is, however, so week that it will disappear in the noise.

Figure 7A:
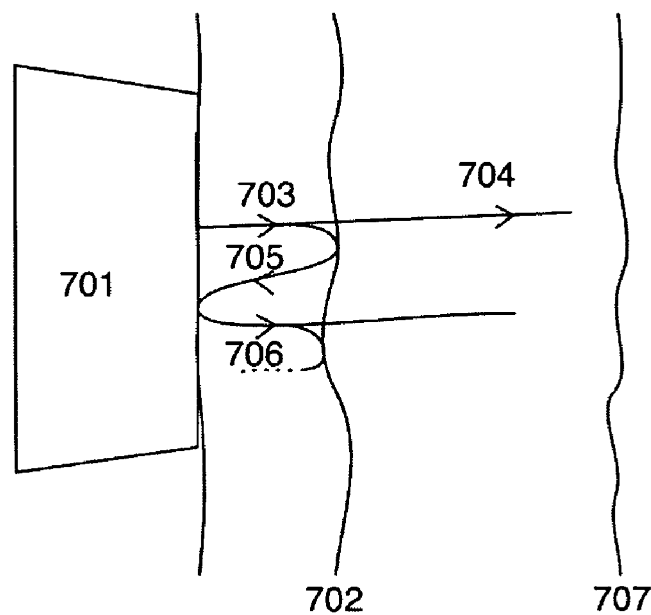
FIGS. 7 *a* and *b* illustrates how pulse reverberations experience less nonlinear propagation manipulation by the low frequency pulse than the first order scattered signals.
FIG. 7*c* illustrates the depth dependent processing gain produced by the method of suppressing the pulse reverberations in the signal.

The signal model in Eqs. (11-13) includes only the first order scattered signal, where the out-going high frequency pulse follows the low frequency pulse. With multiple scattering, also called reverberations, of the outgoing high frequency pulse, we get some modifications of the multiply scattered signal from this model. The amplitude of the low frequency scattered pulse is low, and hence its nonlinear delay effect on the propagation velocity of the scattered high frequency pulse, Eq. (6, 10), can be neglected. This is especially important for reverberations of the outgoing pulse in the body wall, where FIG. 7*a* shows an example structure of the transducer array 701 and body wall reflectors. 702 shows a strong reflector in front of the array. The transmitted pulse follows a path indicated by 703, where the pulse on the first hit on the reflector 702 is partially transmitted as 704 and partially reflected as 705. The reflected pulse is then again reflected from the transducer surface, or other strong reflectors to generate the reflected pulse 706 that is again partially transmitted and partially reflected, and so forth.

Figure 7B:
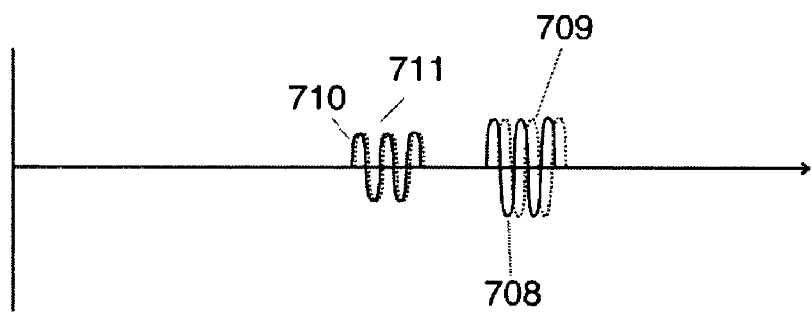
Figure 7C:
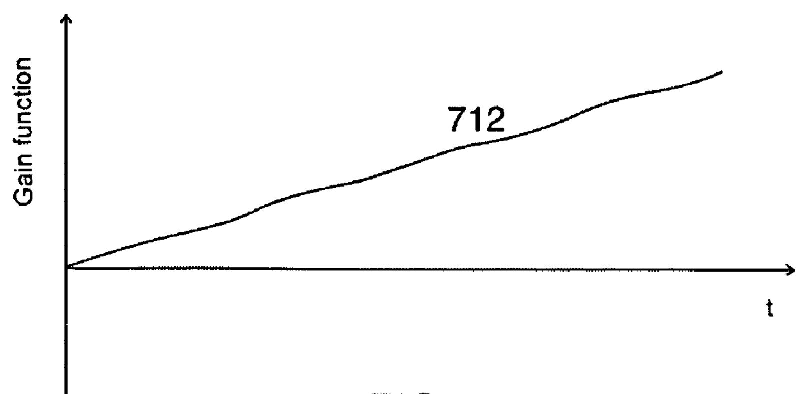

The reflected original pulse from a deeper reflector 707 is shown as 708 in FIG. 7*b* for the positive low frequency pulse, and as 709 for the negative low frequency pulse, where these pulses have a delay difference given by variations in the nonlinear propagation delay of Eq. (10). The twice reflected pulse from the reflector 702 is shown as 710 for the positive low frequency pulse. Upon the first reflection at 702, the pulse amplitudes are reduced, and the reduction in amplitude of the low frequency pulse greatly reduces the time lag manipulation of Eq. (10) for the reverberation pulses, compared to the forward propagating pulse. The twice reflected pulse from 702 for the negative low frequency pulse, will therefore only have minor difference in delay from 710, and is therefore indicated as 711 overlapping 710 in the Figure. The pulse reverberations of the out-going pulse in the body wall will hence be found as a frequency line centered around $\omega=0$, illustrated as the dotted line 607 in FIG. 6*a*, where the delay mixed line around $\omega_{prf}/2$ is very low in amplitude.

We are now in position to describe and discuss how several new image parameters can be extracted from the propagated and scattered acoustic signals according to the $2^{nd}$ method of the invention, to form new and improved acoustic images of the object structures and velocities of scatterers. The extraction of the parameters can be exemplified based on the received sequence of signals $x_k(t)$.

The $1^{st}$ image signal that is extracted according to the $2^{nd}$ method of the invention, is based on the reverberation corrected scattering signal obtained by band pass filtering the received sequence in the slow time domain around $\omega_{prf}/2$, for example as indicated by the band pass filter 610 in FIG. 6*a*. This filter highly attenuates the reverberation line 607 and extracts the lines 602 and 603, where the linear scattering components highly dominates the nonlinear scattering components in these two lines. Combining the received high frequency signals in for example a filter that attenuates the low frequency slow time components while letting through slow time components in a band as is common with Doppler image processing, one can get a set of reverberation corrected, linearly scattered signals as $$\tilde{z}_{1k}(t) = -\{u^{o}_{1k}(t,\tau(t))\cos\omega_1\tau(t) + iu^{e}_{1k}(t,\tau(t))\sin\omega_1\tau(t)\}e^{i(\omega_d+\omega_{prf}/2)T_{prf}k} \tag{14}$$

The amplitudes of these signals increase monotonously with τ. By choosing adequate frequency of the low frequency field (e.g. $\omega_0 \sim \omega_1/10$), the absorption attenuation of the low frequency field will be very low within the image range, and vary little between different objects and individuals at defined depth ranges. We can hence design the low frequency field and pulse amplitude so that we get a monotone increase in $\tau(t)$ as in FIG. 4, to get a monotonously increasing depth variable processing gain function for the reverberation corrected linear scattering, illustrated as 711 in FIG. 7*c*. Designing the low frequency field so that $\omega_1\tau(T_{max})=\pi/2$, where $T_{max}$ is the maximal range-time, we get a close to maximum of this gain curve at $T_{max}$. This depth variable processing gain will participate together with the user-controlled depth variable gain available in acoustic imaging instruments, reducing the need for user interference on the depth gain controls. Movement of the object, as the myocardium, can produce Doppler shifts that can pass through the filter together with the components in Eq. (14). This can be an advantage as the stationary body wall pulse reverberation noise is highly attenuated, the movement helps the $1^{st}$ order signal from object structures to pass through the filter, hence improving the image, for example of the apical region of the heart.

The filter outputs will also contain the nonlinearly scattered components of lines 602 and 603 as $$\tilde{z}_{nk}(t) = \{u^{e}_{nk}(t,\tau(t))\cos\omega_1\tau(t) + iu^{o}_{nk}(t,\tau(t))\sin\omega_1\tau(t)\}e^{i(\omega_d+\omega_{prf}/2)T_{prf}k} \tag{15}$$

which is maximum for τ=0, and decreases with depth as □ increases. However, the nonlinear scattering signal component in Eq. (15) will be negligible compared to the linear scattering signal component in Eq. (14).

The signals after the band pass filter can be used for further Doppler processing to produce Doppler spectra and radial Doppler image lines of scatterer velocities according to known methods, where the full 2D or 3D image then is generated by lateral sweeping of the beam. This method is particularly useful for Doppler estimation of myocardial displacements and displacement strain (radial gradient of displacement), as the reverberation noise strongly interferes with such estimations. For fluid velocity measurements, one should note that the object clutter signal in Eq. (14) is found around $(\omega_{prf}/2$, and to suppress the object clutter to estimate the fluid signal, one can either use a band stop filter in slow time around $\omega_{prf}/2$, or frequency mix the signal from $\omega_{prf}/2$ to $\omega=0$, and use standard, high pass type clutter filtering before estimating Doppler frequencies of the fluid signal.

One can also use slightly different and overlapping beam directions for each k, for example as obtained with a continuous sweep of the beam with an annular array. One might then also use an IIR filter for slow time filtering (band pass, low pass, high pass), where a low pass filter is illustrated in Eq. (77) for similar processing.

A first signal according to the $2^{nd}$ method of the invention to be used for a radial image line for the strength of the linear back scattering with suppression of the pulse reverberations, can hence be obtained as the envelope of one of the $\tilde{z}_{lk}(t)$ of Eq. (14), or the average envelopes of the $\tilde{z}_{lk}(t)$ for several k's. One can also form a linear combination of a set of received high frequency signals $x_k(t)$, for example similar to Eq. (19) without delay corrections, that attenuates slow time frequency components around $\omega=0$ while passing through slow time frequency components around $\omega_{prf}/2$, to produce the signal $z_1(t)$ as a reverberation corrected linear scattering signal for the radial image line determined by the beam direction, and form the envelope $a_1(r)$ as $$a_1(r) = Env\{z_1(2r/c)\} \qquad z_1(t) = \sum_k (-1)^k h_k x_k(t) \tag{16}$$

where Env{ } is the envelope operator and r=ct/2 is the depth range along the beam, and the formula for $z_1(t)$ is an example band pass combination as in Eq. (19). The full 2D or 3D image is then obtained by lateral scanning of the beams.

The pulse reverberations are reduced by the accumulative delay effect of the nonlinear propagation velocity manipulation by the pressure, the same effect that forms harmonic distortion in the forward propagating pulse that is utilized in harmonic imaging. However, with the current method the nonlinear propagation is produced by the low frequency pulse which has so low absorption that the sensitivity with the method is similar to that for $1^{st}$ harmonic imaging. This allows the use of higher imaging frequencies than with $2^{nd}$ harmonic imaging with improved resolution, and particularly allows better imaging at deep ranges in dense objects like the liver, the kidneys, and the breast.

As the transmit beam with this method is a $1^{st}$ harmonic beam, it is easier to make a broader transmit beam with this method than with a $2^{nd}$ harmonic transmit beam. This allows use of more parallel receive beams to increase frame rate with 3D acoustic imaging.

To separate the nonlinear scattering components from the linear scattering components, one must delay correct (time shift compensate) the received signals, so that the frequency shift mixing of the switching nonlinear propagation delays disappears for the linear signal and line 602 disappears to leave only the nonlinear scattering line 603 in the band around $\omega_{prf}/2$. The delay correction will depend on the amplitudes and/or the phases of the low frequency pulses relative to the high frequency pulses, and also varies with depth according to Eq. (10), and as exemplified in FIG. 4.

According to one aspect of the invention, one can estimate delay corrections $\tau_k(t)$ by maximizing the power in the signal $$\hat{z}_{1c}(t) = \sum_{k=0}^{K-1} \hat{x}_k(t + \tau_k(t)) \tag{17}$$

Generally there is no reference signal, so for determining the delay corrections one must use one of the signals as reference, where the delay correction for this signal becomes zero. We hence can determine only K−1 independent delay corrections according to the methods discussed below. The summation represents a low pass filter in the slow time domain with the frequency transfer function $$H_1(\omega) = e^{i(K-1)\pi\omega/\omega_{prf}} \frac{\sin K\pi\omega/\omega_{prf}}{\sin\pi\omega/\omega_{prf}} \tag{18}$$

Figure 6B:
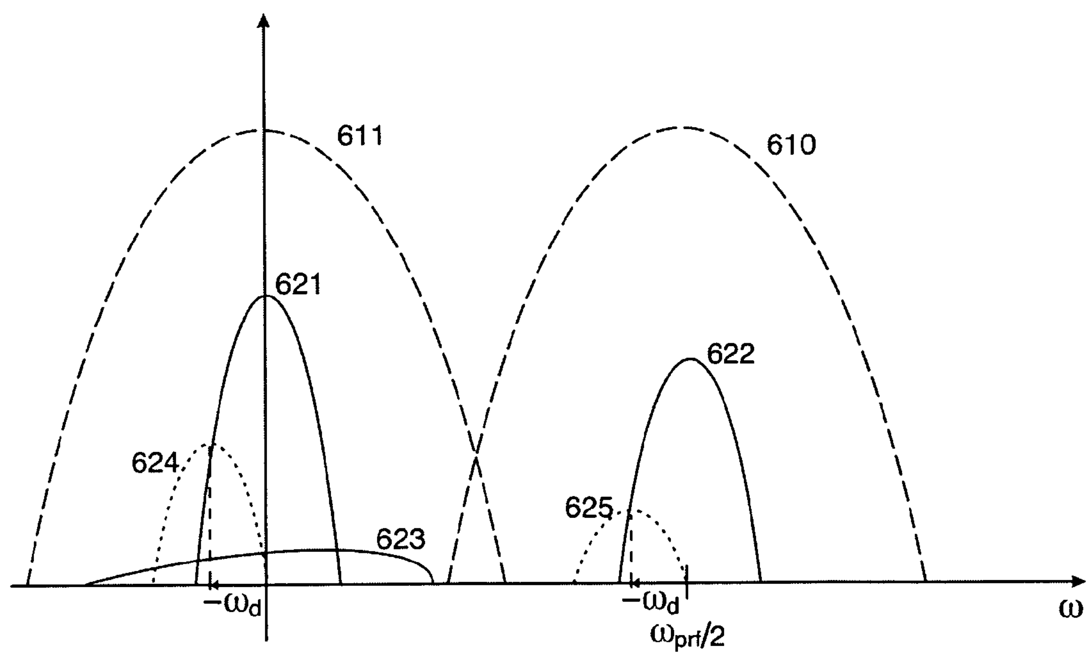

One can also use other variations of low pass filters, for example illustrated as 611 in FIG. 6*b*. This is for example obtained by introducing weights $w_k$ in the sum in Eq. (17) as a FIR filter, but an IIR filter can also be used, especially with a continuous sweep of the beam as with an annular array, according to known methods.

The delay corrections $\tau_k(t)$ introduce a frequency mixing, which move all the linearly scattered power to the line 621 in FIG. 6*b*, centered around ω=0 because the delay corrections in Eq. (17) also removes the Doppler off-set $\omega_d$ as described below. The frequency mixing of the delay corrections also moves the nonlinearly scattered power to line 622 centered around $\omega=\omega_{prf}/2$.

The nonlinearly scattered signal can hence be obtained after delay corrections as $$\hat{z}_{nc}(t) = \sum_{k=0}^{K-1} (-1)^k h_k(t)\hat{x}_k(t + \tau_k(t)) \tag{19}$$

where the summation represents a band-pass filter around $\omega_{prf}/2$ which for example with $h_k(t)=1$ takes the form $$H_n(\omega) = e^{i(K-1)\pi\omega/\omega_{prf}} \frac{\sin K\pi\omega/\omega_{prf}}{\cos\pi\omega/\omega_{prf}} \tag{20}$$

where other values for $h_k(t)$ produces modifications to this filter, for example to the filter indicated as 610 in FIG. 6*b*.

The linear combination in Eqs. (17,19) give one signal output in the slow time domain, where it is clear to anyone skilled in the art to modify the equations as FIR or IIR filters that produces a set of output signals in the slow time domain similar as to discussed in relation to Eqs. (14, 16). Such sets of signals in the slow time domain would be used for further Doppler processing of the signals in the slow time domain, to form Doppler velocity or displacement strain of strain rate images of the object scatterers and fluid according to known methods.

To estimate the delay corrections we can according to one embodiment of the invention, divide the received time/depth interval T into shorter time intervals $\{T_i, i=1, \ldots, I\}$ that possibly overlap so that $T \leqq \Sigma_i T_i$, and we estimate optimal delay corrections for each interval $T_i$ separately. The power of $z_1(t)$ in $T_i$ is then given by the functional $$J_{1i} = \int_{T_i} dt \left|\hat{z}_{1c}(t)\right|^2 = \sum_{k,l} \hat{R}^i_{kl}(\tau_{il} - \tau_{ik}) \tag{21}$$

$$\hat{R}^i_{kl}(\tau_{il} - \tau_{ik}) = \int_{T_i} dt \hat{x}^*_k(t + \tau_{ik})\hat{x}_l(t + \tau_{il})$$

and the delay corrections are estimated by maximizing $J_{1i}$ with respect to $\tau_{ip}$. Examples of maximizing procedures are given below.

The nonlinear self distortion of the high frequency pulse described in FIG. 1 in relation to Eq. (6), produces a harmonic conversion drop in the $1^{st}$ harmonic high frequency band with propagation distance. This conversion drop is slightly different for negative $p_0$ than for positive $p_0$, producing small differences in the amplitude of the linearly scattered $1^{st}$ harmonic high frequency signal from the object for positive and negative $p_0$. Also, inaccuracies in the transmit amplifiers can make it difficult to transmit the specified amplitudes exactly providing amplitude inaccuracies in the received signals. For improved suppression of the linearly scattered high frequency signal in Eq. (19), we can let $h_k$ vary with k so that the power in $z_{nc}(t)$ is minimized over each interval $T_i$. Such $h_k$'s can for example be found by minimizing the power in $z_{nc}(t)$ in each interval with respect to $h_k$, after delay corrections of the signals. This reduces to minimizing the following functional $$J_{ni} = \int_{T_i} dt \left|\hat{z}_{nc}(t)\right|^2 - \lambda_i \sum_k h_{ik}^2 \tag{22}$$

$$= \sum_{k,l} h_{ik} h_{il} \hat{N}^i_{kl}(\tau_{il} - \tau_{ik}) - \lambda_i \sum_k h_{ik}^2$$

$$\hat{N}^i_{kl}(\tau_{il} - \tau_{ik}) = (-1)^{k+l} \hat{R}^i_{kl}(\tau_{il} - \tau_{ik})$$

Examples of minimizing procedures are given in Eqs. (55-58). The variation in $h_k$ also take care of variations in the transmit amplitude of the high frequency components when the amplitude and/or polarity and/or phase and/or frequency of the low frequency pulse change between transmitted pulses. The delays $\tau_{ip}$ are then efficiently obtained by maximizing $J_{1i}$, while the $h_k$'s are obtained by minimizing $J_{ni}$.

The maximization of $J_{1i}$ estimates an average delay correction for each interval $T_i$. For best correction according to Eq. (17), one should assign these delay estimates to a point inside the corresponding intervals $T_i$, and produce an interpolated delay correction estimates $\tau_k(t)$ at each sample point of the fast time t between these selected points. The selected points can for example be the center of the intervals or the point of gravity of the power in the received signals in the corresponding intervals, or similar. Several methods of interpolation can be used, such as linear interpolation, spline interpolation to any degree, and Fourier interpolation.

The linearly scattered signal from the object in the lines 605 and 606 of FIG. 6*a*, will in the delay correction process move to 623 in FIG. 6*b*, in the same manner as the linearly scattered signal from the fluid, after which it can be processed according to well known Doppler processing methods. For the reverberation signal in 607, the frequency mixing of the delay corrections produces a spread of the energy to a line 624 centered at $-\omega_d$, and a line 625 centered at $\omega_{prf}/2-\omega_d$. The reverberation noise will therefore introduce errors in the estimation of the corrections for the nonlinear propagation delays by the maximization of $J_{1i}$ in Eq. (21), and frequency shift mixing of the delay corrections will introduce reverberation noise in the same slow time frequency band as the nonlinear scattering after the delay corrections (line 625) and hence introduce noise in the nonlinear scattering signal estimate for example according to Eq. (19). The image signals described in Eqs. (24-30) below will therefore be more influenced by pulse reverberation noise than the image signal based on Eqs. (14, 16).

With reference to the discussion in relation to FIGS. 1 and 2, it should be evident that one could use other than the $1^{st}$ harmonic band of the received signals, particularly the $2^{nd}$ harmonic band, in the analysis in Eqs. (14-22) above. The $2^{nd}$ harmonic band is mainly produced by the forward self-distortion of the pulse, shown as 104 in FIG. 1, that locally is scattered both linearly and nonlinearly as in Eq. (9). As the self-distortion is low in multiple scattered pulses, the $2^{nd}$ harmonic band of the received high frequency signals will have substantial suppression of reverberation noise as discussed in relation to FIG. 2. With strong reverberation noise it can be advantageous to use the $2^{nd}$ harmonic components of the back scattered signals in Eq. (21) for estimation of the nonlinear propagation delays. Using the $2^{nd}$ harmonic band for the signal in Eq. (14, 16) will then produce an added suppression of the pulse reverberation noise, particularly where one of the multiple scatterers are moving. Using the $2^{nd}$ harmonic band in Eq. (19) gives the $2^{nd}$ harmonic band of the local nonlinearly scattered signal. One can also use the $2^{nd}$ harmonic band for estimation of the nonlinear propagation delays and then apply the delay corrections on the $1^{st}$ harmonic band of the received signal for estimation of the $1^{st}$ harmonic band of the nonlinearly scattered signal as above. The methods described in U.S. Pat. No. 6,485,423 and U.S. Pat. No. 6,905,465 can also be useful in conjunction with the current invention for reducing influence of pulse reverberations in the estimation of the nonlinear delays.

Below, we shall also show a $3^{rd}$, Eqs. (42-44), and a $4^{th}$, Eqs. (45-48), method according to the invention where the effect of the pulse reverberation noise is suppressed directly in the estimation of the propagation delays. Before we discuss these methods we shall see how we can extract multiple image parameters signals with the $2^{nd}$-$4^{th}$ method of the invention.

The maximization of $J_{1i}$ with $z_{1c}$ as presented in Eq. (17), introduces delay corrections for both the nonlinear propagation time lag and the average Doppler time lag produced by object/transducer displacement in the interval $T_i$. The reason for this is that the summation filter as in Eqs. (17, 18) has a slow time frequency response with a maximum for $\omega=0$, and the maximum of $J_{1i}$ is found when all the linear energy is shifted to centered around $\omega=0$. With a slow time low pass filter with a flat response around $\omega=0$, and strong attenuation around $\omega_{prf}/2$, one could have a maximum of $J_{1i}$ that yields only the nonlinear propagation delays where the linearly scattered energy of lines 602 and 603 is moved to the filter pass band, without correction for the Doppler delay. However, such a filter is difficult to make with the limited number of slow time pulses used for each radial image line, and hence we get most robust estimation by using a low pass filter with a defined maximum at $\omega=0$. The delay correction estimation then represents total propagation delay as the sum of the nonlinear propagation delay and average Doppler displacement delays (i.e. Doppler delay) of the relative movement between object scatterers and transducer.

As noted in relation to Eq. (17) we can estimate K−1 nonlinear propagation delays, i.e. one less than the number of signals. With three or more signals, accurate estimation of the delay corrections for the signal modeled in Eqs. (11-13) and a filter with maximal frequency response at $\omega=0$, then gives the error free delay corrections as the total propagation delays which are the sum of the nonlinear propagation delays and the Doppler delays $$\tau_k(t)=(-1)^k\tau(t)+2v_r(t)T_{prf}k/c=(-1)^k\tau(t)+k\tau_d \tag{23}$$

where $\tau_d=2v_r(t)T_{prf}/c$ is the Doppler displacement delay due to radial scatterer displacement $v_r(t)T_{prf}$ between transmitted pulse complexes. The Doppler phase shift and Doppler frequency can be found as $$\begin{aligned} \varphi_{dk}(t) &= -\omega_1(\tau_k(t)+\tau_{k-1}(t))/2 \quad \text{a)} \\ &= -(2k-1)\omega_1\tau_d/2 \\ \omega_{dk}(t) &= \{\varphi_{dk}(t)-\varphi_{d,k-1}(t)\}/T_{prf} \quad \text{b)} \\ &= -\omega_1\tau_d/T_{prf} \\ &= -2\omega_1 v_r(t)/c \end{aligned} \tag{24}$$

This Doppler estimate is interesting to determine the radial displacement (from the phase in Eq. (24a) and velocity (from the angular frequency in Eq. (24b) of objects, for example the myocardium, as well as the radial displacement strain and strain rate as the radial gradient of the radial displacement and scatterer velocities. To estimate the Doppler shifts of scatterers in clutter noise, like blood or other fluids, one would first use a clutter high pass filter before the Doppler estimations, as described in relation to FIG. 12 and known according to prior art. An estimate of the displacement strain of the scatterers along the radial beam direction can be obtained from the differential of $\phi_{dk}(t)$ along the fast time. Similarly one can obtain an estimate of the radial displacement strain rate of the scatterers from the differential of $\omega_{dk}(t)$ along the fast time.

The nonlinear propagation delay is found as $$\tau(t)=\{\tau_k(t)-\tau_{k-1}(t)\}/2(-1)^k-\tau_d/2(-1)^k \tag{25}$$

As the estimation of $\tau_{ik}$ contains errors, one can reduce the estimation error by averaging Eqs. (24,25) over neighboring k. With lateral movements of the scatterers or a fast mechanical sweep of the acoustic beam, there might be an inherent variation of $\tau_{i,k}$ with k due to exchange of the object structures in the beam from pulse to pulse, where one should limit number of pulses (k) to average over.

As $p_0(r)$ can be determined from apriori measurement due to the low absorption of the low frequency pulse, one can from the nonlinear propagation delays estimate a 1st quantitative nonlinear imaging parameter, representing the nonlinear forward propagation properties of the material. The increment in the delay corrections between neighboring intervals $T_i$ represents a nonlinear forward propagation parameter that can be written as $$\delta\tau_{i,k}=\tau_{i,k}-\tau_{i-1,k}=-\frac{T_i}{2}\beta_{nia}\kappa_{ia}p_{0ik} \tag{26}$$

where $\beta_{nia}$ and $\kappa_{ia}$ are spatial averages over the range interval corresponding to $T_i$, and $p_{0ik}$ is the average amplitude of the low frequency component in the same range interval corresponding to transmit pulse no k. The 1st quantitative nonlinear image parameter/signal (nonlinear propagation image parameter) is then obtained from Eq. (26) as $$np_i=-\frac{2\delta\tau_{ni,k}}{T_i p_{0ik}}=\beta_{nia}\kappa_{ia} \tag{27}$$

A 2nd image signal to be used for imaging according to the invention, is the envelope $a_{nc}(r)$ of the nonlinearly scattered signal $z_{nc}(2r/c)$ of Eq. (19). This envelope is related to the nonlinear scattering parameters of the material as $$a_{nc}(r)=Env\{z_{nc}(2r/c)\}\sim k_1^2\upsilon_n(r)p_0(r)G(r)\exp\left\{-2f_1\int_0^r ds\,\mu(s)\right\} \tag{28}$$

where $\upsilon_n(r)$ is bandpass filtered around $2k_1$ as discussed in relation to Eqs. (2,9) and averaged laterally together with the amplitude of the low frequency pulse $p_0$ across the high frequency beam profile for range r. The exponential term describes the absorption attenuation of the high frequency acoustic pulse in the object, and is compensated for by the user adjustable time/depth gain compensation G(r) in the acoustic instrument.

The absorption factor can be found by comparing $a_{nc}(r)$ with the envelope of a 3rd image signal, the linearly scattered signal after delay corrections, $z_{1c}(t)$ of Eq. (17), which is related to the linear scattering parameters and the acoustic absorption in the object as $$a_{1c}(r)=Env\{z_{1c}(2r/c)\}\sim k_1^2\upsilon_1(r)G(r)\exp\left\{-2f_1\int_0^r ds\,\mu(s)\right\} \tag{29}$$

where $\upsilon_1(r)$ is bandpass filtered around $2k_1$ and averaged laterally across the high frequency beam profile for range r as discussed above.

When $p_0(r)$ is known, for example through calculations or measurements as described above, we can combine the signals in Eqs. (28,29) to obtain a 2nd quantitative nonlinear image parameter/signal, the quantitative nonlinear scattering parameter/signal, of the object as $$ns(r)=\frac{a_{nc}(r)}{a_{1c}(r)p_0(r)}=\frac{\upsilon_n(r)}{\upsilon_1(r)} \tag{30}$$

This adjusted time shift then holds the propagation information of $\beta_{nia}\kappa_{ia}$ averaged over the local interval $T_i$, whereas the nonlinear scattering signal $z_{nc}(t)$ holds information of local, spatial fluctuations in $\beta_n\kappa$ in the interval $T_i$. One can also use the interpolated values of $\tau_{ik}$ along the fast time to $\tau_k(t)$, and let Eqs. (26,27) represent differentiation along the fast time samples to present a smoother version np(t) of the nonlinear image parameter $np_i$. Similarly, one can assign the values of $np_i$ to points inside the intervals $T_i$ and interpolate the values between these points for presentation of the image, similar to described for interpolation of the propagation delay above.

The methods of reducing the pulse reverberations as described in relation to FIG. 2 and Eq. (14) are useful in conjunction with methods of estimating corrections for wave front aberrations, for example as described in U.S. Pat. No. 6,485,423, U.S. Pat. No. 6,905,465 and U.S. patent application Ser. No. 10/894,387, to reduce the destructive effect of reverberation noise on the aberration correction estimation. For the aberration correction one would use an acoustic transducer array with a two dimensional distribution of elements, and the corrections are applied to each element signal before the final summation in the beam former, or in many situations one would combine the signals from neighboring elements into sub-aperture signals, where the aberration corrections are applied to the sub-aperture signals before the final beam summation, and not to the individual element signals directly. Best results in estimation of the aberration corrections are obtained when the suppression of the pulse reverberation noise is applied to all the element (or sub-aperture) signals before the estimation of aberration corrections, but it can also be applied to the summed beam signal as the effect of the pulse reverberations are reduced in correlations between the element signals and the summed beam signal, as described in the cited patents.

Writing the spatial variation of the acoustic propagation velocity as $c_{0a}(\underline{r})=c_0+\Delta c_{0a}(\underline{r})$, where $c_0$ is the constant propagation velocity assumed (~1.54 mm/μsec) when calculating the beam former delays according to assumptions of a homogeneous material, we can approximate the wave front aberration delay as $$\tau_{ab}(\underline{r})=-\int_{\Gamma(\underline{r},\underline{r}_f)}\frac{ds}{c_0}\frac{\Delta c_{0a}(\underline{s})}{c_0} \tag{31}$$

where $\underline{r}$ is the element position vector on the array surface of the actual element or sub-aperture, $\underline{r}_f$ is the position vector of the beam focus, and $\Gamma(\underline{r},\underline{r}_f)$ is the ray path from the element center $\underline{r}$ to the focus $\underline{r}_f$. To correct for the wave front aberrations, one should delay the transmit pulses for the transmit beam and the receive signals for the receive beam for the elements at location $\underline{r}$ with a correction delay $\tau_{cor}(\underline{r})=-\tau_{ab}(\underline{r})$, as described in U.S. Pat. No. 6,485,423.

There is a strong correlation between variations of mass density and compressibility between materials, which according to Eq. (3) implies that there is a correlation between variations in the compressibility and variations in the propagation velocity as $$\frac{\Delta c_{0a}(\underline{s})}{c_0} \approx -\beta_c(\beta_{na}(\underline{s})\kappa_{0a}(\underline{s}) - \beta_{n0}\kappa_0) = -\beta_c(np_i(\underline{r}) - np_{avg}) \quad (32)$$

where $\beta_c$ is a proportionality constant that is determined from experiments and we note that $\beta_{na}\kappa_a$=np is the quantitative nonlinear propagation parameter in Eq. (27), now estimated for each element or sub-aperture signal defined by the location $\underline{r}$ on the array surface. $\beta_{n0}\kappa_0$ and $np_{avg}$ are the spatial average parameter for all elements and delay intervals. Inserting this expression into Eq. (31), we obtain an approximate estimate for the aberration corrections as $$\tau_{ab}(\underline{r}) \approx \frac{\beta_c}{2}\sum_i T_i(np_i(\underline{r}) - np_{avg}) \quad (33)$$

the last sum is independent of $\underline{r}$. This estimate can also be used as a starting estimate for the procedures given in the above cited patents and patent applications.

The variation of $np_i(\underline{r})$ with $\underline{r}$ is mainly produced by the propagation through the body wall, and as it is the variation of $\tau_{ab}(\underline{r})$ with element or sub-aperture location $\underline{r}$ that produces the aberrations, one gets good results by summing for intervals i in Eq. (33) slightly past the body wall only. In this near field region it is possible to design the low frequency field so that $p_0(\underline{s})$ is approximately constant in the body wall for each element, so that it can be taken outside the integral for $\tau(\underline{r})$ in Eq. (10). We then see that we can relate the aberration correction delays directly to the nonlinear propagation delays past the body wall, and subtracted the spatial average of $\tau(\underline{r})$, $\tau_{avg}$, across all the elements, i.e.

$$\tau_{ab}(\underline{r}) \approx -\frac{\beta_c}{p_{avg}(\underline{r})}(\tau(\underline{r}) - \tau_{avg}) \quad (34)$$

$$\tau(\underline{r}) = -\int_{\Gamma(\underline{r},R_b)} \frac{ds}{c_{0a}(\underline{s})}\beta_{na}(\underline{s})\kappa_{0a}(\underline{s})p_0(\underline{s})$$

where $p_{avg}(\underline{r})$ is the spatial average of the low frequency field $p_0(\underline{s})$ along the propagation path $\Gamma(\underline{r},R_b)$ from element location $\underline{r}$ through the body wall with thickness $R_b$. As noted above, the nonlinear propagation delays could with the $2^{nd}$ method be estimated from the $2^{nd}$ harmonic band of the received signals to reduce errors produced by pulse reverberation noise. In the $3^{rd}$ and $4^{th}$ method according to the invention presented below, the pulse reverberation noise is avoided directly in the processing, while in the practical situations the use of the $2^{nd}$ harmonic band will improve the accuracy with these methods.

From Eq. (8) we see that we can estimate the local absorption coefficient $\alpha(r)$ from the differential of the center frequency of the received high frequency signal as a function of range r. However, without pulse compression the down sliding of the frequency can make the receiver transducer limit the bandwidth of the received signal. Therefore, by using the pulse compression in Eq. (7) so that it balances the absorption down sliding of the frequency, we can place the received signal in the middle of the receive transducer band to avoid down-cutting of the signal bandwidth by the receive transducer band limitations, making it possible to estimate the local power absorption from measurements of the received high center frequency and the nonlinear propagation delays $\tau(r)$ as given in Eq. (10). One estimates $\tau(r)$ for example according to the $2^{nd}$ method above, or the $3^{rd}$ and $4^{th}$ method below, in addition to a transmission of a pulse complex as in FIG. 1 where the high frequency pulse is close to a maximal spatial gradient of the low frequency pulse.

With reference to the discussion in relation to Eqs. (7,8) we get in this last situation a compression of the high frequency pulse length as $d\lambda_1 = -\beta_{na}\kappa_{0a}p_{00}k_{00}\lambda_{10}p_0(r)/p_{00}\,dr$ over a propagation distance dr, where $p_0(r)$ is the local amplitude of the low frequency pulse including variations from beam convergence/divergence and small absorption, $p_{00}$ and $k_{00}$ are the low frequency pulse amplitude and wave number at the array surface, and $\lambda_{10}$ is the high frequency wave length at the array surface. The received center frequency of the high frequency signal is related to the wave length as $f_1(r)=c_{0a}/\lambda_1(r)$, which gives $df_1 = -f_1^2/c_{0a}d\lambda_1 - 0.36B_1^2(r)\alpha(r)dr = \beta_{na}\kappa_{0a}k_{00}\lambda_{10}p_0(r)f_1^2\,dr/c_{0a} - 0.36B_1^2(r)\alpha(r)\,dr$. The pulse bandwidth is related to the pulse length $R_1$ as $B_1=c_{0a}/R_1$. Per the discussion above, the pulse length compresses over a propagation distance dr as $dR_1 = -\beta_{na}\kappa_{0a}p_{00}k_{00}R_{10}p_0(r)/p_{00}\,dr$ where $R_{10}$ is the pulse length at the array surface. The absorption down conversion preserves the signal bandwidth which gives $dB_1 = -B_1^2/c_{0a}dR_1 = \beta_{na}\kappa_{0a}k_{00}R_{10}p_0(r)B_1^2\,dr/c_{0a}$. This analysis gives the following differential equations for $f_1$ and $B_1$ $$\frac{df_1}{dr} = \beta_{na}\kappa_{0a}k_{00}\lambda_{10}p_0(r)\frac{f_1^2}{c_{0a}} - 0.36B_1^2(r)\alpha(r) \quad \text{a)} \quad (35)$$

$$\frac{dB_1}{dr} = \beta_{na}\kappa_{0a}k_{00}R_{10}p_0(r)\frac{B_1^2}{c_{0a}} \quad \text{b)}$$

Eq. (35b) can be integrated directly, which allows us to estimate the local absorption coefficient from the measured nonlinear propagation delay $\tau(r)$, its gradient, and the gradient of the center high frequency $f_1(r)$ as $$\alpha(r) = -\frac{1}{0.36B_1^2(r)}\left(k_{00}\lambda_{10}f_1^2\frac{d\tau}{dr} + \frac{df_1}{dr}\right) \quad \text{a)} \quad (36)$$

$$B_1(r) = \frac{B_{10}}{1 - k_{00}R_{10}B_{10}\tau(r)} = \frac{B_{10}}{1 - \omega_0\tau(r)} \quad \text{b)}$$

where $\tau(r)$ is given in Eq. (10) and we have used that $d\tau/dr = -\beta_{na}(r)\kappa_{0a}(r)p_0(r)/c_{0a}(r)$ and that $R_{10}B_{10}=c_{0a}(0)$, and $k_{00}c_{0a}(0)=\omega_0$, the angular center frequency of the low frequency pulse. By adjusting the amplitude of the low frequency pulse one can avoid that the received high frequency signal is modified by the edges of the high frequency receive band so that Eq. (35b) is valid which allows the integration to Eq. (36b) which further allows the estimation of □(r) from Eqs. (35a,36a).

The nonlinear parameter $\beta_n$ becomes very low for hard materials as does the compressibility κ. Therefore, in particular, at interfaces between soft and harder materials, for example tissues with high density of connective fiber molecules, calcifications, or other high density materials, the nonlinear scattering becomes strong. Similarly do one get strong nonlinear scattering at interfaces to softer materials such as fat, foam cells, and especially micro gas bubbles in the tissue where the nonlinear scattering is further enhanced as described below. The same is true for the interface between hard rock and fluid or gas in geological structures, swim bladder of fish or lungs of sea animals in water, mines in soil or on a soft sea bed, etc. The nonlinear imaging hence enhances the visualization of such structures. The invention is therefore useful to visualize micro-calcifications in soft tissue, for example for imaging of tumors in the breast and other tissues, or atherosclerotic plaque, which is difficult to visualize with current acoustic imaging methods. Also, with less dramatic changes in material compressibility, as the compliance decrease with in-growth of connective tissue, or compliance increase with in-growth of fat or foam cells, the nonlinear parameters estimated with these methods give increased image contrast for the tissue changes, compared to current imaging. The image parameters in Eqs. (27,30) then allows for quantitative assessment of the tissue changes.

For gas bubbles, either found naturally in the object as hydrocarbon gas or diver decompression bubbles, or injected into the object as ultrasound contrast agent, the bubble scattering dynamics is described by a differential equation, providing a resonant scattering with a frequency dependent phase lag between the incident and the scattered wave, contrary to scattering from fluid or solid objects where the frequency variation of this phase lag is very low. The low frequency pulse manipulates the micro-bubble diameter (small diameter with positive $p_0$, and large diameter with negative $p_0$), and hence the micro-bubble resonance frequency. This manipulates the phase lag of the scattered signal for the high frequency pulse, in addition to the amplitude of the scattered signal. The manipulation is particularly strong for high frequency pulses in the neighborhood of the micro-bubble resonance frequency as described in U.S. patent application Ser. No. 10/851,820 filed May 21, 2004.

The corrected nonlinear signal $z_{nc}(t)$ for example according to Eq. (19) then contains close to all of the high frequency scattered power from the contrast agent bubbles (both linear and nonlinear components). For a scattering object that contains micro gas bubbles, the present invention therefore significantly increases the CNR (Contrast to Noise Ratio) relative to existing methods of imaging of such bubbles by extracting close to the total scattered high frequency signal power from the micro-bubbles, in particular the strong linear components and not only nonlinear components. Corrections for the low frequency pulse switching of the nonlinear propagation delays provide a suppression of the linearly scattered power from the object providing a large COR (Contrast to Object Ratio). The method hence separates nonlinear forward propagation effects from local, nonlinear scattering and utilizes the local manipulation of the frequency variation of the phase of the scattered signal from gas bubbles to obtain strong, local signal from gas bubbles with strong suppression of the local object signal.

This is different from current methods of contrast agent imaging, where the nonlinear propagation produces an accumulated effect on the forward propagating pulse that also enhances the linear scattering from the tissue in the detection process, so that this linear signal from tissue masks the signal from micro-bubbles (and also the nonlinearly scattered signal from the tissue). Similar effects are found with detection of gas bubbles past a cloud of gas bubbles in geologic structures, and objects past a school of fish with swim bladders or sea animals with lungs.

When the pulse passes through a cloud of gas bubbles (also swim bladders), these will provide increased, accumulative nonlinear propagation lag on the forward propagating pulse, and also nonlinear variation in the pulse amplitude, a phenomenon that increases the need to correct for the nonlinear propagation delays and variations in pulse amplitude to obtain good suppression of the linearly scattered object signal beyond the cloud. The current invention therefore has strong advantages above known methods of micro-bubble imaging. For example, with harmonic imaging the increased, accumulative harmonic distortion for a pulse that passes through a cloud of micro-bubbles is found as strong harmonic components in the linear scattering from tissue beyond the cloud. This for example can provide strong harmonic scattering from the myocardium for a pulse that has passed through a cloud of contrast agent in the ventricle, masking the scattered signal from contrast agent micro-bubbles in the myocardium. This effect can falsely indicate blood perfusion in a region of myocardium with very low or no perfusion, and also indicate gas in a geological structure without gas. With the current method, the effect of a cloud of micro-bubbles in the ventricle on the forward propagating pulse is removed for scattering from the myocardium past the cloud by the corrections for the nonlinear propagation delays. The invention separates the local nonlinear scattering from the accumulative nonlinear forward propagation effect, and hence safeguards that one measures the local nonlinear scattering that greatly prevents such false indications of non-existing micro-bubbles in the myocardium.

Relative to nonlinear harmonic imaging methods, the present invention can use a more broadband transmit pulse and will hence achieve a higher image range resolution. In addition, a higher imaging frequency can be used, resulting in a significant increase in both lateral and range resolution relative to other methods of imaging gas bubbles. The performance of the present invention is less sensitive to the amplitude of the imaging pulses compared to harmonic imaging methods. Together with the indicated suppression of received linearly scattered signal with resulting increase in COR, this facilitates high resolution non-destructive detection and imaging of single contrast agent bubbles with low Mechanical Index (MI).

In medical applications, the improved sensitivity and high resolution imaging of ultrasound contrast agent has strong potentials in imaging of changes in micro-vasculature, for example neo-angiogenesis or necrosis in tumors, or reduced blood perfusion in the myocardium where some standard methods of using inflow time of contrast agent has been developed. The quantitative parameters in Eqs. (27,30) provide quantitative information on the contrast agent density in the tissue, and hence provide an improved assessment of the relative volume of the micro vasculature. The methods also have applications to estimation of relative gas volume in geological structures, and density and size of fish with swim bladder or sea animals with lungs. By destroying the contrast agent bubbles in a region and measuring the inflow time, one can obtain quantitative values for blood perfusion through the tissue, according to known principles. The high sensitivity, high resolution imaging of contrast agent is also useful for tracing of lymphatic drainage to find sentinel lymph nodes in tumor surgery.

As Eqs. (27,30) give imaging parameters that do not depend on absorption in the object, one can use these object parameters to characterize the object (for example fat or connective tissue content in soft tissue, content of oil, gas or water in porous rock, or amount and size of fish and sea animals). In addition one can determine the local variation of the propagation velocity with temperature based on experiments to monitor changes in tissue temperature with thermal treatment of diseased tissue, for example high intensity focused ultrasound (HIFU), RF ablation, or cryo-surgery. The temperature can be monitored from changes in the quantitative parameters, but also from changes in the propagation velocity which causes time lags between the back scattered signals from image to image as the temperature is changing. Radial gradients in this time lag determines the local temperature.

As the local linear scattering of the high frequency pulse is not influenced by the low frequency pulse, it is implied that variations of the amplitude and/or the phase and/or frequency of the low frequency components between transmitted pulses other than that shown in FIG. 3, can give a similar result in suppressing the near source pulse reverberations to obtain a linearly scattered signal with reduced reverberation noise, and suppression of the linear back-scattering to obtain the nonlinearly scattered signal, as above. For example, the low frequency part of the $2^{nd}$ pulse in FIG. 3*b* could be missing, or the high frequency pulses do not have to ride on the exact positive crest or negative trough of the low frequency pulses. This flexibility is important because the phase between the two frequency pulses can due to diffraction and misalignment of radiation surfaces of the transducer arrays for the low and the high frequency components vary with the propagation distance along the beam.

The low and the high frequency bands of the transmitted pulses are often so widely separated that one can prefer to use separate transducer arrays to transmit the two bands of the pulse. Such arrays can be made as concentric rings with different resonant frequencies, where the beams from the arrays automatically overlap, or the arrays can be mounted by the side of each other with skewed crossings of the beams.

Figure 8A:
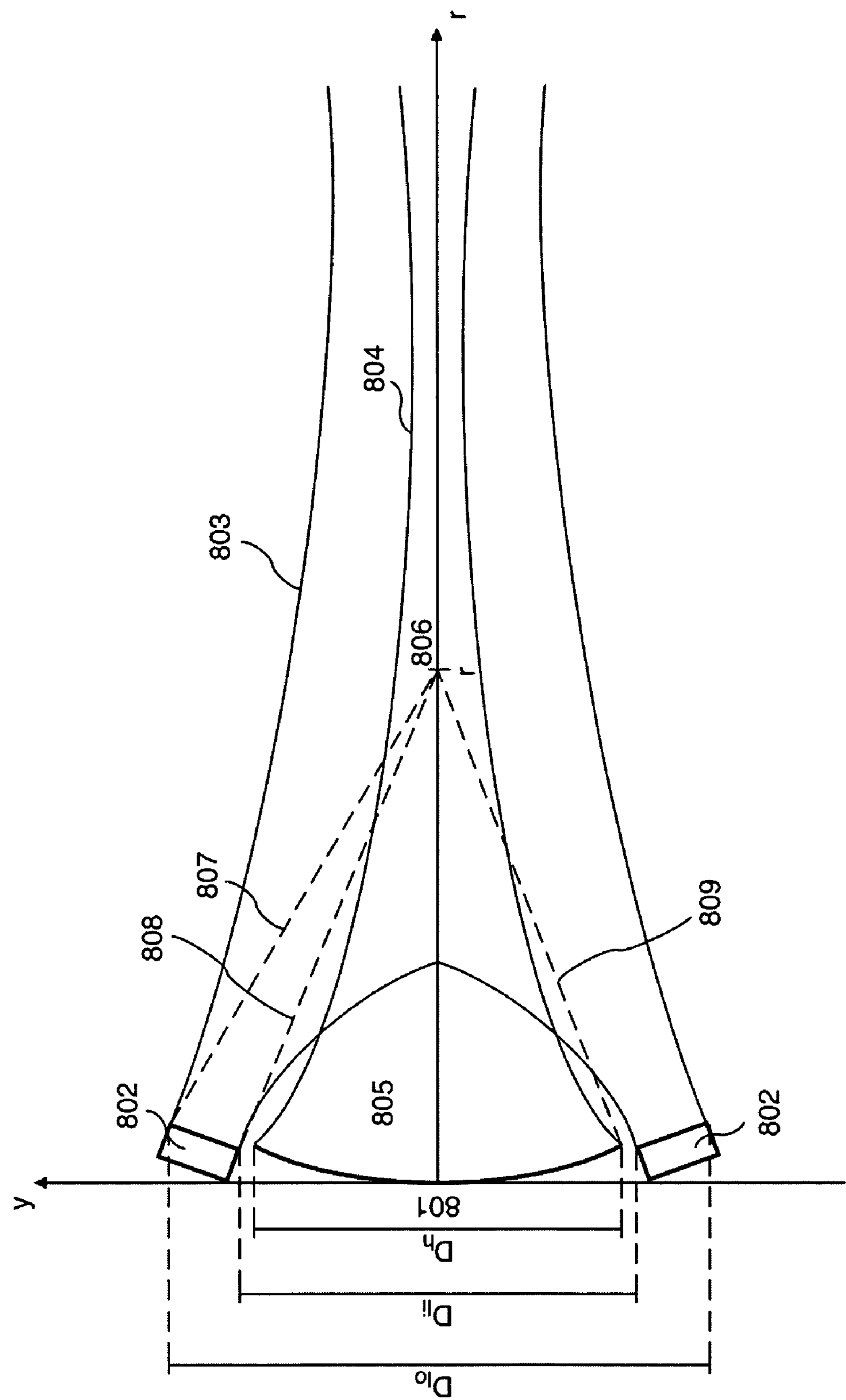
FIG. 8 shows a transducer array assembly for transmission of the low and high frequency components.

When we use two different arrays for the low and the high frequency components, with beams that overlap in a skewed direction, the phase relationship between the low and the high frequency pulses can have a strong spatial dependency, depending on the geometric arrangement and the dimensions of the two radiating array surfaces. An example arrangement according to the invention of separate low and high frequency transducer arrays radiating along the z-axis is shown in FIG. 8*a*, where 801 shows the high frequency array and 802 shows the low frequency array composed of two parts on each side of the high frequency array. The Figure can for example show a cross section through a linear or curvilinear array arrangement where the y-axis is the elevation direction, normal to the azimuth scan-plane which is the x-z plane normal to the y-z plane. The Figure can also represent the cross section of an annular array arrangement with the z-axis as the radiation axis, where 801 shows the cross section through the high frequency annular array, and 802 shows the cross section through a low frequency annular element. Both the linear and the annular arrangements exhibit different propagation delays for the low and the high frequency arrays that must be carefully addressed in the array design and signal processing to take full advantage of the basic physical effects behind the invention.

The boundaries of an example low frequency beam are shown as 803, whereas the boundaries of the high frequency beam are indicated as 804. We note that we have a near-region 805 in front of the array where there is limited overlap between the low and the high frequency beams, hence providing particularly strong suppression of the body wall reverberations of the outgoing pulse with the methods described in relation to Eqs. (14,16) and FIG. 7.

Figure 8B:
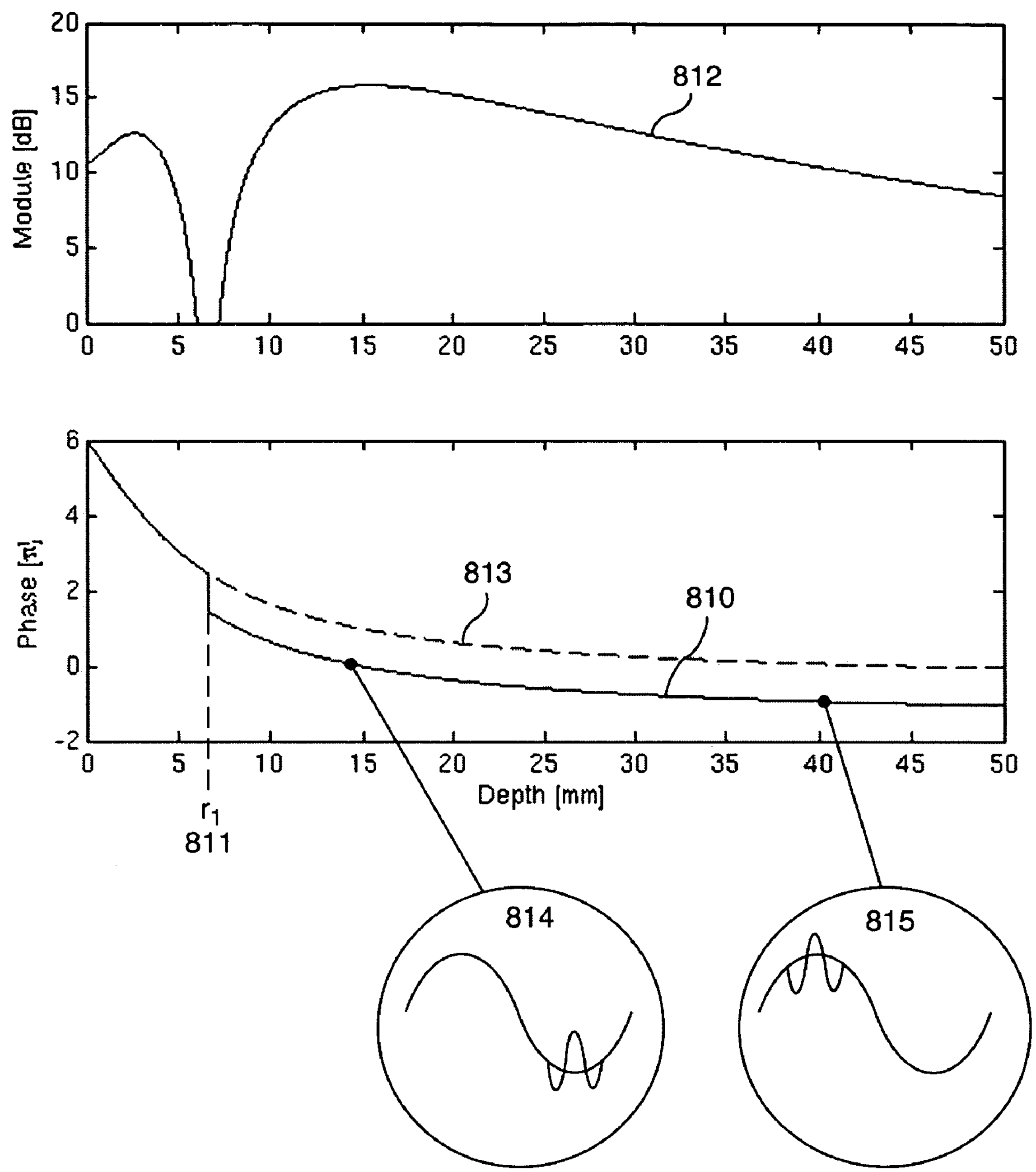
Figure 8C:
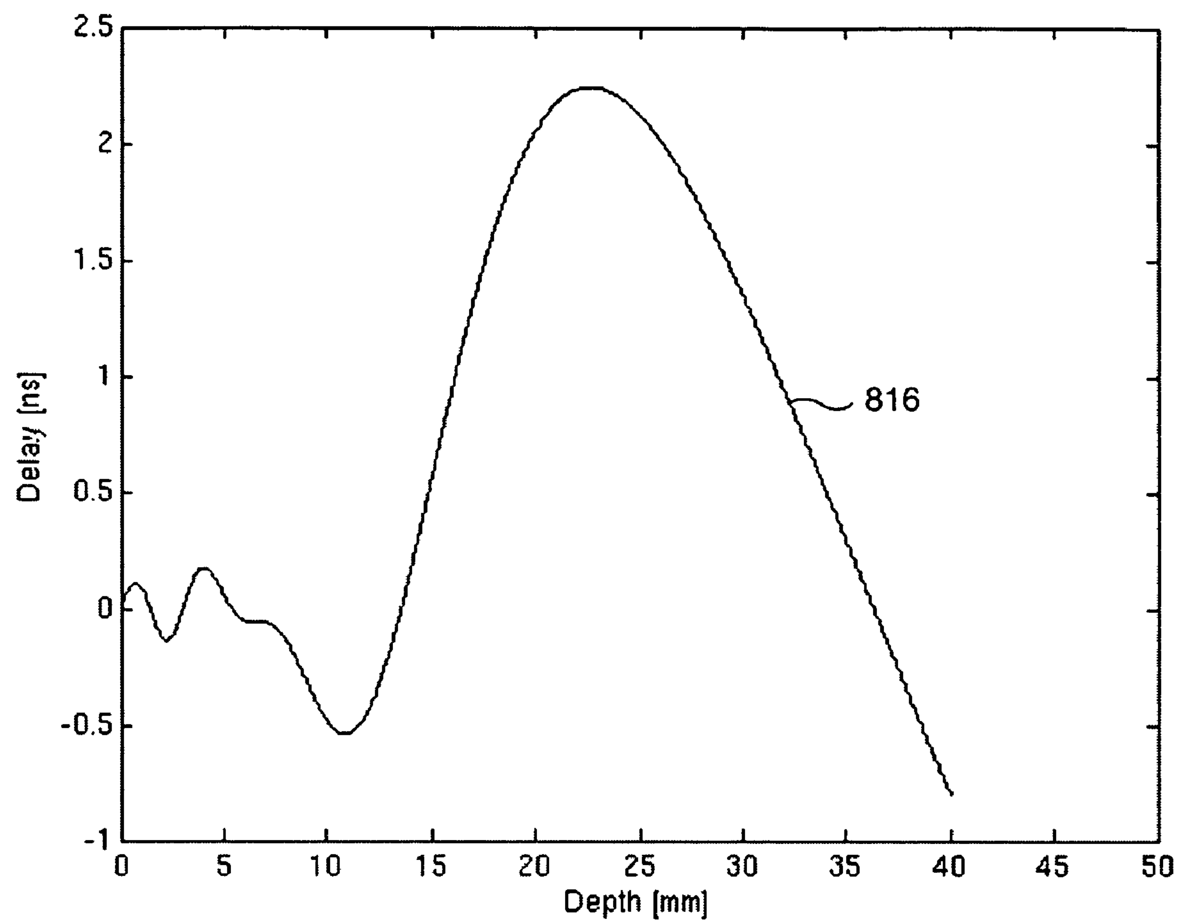

We further note that the propagation distance from the low frequency array to a scatterer close to the z-axis is larger for the low frequency pulse than the high frequency pulse, depending on the geometric dimensions of the low and high frequency arrays. The axial low frequency field at the point 806 at z and angular frequency $\omega_0=ck_0$ is $$\begin{aligned} H_l(z)P_{lt} &= \frac{e^{-ik_0R_{li}(z)} - e^{-ik_0R_{lo}(z)}}{F-z}FP_{lt} \\ &= i2e^{-ik_0(R_{lo}(z)+R_{li}(z))/2}\frac{\sin k_0(R_{lo}(z)-R_{li}(z))/2}{F-z}FP_{lt} \end{aligned} \tag{37}$$

where $P_{lt}$ is the transmit pressure on the array surface, $R_{lo}(z)$ is the distance 807 from the outer edge of the low frequency array to 806 on the z-axis and $R_{li}(z)$ is the distance 808 from the inner edge of the low frequency array to 806. The phase term represents the average propagation lag $$\tau_l(z) = \frac{1}{2c_0}(R_{lo}(z)+R_{li}(z)) \qquad \tau_h(z) = \frac{1}{2c_0}(R_{ho}(z)+z) \tag{38}$$

where $\tau_l(z)$ is the propagation lag from the low frequency array to 806 and $\tau_h(z)$ is the propagation lag from the high frequency array to 806, where $R_{ho}(z)$ is the distance 809 from the outer edge of the high frequency array to 806. In addition to the propagation phase lag, one will encounter changes in the sign of the sine term in Eq. (37) as part of the phase of $H_l(z)$ and is found as steps of $\pm\pi$ when a zero in the sine term is passed. As 810 in FIG. 8*b* is shown the difference in phase lag between the low frequency field and the propagation lag of the high frequency field, given as $$\Delta\theta_l(z) = -\angle\{H_l(z)\} - \omega_0\tau_h(z) \tag{39}$$

as a function of z for a typical geometry with a high frequency aperture $D_h=7$ mm, with inner and outer parts of the low frequency aperture $D_{li}=10$ mm and $D_{lo}=15$ mm. A drop in the phase lag of n is found at 811 (z~6.6 mm) as the difference propagation phase $\Delta\theta_l(z)=\omega_0(R_{lo}(z)-R_{li}(z))/2c_0$ between the outer and inner boarders of the low frequency array passes zero, which produces a change from −1 to +1 in the sign of the sin term in Eq. (37). The amplitude of low frequency field $H_l(z)$ is shown in un-scaled log values as 812, and we note that a zero in the amplitude coincides with the $\pi$-shift in the phase. Zeros in the field are found when the difference in the phase propagation lag between the outer and inner edges of the array to the field point is an odd number of $\pi$, with a production of a step $\pi$ in $\Delta\theta_l(z)$.

For comparison is also shown as 813 the difference in phase propagation between the low frequency and the high frequency arrays, given as $$\Delta\phi_l(z) = \omega_0(\tau_l(z) - \tau_h(z)) \tag{40}$$

We note that $\Delta\theta_l(z)$ follows $\Delta\phi_l(z)$ before the $-\pi$ step at 811 and follows with a difference of $\pi$ thereafter. Due to the large and z-dependent propagation phase lag between the low and the high frequency arrays, one will get a z-dependent relative position between the high and low frequency pulses. For example, a high frequency pulse that originally starts at the top ridge of the low frequency pulse shown as 814, slides towards the bottom trough of the low frequency pulse at 815 when the phase lag $\Delta\theta_l(z)$ has changed $\pi$, and so forth.

Inserting a pressure $$p_0(s) = P_{lt}|H_l(s)|\cos\Delta\theta_l(s) \tag{41}$$

into Eq. (10) with $\beta_n=5$, $\kappa_{0a}=400\cdot10^{-12}$ Pa$^{-1}$, and $c_{0a}=1540$ m/s, we get with $P_{lt}=50$ kPa a nonlinear propagation lag shown as 816 shown in FIG. 8*c*. Because the phase lag $\Delta\theta_l(z)$ (810) varies several $\pi$ along the z-axis in FIG. 8*b*, we get a highly oscillatory nonlinear propagation delay in 816 with a maximal delay of $\tau_{max}$=2 nsec. If we do not delay correct for this nonlinear propagation delay, we get a maximal suppression of the linear back scattered signal of 2 $\sin(\omega_l\tau_{max})$~−18 dB for $f_l$=10 MHz.

For imaging of contrast agent, one would generally use higher low frequency pressure $p_0$, say $p_0$~200 kPa, which would give $\tau_{max}$=8 nsec in the above example and reduce the suppression of the linearly scattered high frequency signal by 2 $\sin(\omega_l\tau_{max})$~−6 dB for $f_1$=10 MHz, even with the large sliding of the phase relation between the low and the high frequency components as found in this design example. Hence, an amplitude of 50 kPa for the low frequency pressure is very low, but can provide interesting imaging of contrast agent and other micro gas bubbles in special situations. It is hence possible to enhance contrast agent signal to some degree without corrections for the nonlinear propagation delays, provided the arrays are designed so that an oscillatory variation of the nonlinear propagation delays as in 816 is found. We should note that when the high frequency pulse is close to zero in the low frequency oscillation, the nonlinear scattering and forward propagation effect is low. This effect can be avoided by using different phases between the low and high frequency components in consecutive transmit pulses, which would shift the spatial location where the high frequency pulse is found close to a zero in the low frequency oscillation. Zeros in the amplitude $|H_l(s)|$ of the low frequency field can be shifted in space by changes the low frequency center between consecutive transmit pulses. Also, due to the width of the high frequency beam, one will also pick up signal from outside the axis where $|H_l|\neq 0$, and the pulse is composed of a frequency band which averages zero points for many frequencies. The amplitude zeros can be avoided by reducing the width of the low frequency array, which would however also lower the pressure amplitude to drive voltage ratio for the array.

However, to extract nonlinear scattering from other objects, like from micro-calcifications in soft tissue and gas in porous rock, and produce quantitative object parameters, it is necessary to use higher low frequency amplitudes, where it becomes mandatory to correct for the nonlinear propagation delays in order to suppress the linear scattering and extract the nonlinear scattering. This is also the case for utilizing the method to suppress pulse reverberation noise as discussed in relation to FIG. 7. Also, with less oscillatory variation of the nonlinear propagation delays one have strong benefits of correcting for the delays for detecting micro gas bubbles even with low amplitude of the low frequency pulse.

Often one would select a design of the low and high frequency radiation apertures so that one gets minimal delay sliding between the low and high frequency pulses, to maximize the nonlinear manipulation of the scattering and propagation parameters for the high frequency pulse along the whole image range. This is necessary to produce a monotone increase of the nonlinear propagation delay as shown in FIG. 4. To avoid the $\pi$-shift of the phase in 810 (and corresponding zero in the amplitude) one must use smaller width of the low frequency elements (i.e. less difference between $R_{lo}$ and $R_{li}$), and to further reduce the sliding in the phase between the low and the high frequency pulses, one must pull the low frequency radiation surface as close to and possibly also overlapping the high frequency radiation surface. However, for many applications one can live with an oscillatory behavior of the nonlinear propagation delays and even utilize it to get low nonlinear propagation delays as in FIG. 7*c*, or shift from pulse length compression for the near to mid field to a pulse length expansion for deep ranges to lower the frequency and improve sensitivity as discussed in relation to FIG. 2.

To reduce the effect of the pulse reverberation noise on the estimation of the corrections for the nonlinear propagation delays, as well as in the nonlinearly scattered signal, one can in a 3rd method according to the invention transmit more than two pulses with more than two different amplitudes and/or phases and/or frequencies of the low frequency pulse. As a first example according to the invention where there is no movement between the scatterers and the transducer array (i.e. zero Doppler displacement), we for example transmit low frequency pulses with amplitudes $+p_0$, 0, $-p_0$ where the high frequency pulse follows close to the peak or trough of the low frequency pulse as for example shown in FIGS. 3*a* and 3*b*. The received high frequency signals from the three pulses can then in interval $T_i$ be written as $$y_1(t)=x_l(t+\tau_i)+x_n(t+\tau_i)+r(t)$$

$$y_2(t)=x_l(t)+r(t)$$

$$y_3(t)=x_l(t-\tau_i)-x_n(t-\tau_i)+r(t) \tag{42}$$

where $x_l(t)$ is the linearly scattered signal, $x_n(t)$ is the nonlinearly scattered signal with amplitude $+p_0$ of the low frequency pulse, r(t) is the reverberation signal for the high frequency pulse, and $-\tau_i$ is the nonlinear propagation delay for the high frequency pulse when it propagates on the positive ridge with pressure $+p_0$ of the low frequency pulse. With one embodiment according to the invention, we form combinations of these three signals as $$z_1(t)=y_2(t)-y_1(t)=x_L(t,\tau_i)-x_n(t+\tau_i)$$

$$z_2(t)=y_3(t)-y_2(t)=x_L(t-\tau_i,\tau_i)-x_n(t-\tau_i) \tag{43}$$

where $x_L(t,\tau_i)=x_l(t)-x_l(t+\tau_i)$ is a combination of the linearly scattered signals. The combinations have removed the pulse reverberation noise from $z_1(t)$ and $z_2(t)$, and as the amplitude of the nonlinearly scattered signal is much lower than for the linearly scattered signal, we have approximately $z_2(t)=z_1(t-\tau_i)$, and we can for the interval $T_i$ determine the delay correction $\tau_i$ by maximizing the following functional $$J_i=\int_{T_i} dt\,|z_1(t-\tau_i)+z_2(t)|^2 \tag{44}$$

with respect to $\tau_i$.

When $\tau_i$ is estimated, we can solve the linear and the nonlinear scattering signal components from Eq. (43), for example through Fourier transforming Eq. (43) in the fast time that produces a set of linear equations in $X_L(\omega)$ and $X_n(\omega)$.

The essence of the above procedure is that three or more pulses with three or more levels of manipulation of the nonlinear propagation delay allows us to combine the measurements to provide at least two signals where the pulse reverberation noise is highly suppressed, and these new signal can be used for estimation of the delay corrections. With the procedure as described, the difference between the amplitudes of neighboring low frequency pulses must be constant, giving a nonlinear propagation delay for each signal that is a whole multiple of one delay. With a constant radial movement between the transducer array and the scatterers that produces a constant Doppler delay between the received signals for each pulse, we have a fourth unknown to estimate, which requires that we transmit at least four pulses with different amplitudes of the low frequency pulse, or one can use 5 pulses with the 3 amplitudes of the low frequency pulse as in Eq. (42), where by maximization of a signal power in the same way as in Eqs. (21,44) we estimate combined nonlinear propagation and Doppler delays. The nonlinear propagation and Doppler delays can then be separated in operations like in Eqs. (24,25) where the details to such and similar procedures can be worked out according to the invention by anyone skilled in the art.

However, $\tau_i$ itself must be estimated from combinations like Eq. (44), or the equivalent in the Fourier transform, and as $z_1$ and $z_2$ contains both the linear and the nonlinear scattering signal, the nonlinear scattering signal will introduce an error in the delay correction estimate, albeit very low, that in turn introduces an error in estimation of the nonlinear scattering signal, in the same way as the estimations given in Eqs. (17-22).

The fundamental reason for this error is that we for stationary objects have four unknowns: The linear scattering $x_l(t)$, the nonlinear scattering $x_n(t)$, the pulse reverberation noise r(t) and the nonlinear forward propagation delay $\tau(t)$ (Stationary object with no Doppler delay). As $\tau(t)$ has a slow variation with t, we can approximate it as constant over the time interval $T_i$ as above. For most accurate estimation of all four unknown, one should have at least 4 measurements, for example with the four levels $+p_0$, $+p_0/3$, $-p_0/3$, $-p_0$ of the low frequency pulse to give $$\begin{aligned} y_1(t) &= x_l(t+\tau_i) + x_n(t+\tau_i) + r(t) \\ y_2(t) &= x_l(t+\tau_i/3) + \frac{1}{3}x_n(t+\tau_i/3) + r(t) \\ y_3(t) &= x_l(t-\tau_i/3) - \frac{1}{3}x_n(t-\tau_i/3) + r(t) \\ y_4(t) &= x_l(t-\tau_i) - x_n(t-\tau_i) + r(t) \end{aligned} \quad (45)$$

One could then eliminate r(t) as in Eq. (43) to produce 3 signals $z_1(t)$, $z_2(t)$, and $z_3(t)$, and determine $\tau_i$ to align all these signals with maximization of a functional similar to Eq. (44). The influence of $x_n(t)$ in the estimate of $\tau_i$ will be lower than with 3 measurements, but the error it introduces is not completely eliminated.

A better approach according to a $4^{th}$ method of the invention, that decouples the influence of $x_n(t)$ on the determination of $\tau_i$ is found through the Fourier transform of Eq. (45) over the interval $T_i$ where $\tau(t)$ can be approximated by the constant $\tau_i$, which gives an over-determined set of linear Equations of the form $$\underline{Y}(\omega)=A(\omega\tau_i)\underline{X}(\omega) \quad (46)$$

where $\underline{Y}(\omega)^T=\{Y_1(\omega), Y_2(\omega), Y_3(\omega), Y_4(\omega)\}$, $\underline{X}(\omega)^T=\{X_l(\omega), X_n(\omega), R(\omega)\}$, and $A(\omega\tau_i)$ is a 4×3 dimensional matrix obtained from the Fourier transform of Eq. (43) according to known methods. With such an over-determined system, one can find the $\underline{X}(\omega)$ that provides the best approximation in the least square sense using the pseudo-inverse of the matrix $A(\omega\tau_i)$ as $$\underline{\tilde{X}}(\omega)=(A^HA)^{-1}A^H\underline{Y}(\omega) \quad (47)$$

where $A^H(\omega\tau_i)$ is the Hermittian transpose of $A(\omega\tau_i)$. $\tau_i$ can now be estimated from a minimization of the error in the least square adaptation $$\begin{aligned} \delta\underline{Y}(\omega) &= \underline{Y} - A(\omega\tau_i)\underline{\tilde{X}}(\omega) \\ &= \left(I - A(\omega\tau_i)(A^H(\omega\tau_i)A(\omega\tau_i))^{-1}A^H(\omega\tau_i)\right)\underline{Y}(\omega) \end{aligned} \quad (48)$$

with respect to $\tau_i$, a process often referred to as total least squares. This method provides a systematic procedure to utilize at least four measurements with at least four different levels of the low frequency pulse to estimate all the four unknowns, especially the nonlinear propagation lag, with highly reduced influence from pulse reverberations and the nonlinear signal, while in many situations the methods described in relation to Eqs. (17-22 and 42-45) provide adequate results. We also note that the amplitude of the low frequency pulses can be set arbitrary so that the nonlinear delays for the different pulses can be set as $\tau_i=k_i\tau$, where $k_i$ is ratio of the low frequency amplitudes to a reference and t is the nonlinear propagation delay with this reference that is estimated according to the procedure above.

We also emphasize that methods according to this structure provide estimates of the linearly and nonlinearly scattered signals (and also the pulse reverberation noise) with minimal influence from the pulse reverberation noise and in principle full decoupling between the linearly and nonlinearly scattered signal estimates. With this method one will hence use the estimated $x_l(t)$ to represent the $1^{st}$ imaging signal of linear scattering with strong suppression of the pulse reverberation noise as Eq. (14) with the $2^{nd}$ method, and the $3^{rd}$ imaging signal of the linear scattering as in Eq. (29), while the estimated $x_n(t)$ represents the $2^{nd}$ image signal from nonlinear sacttering as in Eqs. (19,28), and both are further used in the calculation of the $2^{nd}$ quantitative nonlinear scattering parameter in Eq. (30), where the estimated nonlinear delay t is used for estimation of the $1^{st}$ quantitative nonlinear parameter in Eq. (27).

We can as for the previous methods add a constant Doppler delay $\tau_d$ between the received signals for each transmitted pulse complex, which also gives us 5 unknown as $X_l(\omega)$, $X_n(\omega)$, $R(\omega)$, $\tau$, and $\tau_d$. These can be estimated from the received signals from 5 transmitted pulse complexes, for example with the amplitudes ($+p_0$, $+p_0/2$, 0, $-p_0/2$, $-p_0$) of low frequency pulses and the same amplitude of the high frequency pulse by minimization $\delta\underline{Y}$ in Eq. (48) with.

The above discussion then gives a general outline on how to handle even more complex situations that produces more unknowns to be estimated. For example, we can have uncertainties in the amplitudes of the transmitted low frequency pulses, for example as $+p_0$, $+a_1p_0/3$, $-a_2p_0/3$, $-a_3p_0$ for Eq. (45) where the vector $\underline{a}=(a_1, a_2, a_3)$ represents unknown variations in the amplitudes. These uncertainties will both influence the amplitude of the nonlinear scattering and the delays in Eq. (45) and we see that we get 7 unknowns, i.e. $X_l(\omega)$, $X_n(\omega)$, $R(\omega)$, $\tau$, $a_1$, $a_2$, and $a_3$ which means that we have too few measurement equations for adequate determination of $\tau$ in the minimization of $\delta\underline{Y}$ in Eq. (48). We therefore must add new measurements with careful instrumentation so that the number of amplitude uncertainties is minimized. For example one can with careful instrumentation possibly have only one uncertain amplitude a with 5 transmit pulses and amplitudes of the low frequency pulse as ($+p_0$, $+ap_0/2$, 0, $-ap_0/2$, $-p_0$) which gives 5 unknowns $X_l(\omega)$, $X_n(\omega)$, $R(\omega)$, $\tau$, a, i.e. the same number as equations where a minimization of $\delta\underline{Y}$ in Eq. (48) will provide all 5 unknowns with no Doppler delay.

One should note that the $3^{rd}$ and $4^{th}$ method could as well as the $1^{st}$ and $2^{nd}$ method use the $2^{nd}$ harmonic band of the received signal for the processing and image signal formation, with the advantage of even better suppression of the pulse reverberation noise in the image signals, but at the cost of less image range for the same image frequencies. The instruments as discussed below therefore have the flexibility to select between the $1^{st}$ and $2^{nd}$ harmonic bands of the received signals for the processing according to this invention.

Figure 9A:
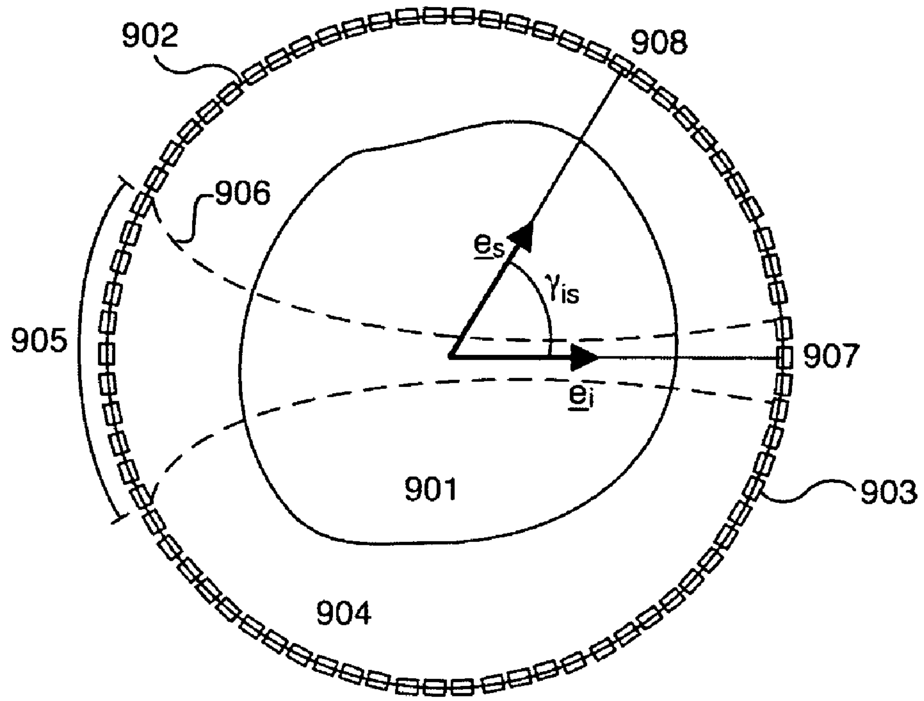
FIG. 9 illustrates a basic transducer array and instrumentation principle for simultaneous measurements of transmission and angular scattering in the object.
Figure 9B:
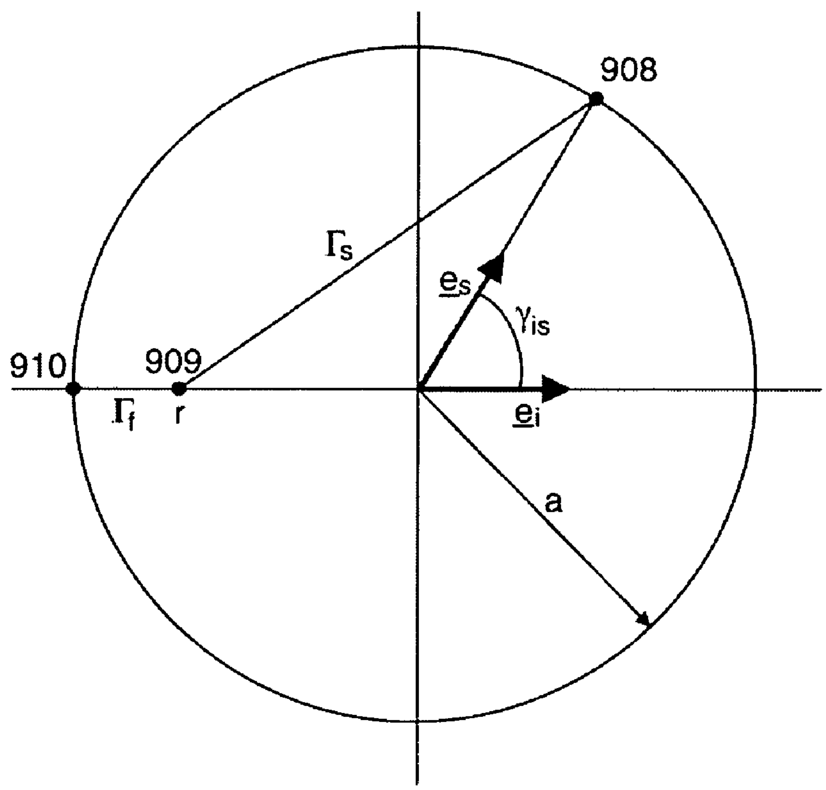

The nonlinear manipulation of the scattering and propagation parameters for the high frequency pulse by the low frequency pulse can produce favorable results also with tomographic computer image reconstruction from transmission and angular scattering measurements of the object, for example with an instrumentation as illustrated in FIG. 9*a*. In this F*igure* 901 shows a cross section of the object, enclosed in a ring acoustic transducer array 902 with transducer elements 903 mounted around the whole object. An intermediate acoustic coupling medium 904 can for example be water or other fluid. A group 905 of elements is freely selected amongst the whole group for transmission of an acoustic beam 906 whose direction through the object, denoted by the unit vector $\underline{e}_i$, can be scanned in all directions through the object by selecting different groups of transmit elements from the whole group of elements. In the forwards direction $\underline{e}_i$ the pulse hits the ring array at 907 with a forward propagation lag which is a modification of Eq. (10) as $$
\begin{aligned}
t_f(\underline{e}_i) &= t_{0f}(\underline{e}_i) + \tau(2a;\underline{e}_i) \\
t_{0f}(\underline{e}_i) &= \int_{\Gamma_f(2a;\underline{e}_i)} \frac{ds}{c_{0a}(s)} \\
\tau(2a;\underline{e}_i) &= -\int_{\Gamma_f(2a;\underline{e}_i)} ds \frac{\beta_{na}(s)\kappa_{0a}(s)p_0(s)}{c_{0a}(s)}
\end{aligned}
\tag{49}
$$

where $\Gamma_f(2a;\underline{e}_i)$ is the forward propagation path along the beam axis across the whole diameter 2a of the array. The propagation delay with zero amplitude of the low frequency pulse is $t_{0f}$ while the nonlinear delay produced by the low frequency pulse is given by $\tau$. The received signal at 907 will first be the transmitted pulse followed by a tail of multiple reflected pulses. However, with reference to FIG. 7, the multiply scattered signal will have a much lower nonlinear time lag $\tau$, and can be heavily suppressed combining at least two received signals with variations in the amplitude and/or phase and/or frequency of the low frequency transmitted pulse along the lines described above. When the high frequency pulse is found at the negative spatial gradient of the low frequency pulse as shown in FIG. 1, the co-propagation of the pulses produces the high frequency pulse compression as discussed in relation to this Figure, and suppression of pulse reverberation noise can then be done with frequency filtering, preferably sliding as discussed in relation to FIG. 2. For deepest penetration, one can design high and low frequency radiation surfaces so that the high frequency pulse location in relation to the low frequency pulse slides to provide a pulse expansion with reduced frequency, as discussed in relation to FIG. 2. Examples of such radiation surfaces with an analysis of the effects that produce sliding is shown in FIG. 7 and its accompanying discussion.

According to the methods of computer tomography reconstruction, one can use the delay without the low frequency pulse, $t_{0f}$, to find the propagation velocity $c_{0a}(\underline{r})$ where r is the spatial coordinate in the plane. Adding a low frequency pulse and measuring the nonlinear propagation lag $\tau$, then allows for reconstruction of $\beta_{na}(\underline{r})\kappa_{0a}(\underline{r})$. Using the amplitude of the forward propagated pulse, one can also reconstruct the spatial variation of the absorption in the object. Moving the scan plane in the vertical direction then allows for 3D imaging of the object. All these reconstructed images will have a spatial resolution limited by the transmitted beam width, as the pulse delay and amplitude is an averaging over the whole beam, whereas the model in Eq. (49) assumes all delays confined to the beam axis. A similar model would be used for the absorption.

Improved resolution can be obtained by also using the angularly scattered signal, in methods referred to as diffraction tomography, reflective tomography, inverse scattering tomography, etc. On elements at an angular direction to the transmitted beam direction, for example 908 in FIG. 9*a,b* defined by the angular direction of the unit vector $\underline{e}_s$ from the array center, one will observe angularly scattered signals as a function of time from different depths along the transmitted beam. The high frequency pulse that is scattered from a depth r at 909 along the transmitted beam will first propagate along the path $\Gamma_f$ shown in FIG. 9*b* from 910 to 909 together with the low frequency pulse with high amplitude, and from 909 to 908 along the path $\Gamma_s$ together with a low frequency pulse of negligible amplitude due to the amplitude reduction in the scattering process. The total propagation time lag from 910 to 908 then gets the form $$
\begin{aligned}
t(r;\underline{e}_i\underline{e}_s) &= t_0(r;\underline{e}_i,\underline{e}_s) + \tau(r;\underline{e}_i) \\
t_0(r;\underline{e}_i,\underline{e}_s) &= \int_{\Gamma_f(r;\underline{e}_i)+\Gamma_s(r;\underline{e}_i,\underline{e}_s)} \frac{ds}{c_{0a}(s)} \\
&\approx \frac{1}{c_{0a}}\left(r + \sqrt{r^2 + 2a(r+a)(1+\underline{e}_i\underline{e}_s)}\right) \\
\tau(r;\underline{e}_i) &= -\int_{\Gamma_f(r;\underline{e}_i)} ds \frac{\beta_{na}(s)\kappa_{0a}(s)p_0(s)}{c_{0a}(s)}
\end{aligned}
\tag{50}
$$

where we in the last expression for $t_0$ has assumed a constant propagation velocity $c_{0a}$ along both $\Gamma_f$ and $\Gamma_s$. As discussed in relation to FIG. 7 the multiply scattered high frequency signal is less influenced by the low frequency pulse, so that by combining two or more high frequency signals with different amplitudes and/or phases and/or frequencies of the low frequency pulse, one can heavily suppress the pulse reverberation noise. Similarly, one can use the frequency sliding of the high frequency pulse by the low frequency pulse as described in relation to FIGS. 1 and 2 to suppress pulse reverberation noise, and one can also use the $2^{nd}$ harmonic band of the received signals in conjunction with methods 1-4 described above to further suppress pulse reverberation noise and the estimate nonlinear scattering signal and quantitative propagation and scattering parameters as a basis for the tomographic image reconstruction. It is also clear to anyone skilled in the art, that other arrangements of the transducer elements than those specific shown in FIG. 9 can be used to obtain the same result of computerized tomographic reconstructions.

The delay corrections that maximizes functionals $J_{1i}$ of the types shown in Eq. (21) and similarly Eq. (44) can (both for the $1^{st}$ and $2^{nd}$ harmonic bands of the received signals and also the complete received signals) for example be found from differentiation illustrated for Eq. (21) as $$
\frac{\partial J_{1i}}{\partial \tau_{ip}} = \sum_k \frac{\partial \hat{R}_{kp}^i(\tau_{ip}-\tau_{ik})}{\partial \tau_{ip}} + \sum_l \frac{\partial \hat{R}_{pl}^i(\tau_{il}-\tau_{ip})}{\partial \tau_{ip}} = 0
\qquad p = 1, \ldots, K-1
\tag{51}
$$

where the total number of delays are K−1 per the discussion in relation to Eq. (17). Due to the Hermittian symmetry of $\hat{R}_{kl}^{i}$, this equation can be modified as $$\frac{\partial J_{1i}}{\partial \tau_{ip}} = 2\mathrm{Re}\sum_{l} \frac{\partial \hat{R}_{pl}^{i}(\tau_{il} - \tau_{ip})}{\partial \tau_{ip}} = 0 \quad p = 1, \ldots, K-1 \tag{52}$$

where Re denotes the real part of the sum. Noting that $\partial x_l(t+\tau_{ip})/\partial \tau_{ip} = \partial x_l(t+\tau_{ip})/\partial t$, we can rearrange Eq. (52) to $$\sum_{i} \frac{\partial \hat{R}_{pl}^{i}(\tau_{il} - \tau_{ip})}{\partial \tau_{ip}} = \int_{T_i} dt \hat{x}_p^*(t+\tau_{ip}) \frac{\partial \hat{Z}_{1i}(t)}{\partial t} \tag{53}$$

where $\hat{z}_{li}(t)$ is the signal in Eq. (17) delay corrected with □$_{ik}$. As we do not have an analytic expression of $\hat{R}_{kl}^{i}$, the delays that satisfy this set of equations must be found numerically, for example through the following iteration scheme $$\tau_{ip,q+1} = \tau_{ip,q} + \mu \int_{T_i} dt \ \mathrm{Re}\left\{\hat{x}_p^*(t+\tau_{ip,q}) \frac{\partial \hat{Z}_{1,i,q}(t)}{\partial t}\right\} \tag{54}$$

$$\hat{z}_{1i,q}(t) = \sum_{k} \hat{x}_k(t+\tau_{ik,q})$$

where q denotes the iteration step-number and μ is a gain factor that is adjusted to assure convergence of the iteration.

The minimization of $J_{ni}$ in Eq. (22) with respect to $h_{ip}$ can be done by equating the derivatives to zero, i.e.

$$\frac{\partial J_{ni}}{\partial h_{ip}} = \sum_{k} h_{ik} \hat{N}_{kp}^{i}(\tau_{ip} - \tau_{ik}) + \sum_{l} h_{il} \hat{N}_{pl}^{i}(\tau_{il} - \tau_{ip}) - 2\lambda_i h_{ip} = 0 \tag{55}$$

Due to the Hermittian symmetry of $\hat{N}$, this equation transformed to the following eigenvector equation $$\sum_{l} \mathrm{Re}\left\{\hat{N}_{pl}^{i}(\tau_{il} - \tau_{ip})\right\} h_{il} = \lambda_i h_{ip} \tag{56}$$

The minimum of $J_{ni}$ is then given by the eigenvector with the smallest eigenvalue $\lambda_i$. Introducing the expression for the correlation matrix in Eq. (22) allows rearrangement of Eq. (56) to $$\lambda_i h_{ip} = (-1)^p \int_{T_i} dt \ \mathrm{Re}\left\{\hat{x}_p^*(t+\tau_{ik}) \hat{z}_{ni}(t)\right\} \tag{57}$$

where $\hat{z}_{ni}(t)$ is the signal in Eq. (19) delay corrected with $\tau_{ik}$. Hence, the correction amplitude is found through correlation between the RF element signals and the delay and amplitude corrected high pass filter output RF signal where $h_{ik}$ is involved. Eq. (57) can then be solved in an iterative procedure, for example as $$\tilde{h}_{ip,q+1} = (-1)^p \int_{T_i} dt \ \mathrm{Re}\left\{\hat{x}_p^*(t+\tau_{ik}) \hat{z}_{ni,q}(t)\right\} \tag{58}$$

$$\hat{z}_{ni,q}(t) = \sum_{k=0}^{K-1} (-1)^k h_{ik,q} \hat{x}_k(t+\tau_{ik})$$

$$h_{ik,q+1} = N \frac{\tilde{h}_{ip,q+1}}{\sum_{k=0}^{K-1} |\tilde{h}_{ik,q+1}|^2}$$

We have in the above analysis used the complex analytic representation of the signal that can be obtained from the received RF signal by the use of the Hilbert transform as in Eq. (11). Approximations of the Hilbert transform is given in Eq. (74). It is also clear to anyone skilled in the art, that the above analysis can be modified to operate on the received RF-signals as the real part of the analytic signal.

For the procedures in Eqs. (54,58) it is natural to start the estimation for the interval $T_0$ at the lowest lag, followed by estimation in consecutive intervals. One then uses the estimated delay corrections $\tau_{ip}$ filter amplitudes $h_{ip}$ for the preceding interval as the initial values in the iteration procedures for each new interval, starting with $\rho_{0p,0}=0$ and $h_{ip}=1$ as initial conditions for the first interval. An added advantage of using the estimated values for the preceding interval as initial conditions, is that when the step in the phase $\omega_1 \delta\tau_{ip}$ associated to the delay is less than $\pm\pi/\omega_1$ between each interval, one is able to track delays with associated phases $|\omega_1 \tau_{ip}| >> \pi$ over the whole depth range.

When the bandwidth of the signals is sufficiently low, and the delays are less than a period of the center frequency, the following approximations are adequate $$\frac{\partial \hat{x}_k(t)}{\partial t} \approx i\omega_1 \hat{x}_k(t) \qquad \text{a)} \tag{59}$$

$$\hat{x}_k(t+\tau_{ik}) \approx e^{i\omega_1 \delta\tau_{ik}} \hat{x}_k(t+\tilde{\tau}_{ik}) \quad \text{b)}$$

where in Eq. (56b) we have split the delay correction as $$\tau_{ik} = \delta\tau_{ik} + \tilde{\tau}_{ik} \tag{60}$$

where $\tilde{\tau}_{ik}$ is an estimate or approximation to $\tau_{ik}$ where we for example below will use $\tilde{\tau}_{i,k} = \tau_{i-1,k}$. Eq. (59b) hence represents a combination of phase delay with the phase $\omega_l \delta\tau_{ik}$, and true delay with $\tilde{\tau}_{ik}$ of the an estimate of $\tau_{ik}$. Improved accuracy of this approximation is obtained by bandpass filtering the signals around □$_1$ to reduce the bandwidth of $\hat{x}_k(t)$. Introducing the approximations of Eqs. (59) modifies Eqs. (53,54) as $$\mathrm{Re}\left\{\int_{T_i} dt \hat{x}_p^*(t+\tau_{ip}) \frac{\partial \hat{z}_{1i}(t)}{\partial t}\right\} \approx -\omega_1 \mathrm{Im}\left\{\int_{T_i} dt \hat{x}_p^*(t+\tau_{ip}) \hat{z}_{1i}(t)\right\} \approx -\omega_1 \mathrm{Im}\left\{e^{-i\omega_1 \delta\tau_{ik}} \int_{T_1} dt \hat{x}_p^*(t+\tilde{\tau}_{ik}) \hat{z}_{1i}(t)\right\} = 0 \tag{61}$$

Equating the last expression to zero, allows us to calculate $\delta\tau_{ip}$ as $$\delta\tau_{ip} = \frac{1}{\omega_1}\angle\left\{\int_{T_i} dt \hat{x}_p^*\left(t+\hat{\tau}_{ik}\right)\hat{z}_{1i}(t)\right\} \tag{62}$$

where $\angle\{\ \}$ denotes the phase angle of the complex expression. This gives the following iterative equation for the amplitude and delay corrections $$\tau_{ip,q+1} = \tau_{ip,q} + \frac{1}{\omega_1}\angle\left\{\int_{T_i} dt \hat{x}_p^*(t+\tau_{ip,q})\hat{z}_{1i,q}(t)\right\} \tag{63}$$
$$\hat{z}_{1i,q}(t) = \sum_k \hat{x}_k(t+\tau_{ik,q})$$

where one would typically start the iteration with $\tau_{ip,0}=\tau_{i-1,p}$ with $\tau_{0p,0}=0$ as initial conditions for the first interval.

With the approximation in Eq. (59), we can develop the maximization of the power in Eqs. (17,21) into an eigenvalue problem. We use the split of the delay as in Eq. (60), which gives $$\begin{aligned} \hat{y}_{1i}(t) &= \sum_k \hat{x}_k(t+\tau_{ik}) \\ &\approx \sum_k e^{i\omega_1\delta\tau_{ik}}\hat{x}_k(t+\tau_{i-1,k}) \\ &= \sum_k s_{ik}\hat{x}_k(t+\tau_{i-1,k}) \\ s_{ik} &= e^{i\omega_1\delta\tau_{ik}} \end{aligned} \tag{64}$$

The functional in Eq. (21) is modified as $$\begin{aligned} J_{1i} &= \int_{T_i} dt\left|\hat{z}_{1i}(t)\right|^2 - \lambda_i\sum_k |s_{ik}|^2 \\ &= \sum_{km} s_{ik}^* s_{im}\hat{R}_{km}^i - \lambda_i\sum_k |s_{ik}|^2 \\ \hat{R}_{km}^i &= \int_{T_i} dt\hat{x}_k^*(t+\tau_{i-1,k})\hat{x}_m(t+\tau_{i-1,m}) \end{aligned} \tag{65}$$

Maximization of $J_{1i}$ with respect to the amplitude and phase of $s_{ik}$, gives $s_{ik}$ as the solution to the following eigenvalue problem $$\hat{R}^i\underline{s}_i=\lambda_i\underline{s}_i\ \hat{R}^i=\{\hat{R}^i_{km}\}\underline{s}_i=\{s_{ik}\} \tag{66}$$

for the largest eigenvalue $\lambda_i$. The maximum of $J_{1i}$ is found by best possible alignment of the component signals so that optimal correction delays are found from the phases of the eigenvector components. The components of the $\underline{s}_i$ vectors defined in Eq. (64) all have unity module, while the components of the eigenvectors in Eq. (66) generally will have modules different from unity because the magnitude of $J_{1i}$ can be further increased by putting different weights on different component signals. The phases of the eigenvector components will then give the delay corrections that maximizes the power in Eqs. (17,64). We note that the matrix $\hat{R}^i$ is Hermittian, i.e. $\hat{R}_{lm}^i=(\hat{R}_{ml}^i)^*$. This implies that the eigenvalues are real, and the eigenvectors form a complete, orthogonal basis for $C_K$, the complex K-dimensional space.

The accuracy of the approximation in Eq. (59) and hence the eigenvector solution in Eq. (66) improves by reducing the bandwidth of the signals. The Fourier transform of the partial sum signals at $\omega_1$ provides so strong band pass filtering that the differentiation in Eq. (59a) and the phase delay in Eq. (59b) becomes exact. However, to avoid that the phase delay exceeds the fundamental range of $\pm\pi$, it is still advantageous to split the delays as in Eq. (60), which gives $$\hat{Z}_{1i}(\omega) = \sum_k e^{-i\omega_1\delta\tau_{ik}}\hat{X}_k(\omega)e^{-i\omega_1\tau_{i-1,k}} = \sum_k s_{ik}\hat{Y}_{ik}(\omega) \tag{67}$$
$$s_{ik} = e^{-i\omega\delta\tau_{ik}} \quad \hat{Y}_{ik}(\omega) = \hat{X}_k(\omega)e^{-i\omega\tau_{i-1,k}}$$

One can then determine the delays by maximizing the functional $$J_{1i} = \left|\hat{Z}_{1i}(\omega)\right|^2 - \lambda_i\sum_k|s_{ik}|^2 = \sum_{km}s_{ik}^*s_{im}\hat{R}_{km}^i - \lambda_i\sum_k|s_{ik}|^2 \tag{68}$$
$$\hat{R}_{km}^i = \hat{Y}_{ik}^*(\omega)\hat{Y}_{im}(\omega)$$

The maximization will lead to an eigenvalue problem for each frequency, similar to Eq. (66), where the delay corrections are found from the phases of $s_{ik}$. As the phase delay for the Fourier transform is an accurate representation of a true delay, Eq. (67) is fully accurate as opposed to Eq. (64) where the phase delay is taken only at the center frequency.

A bulk of the analysis above is based on availability of the complex analytic RF element signals and further processing of this to the corrected receive signal. The calculations can be simplified through the following exercises, where we note that the phase in Eq. (62) can be calculated as $$\delta\tau_{ip} = -\frac{1}{\omega_1}\tan^{-1}\frac{\int_{T_i} dt\left(\mathrm{Re}\{\hat{x}_p(t+\tau_{i-1,p})\}\mathrm{Im}\{\hat{z}_{1i}(t)\} - \mathrm{Im}\{\hat{x}_p(t+\tau_{i-1,p})\}\mathrm{Re}\{\hat{z}_{1i}(t)\}\right)}{\int_{T_i} dt\left(\mathrm{Re}\{\hat{x}_p(t+\tau_{i-1,p})\}\mathrm{Re}\{\hat{z}_{1i}(t)\} + \mathrm{Im}\{\hat{x}_p(t+\tau_{i-1,p})\}\mathrm{Im}\{\hat{z}_{1i}(t)\}\right)} \tag{69}$$

The integration over $T_i$ is an estimate of the following ensemble expectation values $$\int_{T_i} dt A_i(t) \approx T_i\langle A_i\rangle \tag{70}$$

where <•> denotes ensemble averaging, and $A_i(t)$ take the following forms $$A_i(t) = \mathrm{Re}\{\hat{x}_p(t+\tau_{i-1,p})\}\mathrm{Im}\{\hat{z}_{1i}(t)\} \quad A_i(t) = \mathrm{Im}\{\hat{x}_p(t+\tau_{i-1,p})\}\mathrm{Re}\{\hat{z}_{1i}(t)\} \tag{71}$$
$$A_i(t) = \mathrm{Re}\{\hat{x}_p(t+\tau_{i-1,p})\}\mathrm{Re}\{\hat{z}_{1i}(t)\} \quad A_i(t) = \mathrm{Im}\{\hat{x}_p(t+\tau_{i-1,p})\}\mathrm{Im}\{\hat{z}_{1i}(t)\}$$

The approximation in Eq. (70) turns to equality as $T_i\to\infty$ where for finite $T_i$ one will have a random estimation error of the ensemble averages, which is the reason for the approximation sign in Eq. (70). From signal processing textbooks we find that $$\langle \mathrm{Re}\{\hat{x}_p(t+\tau_{i-1,p})\}\mathrm{Im}\{\hat{z}_{1i}(t)\}\rangle = -\langle \mathrm{Im}\{\hat{x}_p(t+\tau_{i-1,p})\}\mathrm{Re}\{\hat{z}_{1i}(t)\}\rangle \quad (72)$$

$$\langle \mathrm{Re}\{\hat{x}_p(t+\tau_{i-1,p})\}\mathrm{Re}\{\hat{z}_{1i}(t)\}\rangle = \langle \mathrm{Im}\{\hat{x}_p(t+\tau_{i-1,p})\}\mathrm{Im}\{\hat{z}_{1i}(t)\}\rangle$$

For finite $T_i$, the random estimation errors produce the following approximations $$\delta\tau_{ip} \approx -\frac{1}{\omega_1}\tan^{-1}\frac{\int_{T_i} dt \mathrm{Re}\{\hat{x}_p(t+\tau_{i-1,p})\}\mathrm{Im}\{\hat{z}_{1i}(t)\}}{\int_{T_i} dt \mathrm{Re}\{\hat{x}_p(t+\tau_{i-1,p})\}\mathrm{Re}\{\hat{z}_{1i}(t)\}} \approx \frac{1}{\omega_1}\tan^{-1}\frac{\int_{T_i} dt \mathrm{Im}\{\hat{x}_p(t+\tau_{i-1,p})\}\mathrm{Re}\{\hat{z}_{1i}(t)\}}{\int_{T_i} dt \mathrm{Re}\{\hat{x}_p(t+\tau_{i-1,p})\}\mathrm{Re}\{\hat{z}_{1i}(t)\}} \quad (73)$$

We further note that $$\mathrm{Re}\{\hat{x}_p(t)\} = x_p(t) \qquad \mathrm{Re}\{\hat{z}_{1i}(t)\} = z_{1i}(t) \quad (74)$$

$$\mathrm{Im}\{\hat{x}_p(t)\} = H\{x_p(t)\} \approx x_p(t-\pi/2\omega_1) \qquad \mathrm{Im}\{\hat{z}_{1i}(t)\} = H\{z_{1i}(t)\} \approx z_{1i}(t-\pi/2\omega_1)$$

where the approximation of the Hilbert transform through delaying the signals $\pi/2\omega_1$ is adequate for narrow band signals centered at $\omega_1$. Combining Eqs. (73,74) we get the simplified expressions $$\delta\tau_{ip} \approx -\frac{1}{\omega_1}\tan^{-1}\frac{\int_{T_i} dt\, x_p(t+\tau_{i-1,p})H\{z_{1i}(t)\}}{\int_{T_i} dt\, x_p(t+\tau_{i-1,p})z_{1i}(t)} \approx -\frac{1}{\omega_1}\tan^{-1}\frac{\int_{T_i} dt\, x_p(t+\tau_{i-1,p})z_{1i}(t-\pi/2\omega_1)}{\int_{T_i} dt\, x_p(t+\tau_{i-1,p})z_{1i}(t)} \quad (75)$$

In this expression, the Hilbert transform or its delay approximation operates only on the corrected high-pass filter output, and hence only have to be done on one signal, simplifying the operations. A similar expression could be developed from the last part of Eq. (73), but there the Hilbert transform or its delay approximation must be done on received signals $x_p(t)$, which requires more processing. Some reduction in estimation variance can be obtained by combining the first and last expression in Eq. (73) along the lines of Eq. (69).

We also note the following relations $$\langle \mathrm{Re}\{\hat{x}_p(t)\}\mathrm{Im}\{\hat{z}_{1i}(t)\}\rangle = \langle \mathrm{Re}\{\tilde{x}_p(t)\}\mathrm{Im}\{\tilde{z}_i(t)\}\rangle = -\langle \mathrm{Im}\{\tilde{x}_p(t)\}\mathrm{Re}\{\tilde{z}_{1i}(t)\}\rangle \quad (76)$$

which allows that the above operations on the analytic signal can be substituted by operations on the complex envelope, where its real and imaginary parts are found as the in phase and the quadrature components of standard quadrature demodulator output signals as described above.

With a continuous, mechanical sweep of the acoustic beam it is also interesting to use Infinite Impulse Response (IIR) low-pass and high-pass filters, where an example 1$^{st}$ order lowpass filter can be described as $$z_{ik}(t) = \varphi_1 z_{i,k-1}(t) + \varphi_2 x_k(t+\tau_{ik}) \quad (77)$$

$$\varphi_1 = \frac{T}{T+T_{prf}} \qquad \varphi_2 = \frac{T_{prf}}{T+T_{prf}}$$

where T is the filter time constant with cut-off frequency $\omega_c=1/T$, the subscript k denotes the pulse number as before, and the image signal $z_{ik}(t)$ is updated for each new transmit pulse. The same equation structure holds for the analytic signal and its complex envelope.

A recursive scheme of estimation of the correction delays $\tau_{ik}$ for each new transmitted beam is now developed. We assume that $\tau_{im}$ are given for m up to k−1. With the new transmitted beam no k with the received signal $x_k(t)$ one then wants to estimate the delay corrections $\tau_{ik}$. This estimation is then typically done through minimizing the functional where we have used the analytic signal approximation for simplicity $$J_i = \int_{T_i} dt\, \hat{z}_{ik}^*(t)\hat{z}_{ik}(t) \quad (78)$$

Differentiation with respect to $\tau_{ik}$ gives $$\frac{\partial J_i}{\partial \tau_{ik}} = 2\varphi_2 \mathrm{Re}\left\{\int_{T_i} dt \frac{\partial \hat{x}_k^*(t+\tau_{ik})}{\partial \tau_{ik}}\hat{z}_{ik}(t)\right\} = 0 \quad (79)$$

Inserting the approximation in Eq. (59) we get $$\frac{\partial J_i}{\partial \tau_{ik}} = -2\varphi_2\omega_1 \mathrm{Im}\int_{T_i} dt e^{-i\omega_1\delta\tau_{ik}}\hat{x}_k^*(t+\tau_{i-1,k})\left(\varphi_1\hat{z}_{i,k-1}(t) + \varphi_2\hat{x}_k(t+\tau_{i,k})\right) = -2\varphi_2\omega_1 \mathrm{Im}\int_{T_i} dt\left\{\varphi_1 e^{-i\omega_1\delta\tau_{ik}}\hat{x}_k^*(t+\tau_{i-1,k})\hat{z}_{i,k-1}(t) + \varphi_2|\hat{x}_k(t+\tau_{i-1,k})|^2\right\} = 0 \quad (80)$$

As the last term under the integral is real, equality of the above expression is found when $$\delta\tau_{ik} = \frac{1}{\omega_1}\angle\left\{\int_{T_i} dt\hat{x}_k^*(t+\tau_{i-1,k})\hat{z}_{i,k-1}(t)\right\} \quad (81)$$

Higher order high pass filters can be described in a similar fashion with a vector state space representation of the filters known to anyone skilled in the art. A recursive estimation of $\tau_{ik}$ along the lines shown above can then be done by anyone skilled in the art.

For adequate suppression of the linearly scattered signal, one needs a delay accuracy that is much lower than the sampling interval of the received RF signal in most acoustic imaging system. This accuracy can be obtained through interpolation of the signal between the samples according to known methods. Less, but often adequate accuracy can be obtained by a combination of delay correction with the accuracy of the nearest sample $$t + \breve{\tau}_{ik},$$

and a phase correction $\omega_l\delta\tau_{ik}$ in analogy with Eq. (59) as $$\hat{x}_k(t+\tau_{ik}) \approx e^{i\omega_1\delta\hat{\tau}_{ik}}\hat{x}_k(t+\tau_{ik}) \tag{82}$$

where $\delta\tau_{ik}=\tau_{ik}-\hat{t}_{ik}$. The RF-signal is the real part of Eq. (82).

Figure 10:
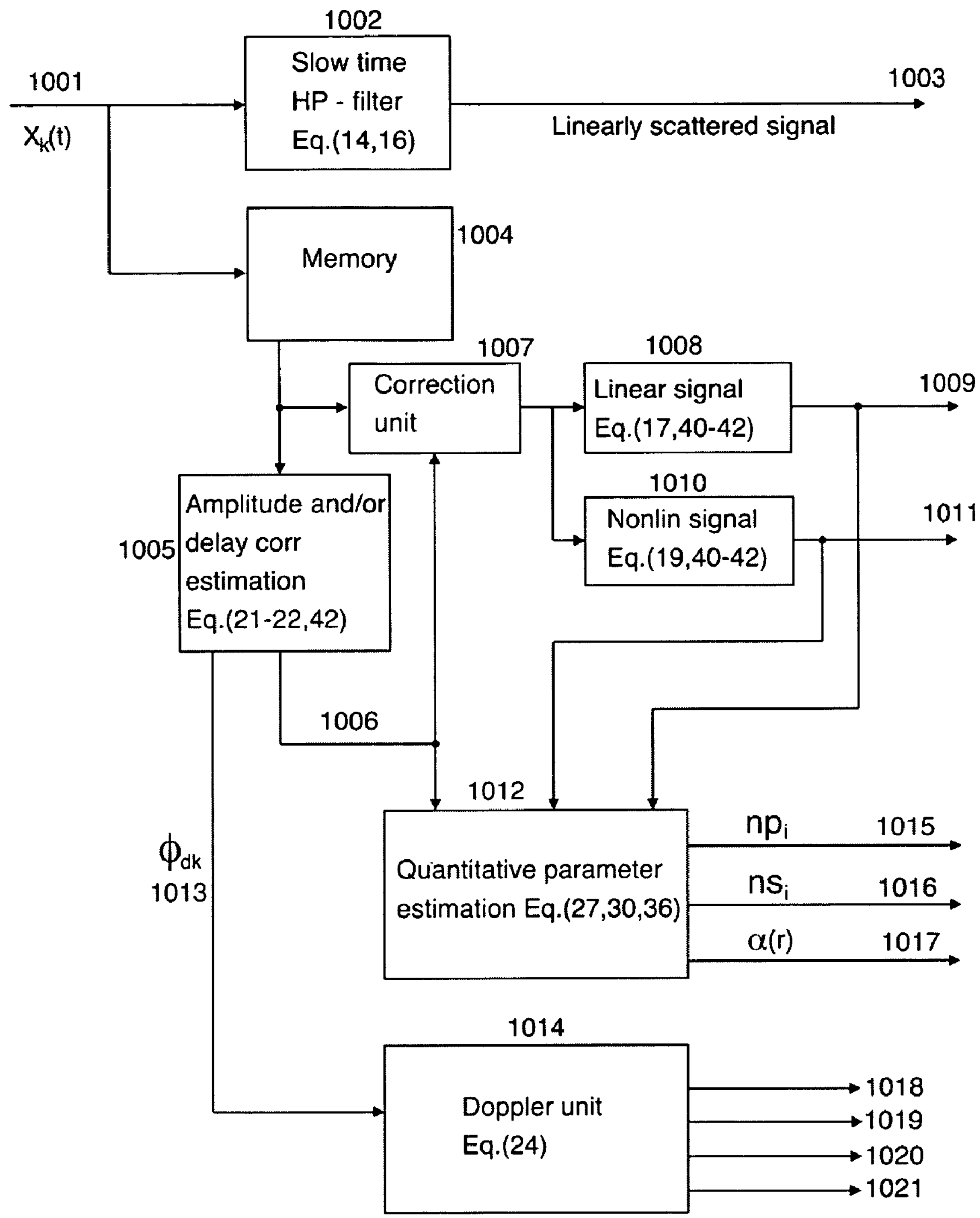
FIG. 10 shows a block diagram of an estimation unit for the signals and image parameters that can be obtained with the method.

The 1st method according to the invention described in relation to FIGS. 1 and 2 can be implemented as a modification of the receive filter found in most digital scanners today, or the receive filtering can be introduced in the radio frequency (RF) signal processing path. A block diagram of a processing unit for estimation of the amplitude and/or the delay corrections according to the 2nd or 3rd method according to the invention, together with image parameters according to this invention as given in Eqs. (14-30, 42-44), are shown in FIG. 10. The received RF signals $x_k(t)$ 1001 from consecutive transmitted pulse complexes are fed into a slow time high pass filter 1002 to produce the reverberation suppressed linear imaging signal 1003 according to Eq. (14), and also to a memory unit 1004 to allow more flexible processing of the signals. The received signals are then fed to an amplitude and/or delay correction estimator 1005 that operates according to one of the methods presented above, or similar, to provide accurate estimates 1006 of the amplitude and/or the nonlinear propagation delay corrections. The estimated amplitude and/or nonlinear propagation delay corrections are fed to a correction unit 1007 that takes signals from the memory unit and provides corrections for the amplitude and/or nonlinear propagation delays. The corrected signals are then fed to a unit 1008 that extracts the corrected linear signal 1009, for example according to Eqs. (17,18), or direct solution of Eq. (42), or similar, and a unit 1010 that extracts the corrected nonlinearly scattered signal 1011, for example according to Eqs. (19,20) or direct solution of Eq. (42), or similar. One should note that when methods similar to Eqs. (42-44) are used for the estimations, the pulse reverberations have minimal influence on the delay correction estimates, and also on the estimates of the linear and the nonlinear scattering signals. Per the discussion above, one could also use the 2nd harmonic band of the received signals for the estimation of the nonlinear propagation delays and also for the image signals. The appropriate units in the block diagram should then include filters for extraction of the 2nd harmonic band, or the input signals themselves could be the 2nd harmonic band signals.

The delay corrected linear (1009) and nonlinear (1011) signals are then together with the estimated delay corrections (1006) fed to a quantitative parameter estimation unit 1012 that calculates one or more of the quantitative nonlinear propagation parameters 1015 according to Eq. (27) or similar, and the quantitative nonlinear scattering parameters 1016 according to Eq. (30) or similar, and the local acoustic absorption coefficient $\alpha(r)$ 1017 according to Eq. (36). The delay correction unit 1005 can also present Doppler phases 1013, for example according to Eq. (24), that are fed to a Doppler unit 1014 that calculates the radial scatterer displacement 1018, radial scatterer velocity 1019, radial scatterer displacement strain 1020, and radial scatterer displacement strain rate 1021, or other parameter calculations. The signals 1003, 1009, 1011, 1015, 1016, 1017, 1018, 1019, 1020, 1021 are then typically passed to further processing and displays to generate full acoustic images according to known methods.

The 4th method according to the invention described in relation to Eqs. (45-48) operates more in a batch mode to estimate the corrections for the nonlinear propagation delays and the linearly and the nonlinearly scattered signal. Processors for such estimations can then be represented by the block diagram in FIG. 11, where 1101 represents the incoming measured signals $x_k(t)$ that are fed to the amplitude and/or delay correction and estimation unit 1102, that produces as its output the linearly scattered signal $x_l(t)$ as 1103, the nonlinearly scattered signal $x_n(t)$ as 1104, and the estimated corrections for the nonlinear propagation delays $\tau(t)$ and amplitude variations $a(t)$ as 1105. We should note with this method, the pulse reverberations and nonlinear scattering signals have minimal influence on the estimation of the delay corrections, although advantages can be found by using the 2nd harmonic band of the received signals as discussed in relation to Eqs. (42-44) above. The estimates of $x_l(t)$, $x_n(t)$, $\tau(t)$, and $a(t)$ are then fed to a quantitative parameter estimation unit 1106 that produces one or more of the nonlinear propagation parameter 1015, and the nonlinear scattering parameter 1016, and the local absorption parameter 1017, and the radial scatterer displacement 1018, and radial scatterer velocity 1019, and the radial scatterer displacement strain 1020, and radial scatterer displacement strain rate 1021, or other parameter calculations.

Figure 12:
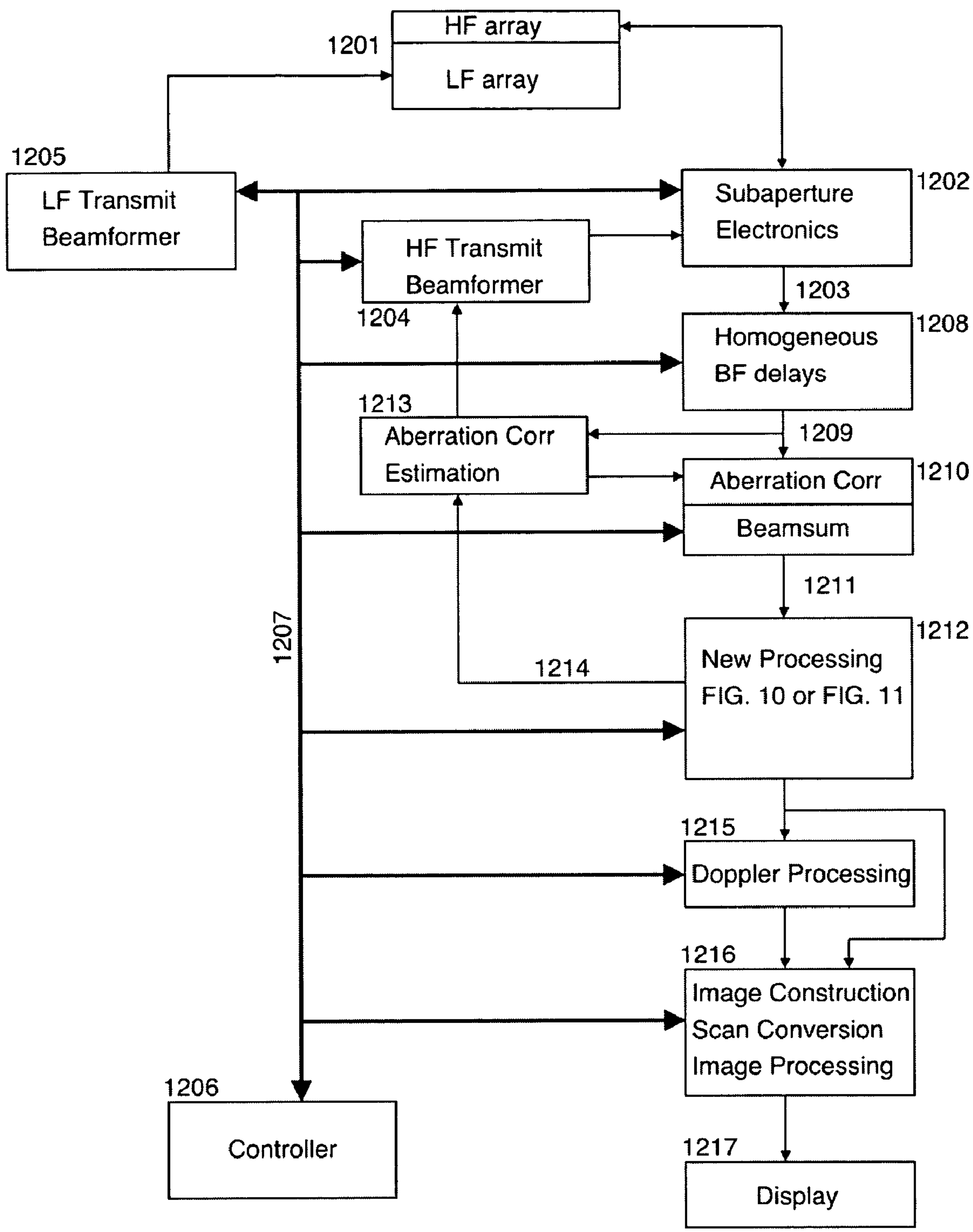
FIG. 12 shows a block diagram of an instrument for scatter imaging according to the invention.

The processing units can then be implemented both for tomographic reconstruction methods based on transmission and angular scattering measurements as in FIG. 9 and with back-scatter imaging instruments. A block diagram of a back-scatter imaging instrument in its broadest sense according to the invention, is shown in FIG. 12, where 1201 shows the acoustic transducer array that has a high frequency (HF) and low frequency (LF) section. In this broadest implementation of the methods, the array has a two dimensional distribution of elements, which allows full electronic 3D steering of the high and the low frequency beams, referred to as 2D array, and the instrument is also capable of both estimating and correcting for wave front aberrations. It is clear however that the methods can be used with less complex arrays, as discussed below.

The high frequency part of the array can in full 3D imaging applications have a large number of elements, for example 3000-10,000, and the number of receive and transmit channels are then typically reduced in a sub-aperture unit 1202, where in receive mode the signals from several neighboring array elements are delayed and summed to sub-aperture signals 1203 for further processing. For aberration corrections, the widths on the array surface of the sub-aperture groups are less than the correlation length of the wave front aberrations, where a typical number of sub-aperture groups and signals could be 100-1000.

For transmission of the pulse complexes, the HF transmit beam former 1204 feeds pulses to the sub-aperture unit 1202, that delays and distributes the signals to all or sub-groups of HF-array elements, while the LF transmit beam former 1205 simultaneously feeds pulses to the LF array elements. The pulse complex transmission is triggered by the instrument controller 1206, which communicates with the sub-units over the instrument bus 1207.

The receive sub-aperture signals 1203 are fed to the unit 1208, where the sub-aperture signals are delayed for steering of receive beam direction and focusing under the assumption of a homogeneous medium with the constant, average propagation velocity, referred to as homogeneous delays. 3D beam steering and focusing can also be done with sparse arrays, where the sub-aperture unit 1202 could typically be missing. With 1.75 D arrays, the number of HF array elements can also be reduced so much that the sub-aperture units could be left out. In the following we therefore use element and sub-aperture signals synonymously.

The element signals that are corrected with the homogenous delays, 1209, are fed to a unit 1210 where corrections for the wave front aberrations are applied, for example estimated as described in Eqs. (33,34) or according to the methods described in U.S. Pat. No. 6,485,423, U.S. Pat. No. 6,905,465 and U.S. patent application Ser. No. 10/894,38, before the element signals are summed to the final receive beam signal. For 3D imaging one would use multiple receive beams with small angular offsets that covers a wide transmit beam in parallel. The aberration corrections for the angularly offset beams could be a side shifted version of the corrections for the central beam, that are added together with the homogeneous delays for the angular offset in the unit 1210.

Figure 11:
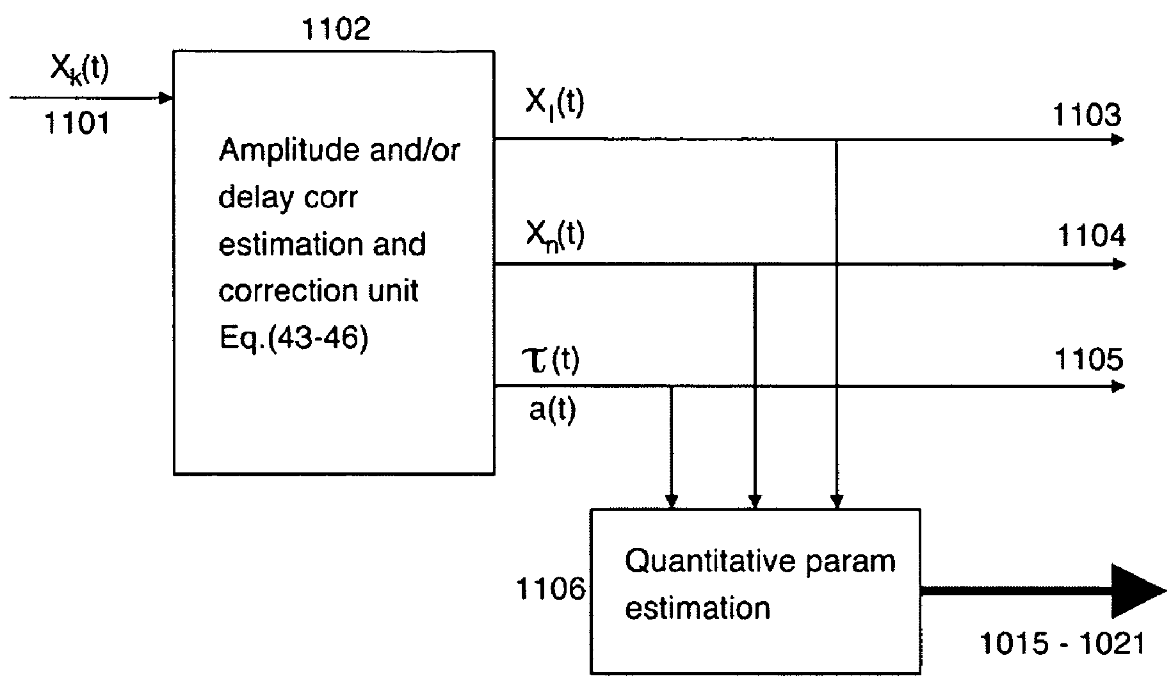
FIG. 11 shows yet another block diagram of an estimation unit for the signals and image parameters that can be obtained with the method.

The output 1211 of the unit 1210 is hence one or more RF-signals for one or more receive beam directions in parallel, that is fed to the processing unit 1212 according to this invention, that performs one or more of the operations according to FIG. 2, and FIG. 10, and FIG. 11. We should note for the operation according to FIG. 2, the high frequency pulse is for the bulk of the propagation distance found at the negative spatial gradient of the low frequency pressure oscillation, while for the methods described in FIG. 10 and FIG. 11, the high frequency pulse is for the bulk of the propagation distance found close to the peak or the trough of the low frequency pressure oscillation.

The aberration corrections are estimated in the unit 1213, for example according to the methods described in relation to the cited patents and patent applications and possibly also utilizing methods based on Eqs. (33,34). The unit 1213 takes as its input the homogeneously delay corrected signals 1209 and possibly also final beam signals 1214 with suppression of the pulse reverberation noise according to this invention. The delay corrected element signals 1209 are typically first processed with methods according to this invention, typically the method described in relation to FIG. 2 or Eq. (14) to suppress the pulse reverberation noise before estimation of the delay corrections. One should note that use of signal from moving scatterers as for example found with blood or myocardium and as prescribed in U.S. Pat. No. 6,485,423, would improve the function of methods of suppression of pulse reverberation noise as described in relation to Eq. (14). The estimates based on the nonlinear propagation delays for the individual element/sub-aperture signals as given in Eqs. (33,34) also represent interesting estimates themselves, and also as a starting point to for further estimations according to the cited patents, both to focus the 1$^{st}$ transmit beam and as starting points of an iteration scheme.

When estimation of the corrections for the wave front aberrations are based on signal correlations with the beam-former output signal 1214 with highly suppressed reverberation noise, the reverberation noise in the element signals is uncorrelated to the beam-former output signal. When slow updates of the aberration correction estimates are acceptable, one can use so long correlation times that the effect of the reverberation noise in the element signals on the correction estimates can be negligible. However, the correlation time is generally so low that it is preferable to also suppress the reverberation noise in the element signals before the estimation of the aberration corrections.

The outputs of the unit 1212 are the linearly and nonlinearly scattered signals, the two quantitative nonlinear parameters, and Doppler phase and frequency data, as described in relation to FIGS. 10 and 11. These data can be fed directly to the image construction and scan converter unit 1216 that presents images of compressed and colorized versions of the amplitudes of the linearly and nonlinearly scattered signals, the quantitative nonlinear parameters/signals, and object radial displacements, velocities, displacement strains and strain rates based on the outputs given in FIGS. 10 and 11. However, to measure the radial velocities of blood or gas bubbles or other fluids, one must further process the linearly or nonlinearly scattered signals in the slow time domain to suppress clutter echo from the object to retrieve the fluid signals for Doppler processing according to known methods, which is done in unit 1215. The outputs of this unit are fed to the image construction unit 1216 to be selected and overlaid the images of the other information. The unite 1216 feeds its output to a display 1217.

It should be clear to any-one skilled in the art, that many simplifications of the instrument as presented in FIG. 12 can be done while still utilizing essential aspects of the invention in the instrument. For example one can have a coarse division of elements in the elevation direction, which would limit electronic direction steering of the beam in the elevation direction, while one still can obtain corrections for the wave front aberrations and dynamic focusing with depth in the elevation direction. This is often referred to as 1.75D arrays and has much less total number of array elements than 2D array for full 3D steering of the beam, whereby the sub-aperture unit could be removed. Sparse arrays are another way to remove the number of elements so that it becomes practical to remove the sub-aperture unit 1202. However, the gain in using the sub-aperture unit is found as long as the dimension of the sub-aperture group along the array surface is less than the correlation length of the wave front aberrations.

One could also remove the estimations and the corrections for the wave front aberrations, i.e. units 1210 and 1213, and still be able to do the processing in unit 1212 to produce both linearly and nonlinearly scattered signals etc. as described above. The array could then be further simplified where elements symmetrically around the beam scan axis (the azimuth axis) is galvanically combined to further reduce the number of independent channels by a factor 2, often referred to as 1.5 D arrays. One could similarly use one dimensional (1D) arrays and also annular arrays with mechanical scanning of the beam direction, where the only modification to the block diagram in FIG. 12 is the sub-aperture unit 1202, the aberration correction unit 1210 and aberration correction estimation unit 1213 are removed.

Hence, as one can want instruments with different complexity, or selectable complexity, one also wants instruments that can select between the different methods of processing described above, for best performance according to the measurement situation. The numbering of the methods described above is related to an increase in complexity of the methods, with subsequently an increase in the number of pulses required per radial image line, and hence an increase in time per image, which is the inverse frame rate. The advantages and the drawbacks of the methods are:

1. The 1$^{st}$ method according to the invention, described in relation to FIGS. 1 and 2, obtains the results with a single transmitted pulse complex and provides suppression of the pulse reverberation noise with 1$^{st}$ harmonic sensitivity through radio frequency (RF) filtering of the received signal in fast time in unit 1212 of FIG. 12. The reverberation suppressed signals are further processed according to known methods of structural object imaging and Doppler imaging of moving scatterers and fluids, and radial displacement strain and strain rate imaging of relative scatterer movement in units 1215 and 1216. The method does not provide nonlinear scattering parameters or nonlinear propagation delay parameters, but provides the highest frame rate of all the methods.

2. The $2^{nd}$ method is described in relation to FIGS. 3-7 and Eqs. (10-41) and uses two or more transmitted pulse complexes for each radial image line with variations in the frequency and/or phase and/or amplitude of the low frequency pulse for each transmitted pulse complex. Through combination of the received signals from several pulses one obtains a $1^{st}$ image signal with suppression of the pulse reverberation noise and with $1^{st}$ harmonic sensitivity, estimation of the nonlinear propagation delays that gives a $2^{nd}$ image signal representing nonlinear scattering from the object, micro-calcifications, and micro-bubbles, and a $1^{st}$ and $2^{nd}$ quantitative nonlinear image parameter. When three or more pulses are transmitted one also obtain Doppler information according to Eq. (24), that is highly useful for studying radial displacement and velocity, and radial displacement strain and strain rates of object structures, such as the myocardium. The processed $1^{st}$ and $2^{nd}$ image signals can be used for amplitude imaging of object structures in unit 1216 and Doppler imaging of moving scatterers with clutter noise filtering in unit 1215. For amplitude tissue imaging the method gives lower frame rates than Method 1 above, as one must transmit two or more pulse complexes per radial image line, while with Doppler, displacement strain and strain rate imaging the frame rates of the two methods are similar. When $1^{st}$ harmonic signals are used for estimation of nonlinear propagation delays, the delay estimates will have errors produced by the reverberation noise, while one can with less sensitivity estimate nonlinear propagation delays from the $2^{nd}$ harmonic component of the received signals which has suppressed reverberation noise, or reduce the reverberation noise in other ways, to obtain estimates of nonlinear propagation delays with less errors produced by reverberation noise. The nonlinear scattering will also produce small errors in the delay estimates, which will influence the accuracy in the estimates of the $2^{nd}$ image signal and the quantitative nonlinear image parameters. However, these errors have minimal reduction of the suppression of the linearly scattered signal in forming the $2^{nd}$ image signal, which is an important result. The invention also provides guidelines for designs of dual band acoustic transducer arrays that produce an oscillatory variation of the phase of the transmitted low frequency pulse relative to the high frequency pulse with depth, for minimization of the maximal nonlinear propagation delays so that one for low amplitudes (~50 kPa) of the low frequency pulse can estimate approximate $2^{nd}$ nonlinear image signals without corrections for the nonlinear propagation delays.
3. The $3^{rd}$ method is described in relation to Eqs. (42-44) and uses 3 or more transmitted pulse complexes with at least 3 levels of frequency and/or phase and/or amplitude of the low frequency pulse, to produce one processed signal. The method eliminates the pulse reverberation noise before further estimation of the nonlinear propagation delays, and obtains estimates of linearly and nonlinearly scattered signals with strong suppression of the pulse reverberation noise. The $1^{st}$, Eq. (27), and $2^{nd}$, Eq. (30) quantitative nonlinear image parameters/signals are obtained as in Method 2. With 4 or more pulses one can also estimate a Doppler delay between the signals from consecutive pulses that is constant for each estimation interval $T_i$, similar to Eq. (24) for Method 2. This Doppler delay is highly useful for studying radial displacement and velocity, and radial displacement strain and strain rates of objects, such as the myocardium. For Doppler imaging of scatterer velocities where one need a clutter filter to remove object clutter, the processing would be done in unit 1215 as for the other methods. The nonlinear scattered signal still introduces small errors in the nonlinear delay estimates that will influence the accuracy in the estimates of the $2^{nd}$ nonlinearly scattered image signal, but as for Method 2 the errors will not reduce the suppression of the linearly scattered signal in the formation of the $2^{nd}$ nonlinear image signal, which is an important result. The method produces lower frame rates than Method 2.
4. The $4^{th}$ method is described in relation to Eqs. (45-48) and uses 4 or more transmitted pulse complexes with 4 or more levels of frequency and/or phase and/or amplitude of the low frequency pulse, to produce one processed signal of $1^{st}$ order linear scattering, $1^{st}$ order nonlinear scattering, and nonlinear propagation delays. The $1^{st}$, Eq. (27), and $2^{nd}$, Eq. (30), quantitative nonlinear image parameters/signals are obtained as in Method 2. With at least 5 transmitted pulse complexes with 5 variations of the frequency and/or phase and/or amplitude of the low frequency pulse one can also estimate errors in the low frequency pulse phases and/or amplitudes, and/or Doppler delays between the 5 transmitted pulses. This Doppler delay is highly useful for studying radial displacement and velocity, and radial displacement strain and strain rates of objects, such as the myocardium. For Doppler imaging of scatterer velocities where one need a clutter filter to remove object clutter, the processing would be done in unit 1215 as for the other methods. The estimates of the nonlinear propagation delays will have minimal influence by the pulse reverberation noise and the nonlinear scattering, hence producing the most accurate estimation of the nonlinear propagation delays, the linearly and the nonlinearly scattered signals, at the cost of the lowest frame rate of all the methods.

The invention devices an instrument that can operate according to at least two of the methods, with the ability to select the best method for the needs, where the selection can be done under direct control of the operator, or the operator can set constraints, where the instrument automatically selects methods for best performance according to the constraints under different operating conditions.

An example constraint set by the operator can be a minimal frame rate, where for low depth ranges where it is possible to use high pulse repetition frequency, one can use the highest numbered method in the list above that still meets the frame rate constraint to obtain best possible performance with the needed frame rate. For larger depth ranges where the pulse repetition frequency must be reduced the instrument selects one of the former methods that still meets the frame rate constraint albeit with poorer estimation quality. Another example constraint is a combination of frame rate and estimation quality, where increasing the range for intermediate ranges the quality is dropped while the frame rate is maintained, and for larger depth ranges the frame rate is dropped while the quality is maintained.

The method selection could also automatically depend on imaging modality, where for linear object imaging of the heart one would use Method 1 with reverberation suppressed image signals for highest frame rate, while for studying movement in the myocardium the instrument could switch to Method 2 with 2-4 transmitted pulse complexes per radial image line, utilizing Eq. (24) for myocardial movement. For imaging of scatterer velocities the instrument could switch to Method 2 with 8-16 transmitted pulse complexes per radial image line, using the processing in unit 1215. For stationary objects like the prostate, the breast, the liver, etc. one could typically choose Method 4 for best possible estimation of the $1^{st}$ order linearly and nonlinearly scattered signals, the nonlinear propagation delays and quantitative image parameters.

Figure 13:
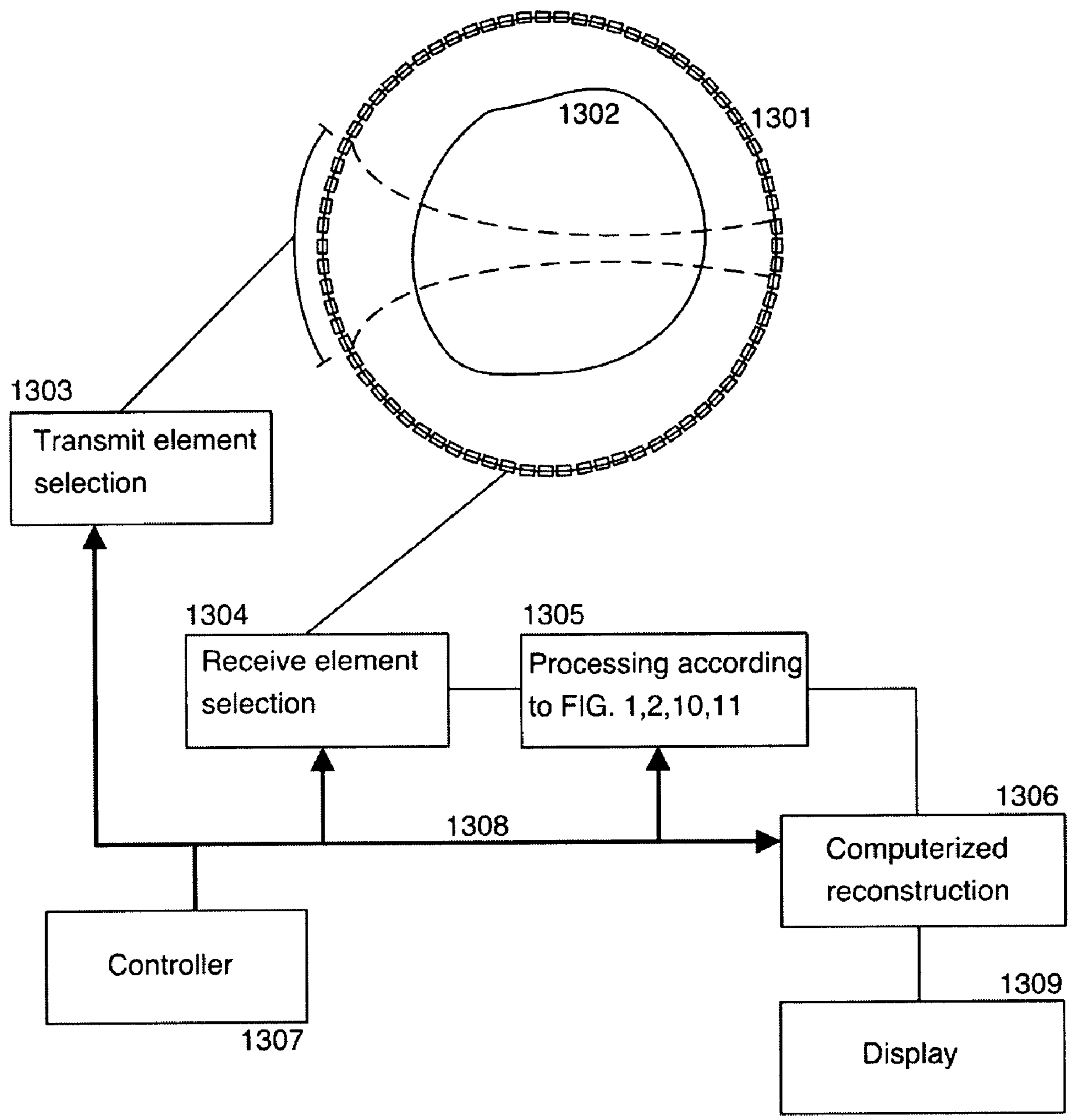
FIG. 13 shows a block diagram of an instrument for tomographic image reconstruction from transmission and angular scattering measurements according to the invention.

For tomographic reconstruction, the processing according to this invention would typically be done on the individual receive element signals, before the signals are processed according to the reconstruction algorithms of various kinds, where a block schematic of a typical instrument for tomographic image reconstruction according to the invention is shown in FIG. 13. The Figure shows measurements with a ring array 1301, where it is clear for anyone skilled in the art that other array configurations, also transducer arrays that would wholly or partly use mechanical scanning to collect the data, could be used without departing from the invention. The array surrounds the object 1302. A unit 1303 selects a group of transmit elements, freely out of all the elements, and generates a transmit pulse complex composed of a low and a high frequency pulse overlapping in time and for example as visualized in FIG. 1 and FIG. 3. Transmissions of the pulse complexes are triggered by the controller unit 1307 via the controller bus 1308. The unit 1304 selects receive elements, sequentially or in parallel or a combination of parallel-sequential manner, from the whole group of elements, and amplifies and digitizes the element signals for further processing according to the invention in the unit 1305. This unit operates according to the principles according to the invention, for example as described in FIGS. 1 and 2 for a single pulse complex per processed signal, or FIG. 10 or 11, for multiply transmitted pulses per processed signal. The processing in unit 1305 provides on or more of the linearly scattered and transmitted signals with substantial suppression of the pulse reverberation noise (multiple scattering), nonlinearly scattered signals, and quantitative nonlinear propagation and scattering parameters that are forwarded to the unit 1206 that provides computerized tomographic images of 2D slices of the object. By mechanically moving the array relative to the object in the direction normal to the Figure, one obtains a 3D reconstructed image of the object.

Figure 14:
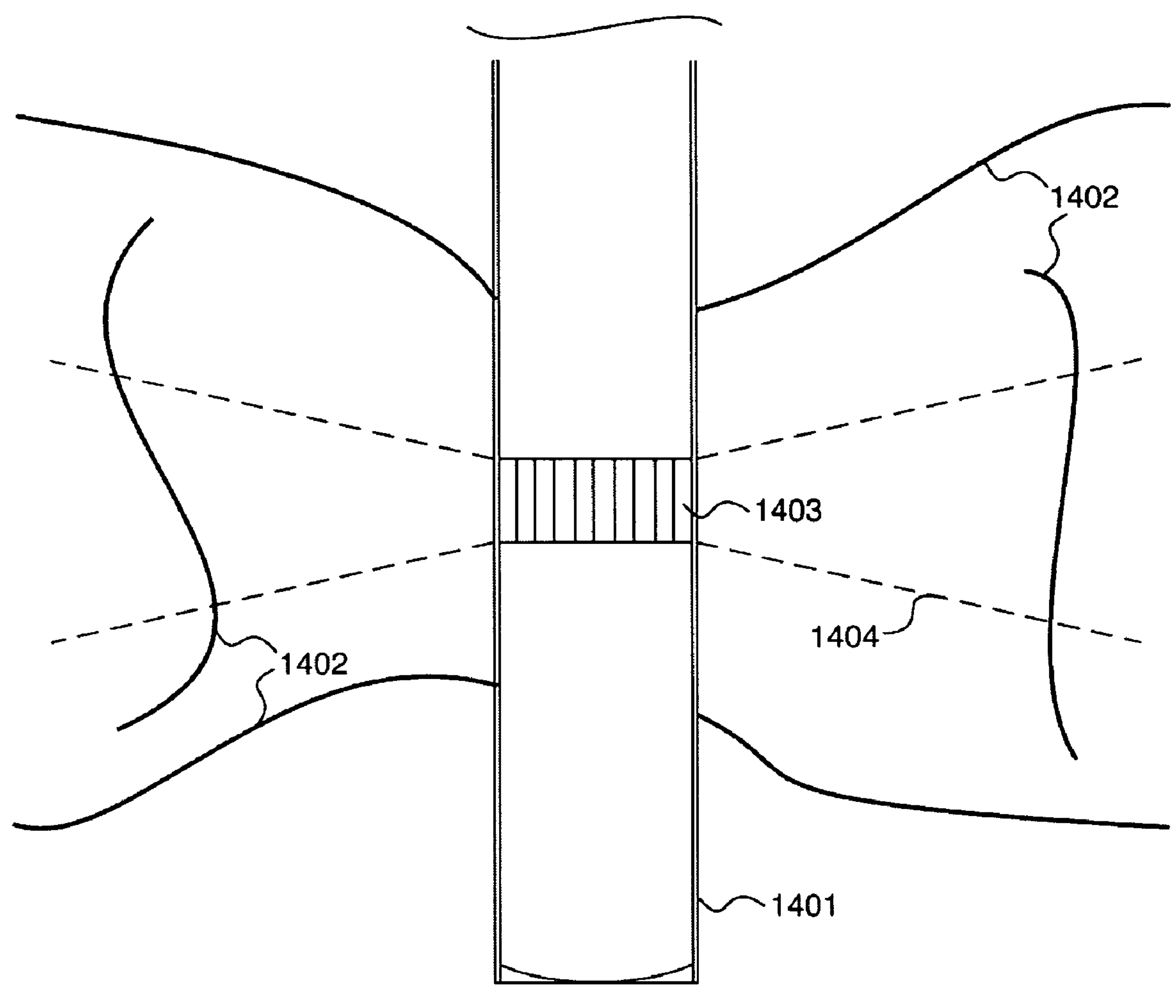
FIG. 14 shows an acoustic transducer arrangement in an oil well for observation of the geologic structures around the oil well.

An example instrumentation for use of the methods for acoustic imaging of geologic structures around an oil well, is shown in FIG. 14. 1401 indicates the perforated oil-well production liner, with surrounding geologic structures 1402 that typically is composed of porous rock filled with oil, gas, water or mixtures of these, where also solid rock regions can be found. 1403 illustrates an acoustic array for transmission and reception of acoustic pulse complexes according to the invention in selectable sector beams 1404 around the production liner. The received acoustic signals are processed according to the methods described above with the exemplified instrumentation shown in FIG. 10, 11, 12. With oil wells sufficiently close to each other one can also use transmission measurements between oil wells and reconstruct images from transmission and angular measurements as described above, particularly in relation to FIGS. 9 and 13, as described above.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps which perform substantially the same function in substantially the same ways to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We will in the claims use the following concepts:

Received signals which are the signals $x_k(t)$ first introduced prior to Eq. (11), or its analytic form $x_k\hat{}(t)$ defined in Eq. (11), or its complex envelope defined in Eq. (12,13).

Figure 5:
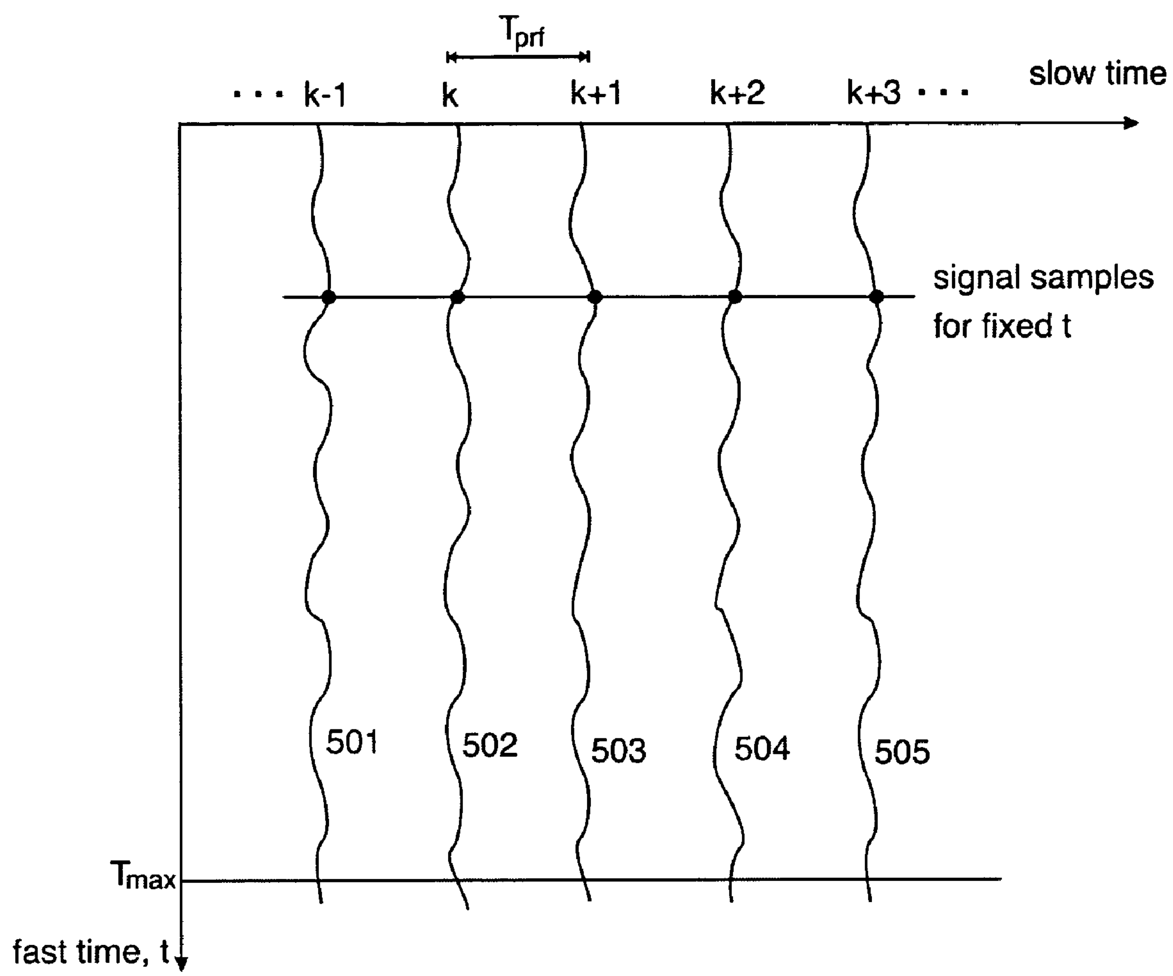
FIG. 5 illustrates a set of received high frequency signals from consecutive transmit pulses as a function of the fast time (depth) and slow time (pulse number coordinate)

Fast time, and slow time or pulse number coordinate, is defined in relation to FIG. 5.

Slow time filtering or filtering along the pulse number coordinate is defined in relation to FIG. 6

Pulse reverberation noise is defined in relation to FIG. 7.

Tomographic reconstruction imaging is defined in relation to FIG. 9.

Nonlinearly scattered signal is the nonlinearly scattered signal from the high frequency pulse with the linearly scattered components highly suppressed, and defined in Eqs. (9,11-13,19, 42-48), or its analytic form, or its complex envelope defined similar to that for $x_k(t)$.

Linearly scattered signal is the received signal from the linear scattering of the high frequency pulse in the object defined in Eqs. (9, 11-13, 17, 42-48), or its analytic form, or its complex envelope defined similar to that for $x_k(t)$.

Reverberation suppressed imaging signal, or $1^{st}$ imaging signal, defined in Eq. (14, 42-48) or in relation to FIG. 2.

Nonlinear propagation delays are defined in relation to Eq. (10).

Total propagation delays is the sum of the nonlinear propagation delays and the Doppler displacement delays (Doppler delays) defined in relation Eq. (23).

Delay corrections or corrections for nonlinear propagation delays or the total propagation delays are defined in Eqs. (10, 17-25 and 49,50).

$2^{nd}$ image signal is defined in Eqs. (19,28) and in Eqs. (42-48) as the nonlinearly scattered signal.

$3^{rd}$ image signal is defined in Eqs. (17,29) and in Eqs. (42-48) as the linearly scattered signal.

Amplitude corrections are defined in relation to Eq. (19, 22).

Estimation intervals $T_i$ are defined in relation to Eq. (21, 44).

$1^{st}$ quantitative nonlinear imaging parameter, or nonlinear propagation parameter, is defined in Eq. (27).

$2^{nd}$ quantitative nonlinear imaging parameter, or nonlinear scattering parameter, is defined in Eq. (30).

Recursive procedure is a calculation procedure that is repeated for several steps, and where the values of parameters are updated for each step in the procedure. Defined in relation to Eqs. (54, 58, 63, 81).

Iterative procedure is the same as a recursive procedure.

We claim:

1. A method for measurement or imaging of at least one of acoustic scattering and propagation properties in a region of an object, the method comprises:

a) transmitting at least one acoustic pulse complex in beams towards the region of the object, the at least one acoustic pulse complex including at least one acoustic high frequency (HF) pulse and at least one acoustic low frequency (LF) pulse with the same or overlapping beam directions;

b) receiving HF receive signals with a HF transducer array from at least one of acoustic waves produced by object scattering of the at least one HF pulse, and acoustic waves of the at least one HF pulse that have propagated through the object; and c) forming measurement or image signals from the HF receive signals, wherein the step of forming comprises using the at least one LF pulse to produce a nonlinear manipulation of elastic properties of the region of the object observed by the at least one HF pulse to suppress the deteriorating effect on the measurement or image signals of pulse reverberation noise from multiple scattering of the at least one HF pulse.

2. The method according to claim 1, wherein the step of forming comprises at least one of a) propagating the at least one HF pulse, at least for a portion of the image depth range, on a negative spatial gradient of the at least one LF pulse, and b) arranging a phase relationship between the at least one HF pulse and the at least one LF pulse that slides with depth so that in one range the at least one HF pulse propagates along a zero or a positive spatial gradient of the at least one LF pulse, so that improved penetration or resolution of the at least one HF pulse at deeper ranges is obtained, and improved frequency separation of the pulse reverberation noise and the $1^{st}$ order scattered signal of the at least one HF pulse is obtained.

3. The method according to claim 2, further comprising filtering the HF receive signal in the fast time domain using a filter that suppresses at least lower frequencies, wherein at least the filter lower cut-off frequency slides with a depth of penetration of the at least one acoustic pulse complex to at least at some depth range produce a $1^{st}$ signal representing the linearly scattered HF signal from the region of the object with substantial suppression of pulse reverberation noise for further processing to form measurement or image signals.

4. The method according to claim 1, wherein tomographic image reconstruction is performed based on the HF receive signals.

5. The method according to claim 2, wherein high frequency observation pulses are used to observe object deformation due to radiation force acoustic push pulses, the observation pulses for a substantial portion of the depth range propagate along a negative spatial gradient of the low frequency pulses to impose pulse compression frequency up-conversion of the high frequency observation pulses, and the radiation force push pulses are transmitted as one of:

a) a high frequency push pulse without a low frequency pulse, and b) a sequence of high frequency push pulses together with low frequency pulses such that for a substantial portion of the depth range the high frequency push pulses propagate along a positive spatial gradient of the low frequency pulses for down conversion of the frequency of the high frequency push pulses, so that overlapping received signals from the observation pulses and the push pulses can be separated through filtering in the depth time (fast time).

6. The method according to claim 3, wherein the $1^{st}$ signal is used for tomographic image reconstruction.

7. The method according to claim 3, where the $1^{st}$ signal with suppression of the pulse reverberation noise is used in the process of estimating corrections for wave front aberrations.

8. The method according to claim 3, wherein the step of transmitting includes transmitting broad HF and LF beams that cover multiple parallel receive beams to increase the image frame rate in 2D and 3D acoustic imaging, where $1^{st}$ signals with suppressed reverberation noise are obtained for each of the parallel receive beams and used in the process of forming measurement or image signals for each of the parallel receive beams.

9. The method according to claim 1, wherein the step of transmitting at least one acoustic pulse complex comprises transmitting at least two pulse complexes towards the region of the object with the same or overlapping beam directions for each measurement or image line, and wherein for each of the at least two pulse complexes, at least one of a frequency, an amplitude and a phase of the at least one LF pulse varies, and the amplitude of the at least one LF pulse of at least one of the at least two pulse complexes is nonzero, and wherein the step of forming includes forming the measurement or image signals by a combination of the HF receive signals from the at least two transmitted pulse complexes.

10. The method according to claim 9, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and $3^{rd}$ signal representing the received signal from linear scattering of the HF pulses with the same depth variable gain and acoustic absorption as the $2^{nd}$ signal.

11. The method according to claim 10, wherein the $1^{st}$ signal is extracted from the HF receive signals in a process that includes the step of filtering along the pulse number coordinate (slow time) to suppress low frequency slow time components and let through higher frequency slow time components.

12. The method according to claim 10, wherein tomographic image reconstruction is performed based on one of the $1^{st}$, $2^{nd}$ and $3^{rd}$ signals.

13. The method according to claim 9, further comprising estimating, from the HF receive signals from the at least two pulse complexes, pulse to pulse variable total propagation delays as a sum of Doppler delays and nonlinear propagation delays of the HF received signals from different pulse complexes, the step of forming measurement or image signals is based on the estimated total propagation delays.

14. The method according to claim 13, wherein the nonlinear propagation delays are estimated through one of a) estimating that the Doppler delays are negligible due to small movement between scatterers and transducer array, and b) transmitting at least three pulse complexes in the step of transmitting, wherein for each of the at least three pulse complexes, at least one of a frequency, an amplitude and a phase of the at least one LF pulse varies, and both the nonlinear propagation delays and the Doppler delays are separately estimated from the HF receive signals, and wherein the step of forming measurement or image signals is based on at least one of the estimated Doppler delays and the nonlinear propagation delays.

15. The method according to claim 14, where a nonlinear image parameter or signal, which is a local nonlinear forward propagation image parameter or signal representing local nonlinear propagation parameters of the region of the object, is formed from the differential along the fast time of the estimated nonlinear propagation delays.

16. The method according to claim 15, wherein the local nonlinear forward propagation image parameter or signal is used to estimate at least one of:

relative volume of at least one of gas, oil and water in porous rock, changes in the volume of at least one of gas, oil and water in porous rock, size and amount of fish with swim bladder or sea animals with lungs in water, and material parameters of biological tissues and fluids.

17. The method according to claim 14, where a $1^{st}$ quantitative nonlinear image parameter or signal, which is a local nonlinear forward propagation image parameter or signal representing local nonlinear propagation parameters of the region of the object, is formed as a combination of the differential along the fast time of the estimated nonlinear propagation delays, and an estimate of the local pressure amplitude of the at least one LF pulse at the location of the at least one HF pulse.

18. The method according to claim 17, wherein a $2^{nd}$ quantitative nonlinear image parameter or signal, which is a nonlinearly scattered image parameter or signal representing local nonlinear scattering parameters of the region of the object, is formed by combining an envelope of the $2^{nd}$ signal, an envelope of the $3^{rd}$ signal, and an estimate of the local pressure amplitude of the at least one LF pulse at the co-propagating at least one HF pulse, and performing at least one of estimating relative micro-vessel volume in the region of the object, and fluid perfusion through the region of the object based on at least one of the $1^{st}$ and $2^{nd}$ quantitative nonlinear image parameters or signals from an object that contains contrast agent microbubbles.

19. The method according to claim 17, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and a $3^{rd}$ signal representing the received signal from linear scattering of the HF pulses with the same depth variable gain and acoustic absorption as the $2^{nd}$ signal; and wherein a $2^{nd}$ quantitative nonlinear image parameter or signal, which is a nonlinearly scattered image parameter or signal representing local nonlinear scattering parameters of the object, is formed by combining the envelope of the $2^{nd}$ signal and the envelope of the $3^{rd}$ signal and an estimate of the local pressure amplitude of the at least one LF pulse at the co-propagating at least one HF pulse, and wherein at least one of the $1^{st}$ and $2^{nd}$ quantitative nonlinear image parameters or signals are used in a process of monitoring local object temperature during thermal treatment of the object.

20. The method according to claim 17, wherein the $1^{st}$ quantitative nonlinear image parameter or signal is used to estimate at least one of:

relative volume of at least one of gas, oil and water in porous rock, changes in the volume of at least one of gas, oil and water in porous rock, size and amount of fish with swim bladder or sea animals with lungs in water, and material parameters of biological tissues and fluids.

21. The method according to claim 14, wherein one from the estimated Doppler delays estimates at least one of:

a radial displacement of the region of the object along the beam direction as a function of depth along the beam, a radial displacement velocity of the region of the object along the beam direction as a function of depth along the beam, a radial mechanical strain of the region of the object along the beam direction is estimated from the differential along the depth range of the estimated displacement, and a radial mechanical strain rate of the region of the object along the beam direction is estimated from the differential along the depth range of the estimated displacement velocity.

22. The method according to claim 14, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and a $3^{rd}$ signal representing the received signal from linear scattering of the HF pulses with the same depth variable gain and acoustic absorption as the $2^{nd}$ signal, wherein the step of transmitting at least one acoustic pulse complex comprises transmitting at least five pulse complexes toward the region of the object with the same or overlapping beam directions for each measurement or image line, and wherein for each of the at least five pulse complexes, at least one of a frequency, an amplitude and a phase of the at least one LF pulse varies, and the nonlinear propagation and Doppler delays are estimated from the received signals in a procedure, wherein a) a signal model is adaptable to the HF receive signals, the signal model is a combination of linear scattering components, nonlinear scattering components, and pulse reverberation noise components, and the signal model includes delay parameters representing the nonlinear propagation delays and Doppler delays of the HF receive signals, b) estimates of the linearly scattered signals and the nonlinearly scattered signals are determined respectively as the linear scattering components and the nonlinear scattering components of the signal model that together with the pulse reverberation components of the signal model is adapted in a defined sense to the measured HF receive signals, c) estimates of the nonlinear propagation delays and Doppler delays are obtained as the delay parameters that minimize the error in a defined sense between the adapted signal model and the measured HF receive signals, and d) the $1^{st}$ and $3^{rd}$ signals are set equal to the adapted linear scattering model components, and the $2^{nd}$ signal is set equal to the adapted nonlinear scattering model components.

23. The method according to claim 22, where estimates of the linearly scattered signal, and nonlinearly scattered signal, and the pulse reverberation noise are found as the estimates that provide best adaptation of the signal model to the measured signals in the least square sense.

24. The method according to claim 22, wherein, when Doppler delays between transmitted pulse complexes are known or negligible, at least four of the at least five acoustic pulse complexes with the given specifications are transmitted, and where only the nonlinear propagation delay is estimated.

25. The method according to claim 14, further comprising estimating a local absorption coefficient in the object from the estimated nonlinear propagation delay, the depth gradient of the estimated nonlinear propagation delay, and an estimate of the high center frequency in the received signal and the depth gradient of the estimate of the high center frequency where the high frequency pulse for a substantial portion of the depth range propagates along a negative spatial gradient of the low frequency pulse.

26. The method according to claim 14, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and a $3^{rd}$ signal representing the received signal from linear scattering of the HF pulses with the same depth variable gain and acoustic absorption as the $2^{nd}$ signal, the method further comprising estimating, from the HF receive signals from the at least two pulse complexes, pulse to pulse variable total propagation delays as a sum of Doppler delays and nonlinear propagation delays of the HF receive signals from different pulse complexes, wherein the step of forming measurement or image signals is based on the estimated total propagation delays, wherein at least one of the HF receive signals is delay corrected with one of the estimated total propagation delays and the nonlinear propagation delays, wherein the at least one of the HF receive signals and the remainder of the HF receive signals form delay corrected signals, and the $2^{nd}$ signal is estimated in a process that includes the steps of combining the delay corrected signals along the pulse number coordinate (slow time) to suppress low frequency slow time components of the delay corrected receive signals.

27. The method according to claim 13, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and a $3^{rd}$ signal representing the received signal from linear scattering of the HF pulses with the same depth variable gain and acoustic absorption as the $2^{nd}$ signal, the method further comprising estimating, from the HF receive signals from the at least two pulse complexes, one of pulse to pulse variable total propagation delays as a sum of Doppler delays, and nonlinear propagation delays of the HF receive signals, and nonlinear propagation delays from different pulse complexes, wherein the step of forming measurement or image signals is based on one of the estimated total propagation delays and nonlinear propagation delays, wherein at least one of the HF receive signals is delay corrected with one of the estimated total propagation delays and the nonlinear propagation delays, and the $2^{nd}$ signal is estimated in a process that includes the steps of combining, after the delay correcting, the HF receive signals along the pulse number coordinate (slow time) to suppress low frequency slow time components.

28. The method according to claim 27, wherein at least one of the HF receive signals are amplitude corrected, and the amplitude and delay corrected HF receive signals are combined to provide an estimate of the $2^{nd}$ signal.

29. The method according to claim 28, where the amplitude corrections are estimated from a minimization of the power in the estimated $2^{nd}$ signal under the constraint that the amplitude correction vector has a fixed norm.

30. The method according to claim 13, wherein an entire receive time interval T is divided into sub intervals $T_i$ that are sufficiently short so that the total propagation delays can be approximated as constant in each sub interval, and the total propagation delays are estimated in a process that maximizes the power in each sub interval of the signal that is obtained by delay correction of at least one of the HF receive signals with the estimated total propagation delays and low pass filtering the HF receive signals after the delay correction in the slow time coordinate.

31. The method according to claim 13, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and a $3^{rd}$ signal representing the received signal from linear scattering of the HF pulses with the same depth variable gain and acoustic absorption as the $2^{nd}$ signal the method further comprising combining the HF receive signals from the set of transmitted pulse complexes to form a set of new signals with suppressed pulse reverberation noise, and estimating the total propagation delays, the linearly scattered signal, and the nonlinearly scattered signal from said set of new signals, and the $1^{st}$ and $3^{rd}$ signals are set equal to the estimated linearly scattered signal, and the $2^{nd}$ signal is set equal to the nonlinearly scattered signal.

32. The method according to claim 13, wherein the estimation of the total propagation delays or the nonlinear propagation delays is based on a $2^{nd}$ harmonic band of the HF receive signals.

33. The method according to claim 13, wherein the step of forming measurement or image signals includes estimating at least one of the following signals from the HF receive signals:

a $1^{st}$ signal representing the received signal from linear scattering of the HF pulses with substantial suppression of pulse reverberation noise, a $2^{nd}$ signal representing the received signal from nonlinear scattering of the HF pulses with substantial suppression of linear scattering signal, and a $3^{rd}$ signal representing the received signal from linear scattering of the HF pulses with the same depth variable gain and acoustic absorption as the $2^{nd}$ signal the method further comprising estimating, from the HF receive signals from the at least two pulse complexes, one of pulse to pulse variable total propagation delays as a sum of Doppler delays and nonlinear propagation delays of the HF receive signals, and nonlinear propagation delays from different pulse complexes, wherein at least one of the HF receive signals is delay corrected with one of the estimated total propagation delays and nonlinear propagation delays, and the $3^{rd}$ signal which is an estimate of the linearly scattered signal, is extracted in a process that includes the steps of combining, after the delay correcting, the HF receive signals along the pulse number coordinate to let through slow time frequency components around zero and suppress other slow time frequency components.

34. The method according to claim 10, wherein a nonlinear image parameter or signal, which is a local nonlinearly scattered image parameter or signal representing local nonlinear scattering parameters of the region of the object, is formed by combining an envelope of the $2^{nd}$ signal and an envelope of the $3^{rd}$ signal.

35. The method according to claim 34, wherein the local nonlinearly scattered image parameter or signal is used to estimate at least one of:

relative volume of at least one of gas, oil and water in porous rock, changes in the volume of at least one of gas, oil and water in porous rock, size and amount of fish with swim bladder or sea animals with lungs in water, and material parameters of biological tissues and fluids.

36. The method according to claim 10, wherein a $2^{nd}$ quantitative nonlinear image parameter or signal, which is a nonlinearly scattered image parameter or signal representing local nonlinear scattering parameters of the region of the object, is formed by combining an envelope of the $2^{nd}$ signal, an envelope of the $3^{rd}$ signal, and an estimate of the local pressure amplitude of the at least one LF pulse at the co-propagating at least one HF pulse.

37. The method according to claims 17 and 36, wherein the $2^{nd}$ quantitative nonlinear image parameter or signal is used to estimate at least one of:

relative volume of at least one of gas, oil and water in porous rock, changes in the volume of at least one of gas, oil and water in porous rock, size and amount of fish with swim bladder or sea animals with lungs in water, and material parameters of biological tissues and fluids.

38. The method according to claim 10, further comprising estimating corrections for wave front aberrations based on the $1^{st}$ signal with suppression of the pulse reverberation noise.

39. The method according to claim 38, wherein the HF transducer array has a two-dimensional distribution of elements, and where at least one of:

element signals that are the received HF signals from array elements; and sub-aperture signals that are combinations of the received HF signals from sub-aperture groups of neighboring array elements, are processed to provide new element or sub-aperture signals with substantial suppression of pulse reverberation noise, and the estimation of corrections for wave front aberrations is based on the new element or sub-aperture signals.

40. The method according to claim 39, wherein the nonlinear propagation delays are estimated for the new element or sub-aperture signals and the process of estimating corrections for wave front aberrations is based on the non linear propagation delays.

41. A method according to claim 38, wherein the step of transmitting includes transmitting broad HF and LF beams that cover multiple parallel receive beams to increase the image frame rate in 2D and 3D acoustic imaging, where $1^{st}$ signals with suppressed reverberation noise are obtained for each of the parallel receive beams and measurement or image signals are formed for each of the parallel receive beams based on the $1^{st}$ signals with suppressed reverberation noise, and wherein the corrections for wave front aberrations for one transmit beam direction are estimated based on a highly focused HF beam, followed by transmission of broad HF and LF beams with multiple parallel receive beams to increase 2D and 3D frame rate, utilizing aberration corrections for each receive beam derived from the estimated aberration corrections obtained with the focused transmit beam.

42. The method according to claim 38, wherein the nonlinear propagation delays are estimated and the estimating of corrections for wave front aberrations is based on the estimated nonlinear propagation delays.

43. The method according to claim 10, wherein the step of transmitting includes transmitting broad HF and LF beams that cover multiple parallel receive beams to increase the image frame rate in 2D and 3D acoustic imaging, where $1^{st}$ signals with suppressed reverberation noise are obtained for each of the parallel receive beams and measurement or image signals are formed for each of the parallel receive beams based on the $1^{st}$ signals with suppressed reverberation noise.

44. The method according to claim 10, wherein the step of transmitting includes generating the at least one LF pulse and the at least one HF pulse with acoustic transducer arrays in which at least part of the radiation surfaces for the at least one LF pulse and the at least one HF pulse are different, so that the phase of the at least one LF pulse varies relative to the phase of the at least one HF pulse throughout the actual image range to produce a nonlinear propagation delay of the at least one HF pulse by the at least one LF pulse that has a non-monotone variation along the axis of the HF beam that limits the maximal nonlinear propagation delay, so that for low amplitudes of the at least one LF pulse in the range of approximately 50-100 kPa one can suppress the linearly scattered HF signal from the tissue and estimate the $2^{nd}$ signal from micro gas bubbles through a combination in the pulse number coordinate of the received HF signals from at least two pulses without corrections for nonlinear propagation delays in fast time.

45. The method according to claim 44, wherein the acoustic transducer arrays including an HF array for generating the at least one HF pulse, the HF array being a linear array, and an LF array for generating the at least one LF pulse, the LF array being one of one linear array mounted on one side of the HF array, and two linear arrays mounted on each side of the HF array.

46. The method according to claim 10, wherein at least one of the $1^{st}$, $2^{nd}$ and $3^{rd}$ signals is used to detect or image high compliance objects including at least one of fat and lipid particles in biological tissues and fluids, gas bubbles in biological tissues and fluids, fish and sea animals in water, soft regions in geologic structures, and content of at least one of oil and gas and water in porous rock.

47. The method according to claim 10, wherein at least one of the $1^{st}$, $2^{nd}$ and $3^{rd}$ signals is used to detect or image low compliance objects including at least one of small calcifications in biological tissues and fluids, hard objects in soft tissue and fluids, mines in geologic structures, hard regions in geologic structures, and content of at least one of oil and gas and water in porous rock.

48. The method according to claim 10, wherein the nonlinearly scattered signal is used to differentiate between rocks containing oil, gas, or water in the neighborhood of an oil well.

49. The method according to claim 1, wherein the step of forming includes suppressing signal components from the at least one LF pulse in the received signal to extract the HF receive signal for further processing.

50. The method according to claim 1, where a $2^{nd}$ harmonic band of the HF receive signals is used to form the measurement or image signals.

51. The method according to claim 1, wherein the object is the neighborhood of an oil well.

52. The method according to claim 1, wherein harmonic components of the at least one LF pulse in the received HF signal are suppressed by transmitting the at least one low frequency pulse without the at least one high frequency pulse and storing the received high band signal produced therefrom, and subtracting the stored high band signal from the received high band signals from transmitted pulse complexes that contain both the at least one LF pulse and the at least one HF pulse.

53. The method according to claim 1, wherein the at least one HF pulse is at least in the near depth range placed close to a positive pressure peak of the at least one LF pulse in the transmitted pulse complex so that the maximal amplitude of the high frequency pulse can be increased within the limit of the maximally allowed Mechanical Index of the complex, for increased sensitivity with measurements both in the fundamental and harmonic bands of the at least one HF pulse.

54. An instrument for measurement or imaging of at least one of acoustic scattering and propagation properties in a region of the object, the instrument comprising:

a) transmitting means for transmitting at least one acoustic pulse complex in beams towards the region of the object, each the at least one pulse complex being composed of at least one acoustic high frequency (HF) pulse and at least one acoustic low frequency (LF) pulse with the same or overlapping beam directions, and b) HF transducer and receiver means for receiving HF receive signals from at least one of acoustic waves produced by object scattering of the at least one HF pulse, and acoustic waves of the at least one HF pulse that have propagated through the object, and c) means for forming measurement or image signals from the HF receive signals, the means for forming comprising means for using the at least one LF pulse to produce a nonlinear manipulation of elastic properties of the region of the object observed by the at least one HF pulse, wherein the means for using suppresses the deteriorating effect on the measurement or image signals of pulse reverberation noise in the HF receive signals.

55. The instrument according to claim 54, wherein the means for forming estimates the measurement or image signals that represent at least one of, linear scattering from the region of the object, nonlinear scattering from the region of the object, a local nonlinear propagation parameter of the region of the object, a local nonlinear scattering parameter of the region of the object, a quantitative, local nonlinear propagation parameter of the region of the object, and a quantitative, local nonlinear scattering parameter of the region of the object.

56. The instrument according to claim 54, where the HF transducer and receiver means includes a transducer array with a two-dimensional distribution of array elements, and where the means for forming processes at least one of element signals that are the received HF signals from array elements, and sub-aperture signals that are combinations of the received HF signals from sub-aperture groups of neighboring array elements, to provide new element or sub-aperture signals with substantial suppression of pulse reverberation noise, and the new element or sub-aperture signals are processed to provide estimates of corrections for wave front aberrations, and performs the wave front aberration corrections on the element or sub-aperture signals before they are summed to form receive beams, and corrections for the wave front aberrations on signals transmitted from the array elements.

57. The instrument according to claim 54, wherein the means for forming includes an instrument controller that selects a processing method for best performance under constraints that are preset or set by the operator.

58. The instrument according to claim 54, wherein the transmitting means transmits a broad beam and the HF transducer and receiver means arranges multiple parallel receive beams and processing to increase the image frame rate for 2D and 3D imaging.

59. The instrument according to claim 54, where the means for forming produces tomographic image reconstructions from the HF receive signals.

60. The instrument according to claim 59, wherein the means for forming bases the tomographic image reconstructions on estimates of signals that represent at least one of linear scattering from the region of the object, nonlinear scattering from the region of the object, a local nonlinear propagation parameter of the region of the object, a local nonlinear scattering parameter of the region of the object, a quantitative, local nonlinear propagation parameter of the region of the object, and a quantitative, local nonlinear scattering parameter of the region of the object.

61. A method for measurement or imaging of nonlinear acoustic scattering from a region of a region of an object, including:

a) transmitting at least two acoustic pulse complexes in beams toward the region of the object, each of the at least two pulse complexes includes at least one high frequency (HF) pulse and at least one low frequency (LF) pulse with the same or overlapping beam directions, wherein for each of the at least two pulse complexes, at least one of a frequency, an amplitude and a phase of the at least one LF pulse varies, and the amplitude of the at least one LF pulse of at least one of the at least two acoustic pulse complexes is nonzero;

b) receiving HF receive signals with a HF transducer that picks up at least one of acoustic waves produced by object scattering of the at least one HF pulse, and acoustic waves of the at least one HF pulse that have propagated through the object, and c) estimating differences in propagation delay between the HF pulses based on the HF receive signals, and delay correcting at least one of the HF receive signals from at least two of the HF pulses based on the estimated differences in propagation delay; and d) forming measurement or image signals that represent nonlinear scattering from the object with strong suppression of the linearly scattered signal from the object by combining, after the delay correcting, the HF receive signals and by using the at least one LF pulse to produce a nonlinear manipulation of elastic properties of the region of the object observed by the at least one HF pulse.

62. The method according to claim 61, wherein the differences in propagation delay are estimated from minimization of the power in the measurement or image signals that represent nonlinear scattering from the object.

63. The method according to claim 61, wherein at least one of the HF receive signals is additionally amplitude corrected, the amplitude and delay corrected HF receive signals are combined to provide the measurement or image signals that represent nonlinear scattering from the object.

64. The method according to claim 63, wherein the amplitude corrections are estimated from a minimization of the power in the measurement or image signals representing the nonlinear scattering from the object, under the constraint that the amplitude correction vector have a fixed norm.

65. The method according to claim 64, further comprising using visual observation of the power in the measurement or image signal as feedback for manual adjustment of at least one of the amplitude correction estimates and the estimates of differences in propagation delay at different depths along the beam to minimize the power in the measurement or image signal representing the nonlinear scattering from the object.

66. The method according to claim 61, wherein the signal representing nonlinear scattering is used to detect or image high compliance objects including at least one of fat and lipid particles in biological tissues and fluids, gas bubbles in biological tissues and fluids, fish and sea animals in water, soft regions in geologic structures, and content of at least one of oil and gas and water in porous rock.

67. The method according to claim 61, wherein the signal representing nonlinear scattering is used to detect or image low compliance objects including at least one of calcified objects in biological tissues and fluids, hard objects in soft tissue and fluids, mines in geologic structures, hard regions in geologic structures, and content of at least one of oil and gas and water in porous rock.

68. The method according to claim 61, wherein a $1^{st}$ nonlinear image parameter or signal, which is a local nonlinear forward propagation image parameter or signal representing local nonlinear propagation parameters of the region of the object, is formed from the differential along the fast time of the estimated nonlinear propagation delays.

69. The method according to claim 68, where a $1^{st}$ quantitative nonlinear image parameter or signal, which is a local nonlinear forward propagation image parameter or signal representing local nonlinear propagation parameters of the region of the object, is formed as a combination of the differential along the fast time of the estimated nonlinear propagation delays, and an estimate of the local pressure amplitude of the at least one LF pulse at the location of the at least one HF pulse.

70. The method according to claim 69, wherein a $2^{nd}$ quantitative nonlinear image parameter or signal, which is a nonlinearly scattered image parameter or signal representing local nonlinear scattering parameters of the region of the object, is formed by combining the local nonlinear scattering parameter or signal with an estimate of the local pressure amplitude of the LF pulse at the co-propagating HF pulse, and wherein at least one of the $1^{st}$ and $2^{nd}$ quantitative nonlinear image parameters or signals are used in a process of monitoring local object temperature during thermal treatment of the object.

71. The method according to claim 61, wherein the delay corrected received signals are combined to provide measurement or image signals that represent linear scattering from the object with the same depth variable gain and absorption attenuation as the signal that represents nonlinear scattering from the object, and a 2nd local nonlinear scattering parameter or signal is produced as the ratio of the local envelopes of the signals representing nonlinear and linear scattering from the object.

72. The method according to claim 71, wherein a $2^{nd}$ quantitative nonlinear image parameter or signal, which is a nonlinearly scattered image parameter or signal representing local nonlinear scattering parameters of the region of the object, is formed by combining the local nonlinear scattering parameter or signal with an estimate of the local pressure amplitude of the LF pulse at the co-propagating HF pulse.

73. The method according to claim 61, wherein the step of transmitting includes generating the at least one LF pulse and the at least one HF pulse with acoustic transducer arrays in which at least part of the radiation surfaces for the at least one LF pulse and the at least one HF pulse are different, so that the phase of the at least one LF pulse varies relative to the phase of the at least one HF pulse throughout the actual image range to produce a nonlinear propagation delay of the at least one HF pulse by the at least one LF pulse that has a non-monotone variation along the axis of the HF beam that limits the maximal nonlinear propagation delay, so that for low amplitudes of the at least one LF pulse in the range of approximately 50-100 kPa one can suppress the linearly scattered HF signal from the tissue and estimate a signal representing the received signal from nonlinear scattering of the HF pulses from micro gas bubbles with substantial suppression of linear scattering signal through a combination in the pulse number coordinate of the received HF signals from at least two pulses by approximating the estimated differences in propagation delays equal with zero.

74. The method according to claim 73, wherein the acoustic transducer arrays including an HF array for generating the at least one HF pulse, the HF array being a linear array, and an LF array for generating the at least one LF pulse, the LF array being one of one linear array mounted on one side of the HF array, and two linear arrays mounted on each side of the HF array.

75. The method according to claim 61, wherein the step of transmitting comprises transmitting broad HF and LF beams that cover multiple parallel HF receive beams to increase the image frame rate in 2D and 3D acoustic imaging, and wherein the step of forming comprises estimating measurement or image signals in parallel for the parallel receive beams.

76. The method according to claim 61, wherein the step of forming includes suppressing signal components from the at least one LF pulse in a received signal to extract the HF receive signal for further processing.

77. The method according to claim 61, where a $2^{nd}$ harmonic band of the HF receive signals is used to form the measurement or image signals.

78. The method according to claim 61, wherein the estimation of the total propagation delays or the nonlinear propagation delays is based on a $2^{nd}$ harmonic band of the HF receive signals.

79. The method according to claim 61, wherein the object is the neighborhood of an oil well.

80. The method according to claim 61, wherein the nonlinearly scattered signal is used to differentiate between rocks containing oil, gas, or water in the neighborhood of an oil well.

81. The method according to claim 61, wherein harmonic components of the at least one LF pulse in the received HF signal are suppressed by transmitting the at least one low frequency pulse without the at least one high frequency pulse and storing the received high band signal produced therefrom, and subtracting the stored high band signal from the received high band signals from transmitted pulse complexes that contain both the at least one LF pulse and the at least one HF pulse.

82. The method according to claim 61, further comprising estimating a local absorption coefficient in the object from the estimated nonlinear propagation delay, the depth gradient of the estimated nonlinear propagation delay, and an estimate of the high center frequency in the received signal and the depth gradient of the estimate of the high center frequency where the high frequency pulse for a substantial portion of the depth range propagates along a negative spatial gradient of the low frequency pulse.

83. The method according to claim 61, wherein the at least one HF pulse is at least in the near depth range placed close to a positive pressure peak of the at least one LF pulse in the transmitted pulse complex so that the maximal amplitude of the high frequency pulse can be increased within the limit of the maximally allowed Mechanical Index of the complex, for increased sensitivity with measurements both in the fundamental and harmonic bands of the at least one HF pulse.

84. The method according to claim 61, wherein the step of transmitting includes generating said pulse complexes with angular differences in beam directions, the angular differences affecting the propagation delay between said HF pulses, whereby the propagation delay can be minimized by adjusting the angular differences in beam directions.

85. An instrument for measurement or imaging of acoustic nonlinear scattering and/or propagation properties in a region of an object, comprising:

a) means for transmitting at least two acoustic pulse complexes in beams toward the region of the object, each of the acoustic pulse complexes comprising at least one high frequency (HF) pulse and at least one low frequency (LF) pulse with the same or overlapping beam directions;

b) HF transducer and receiver means for receiving HF receive signals from at least one of acoustic waves produced by object scattering of the at least one HF pulse and acoustic waves of the at least one HF pulse that have propagated through the object;

c) processing means for processing the HF receive signals from at least two of the transmitted pulse complexes, wherein for each of the at least two pulse complexes, at least one of a frequency, an amplitude and a phase of the at least one LF pulse varies, the amplitude of the at least one LF pulse of at least one of the at least two pulse complexes is nonzero; and d) the processing means further comprising means for estimating the nonlinear propagation delays between the HF received signals, delay correcting at least one of the HF received signals, and combining, after the delay correcting, the HF received signals from at least two pulse complexes to provide measurement or image signals that represent at least one of nonlinear scattering and propagation properties of the transmitted HF pulses from the object by using the at least one LF pulse to produce a nonlinear manipulation of elastic properties of the region of the object observed by the at least one HF pulse.

86. The instrument according to claim 85, wherein the processing means further comprises means for estimating one or more of measurement or image signals that represents, linear scattering from the region of the object, nonlinear scattering from the region of the object, a local nonlinear scattering parameter of the region of the object, a quantitative, local nonlinear scattering parameter of the region of the object, a local nonlinear propagation parameter of the region of the object, and a quantitative, local nonlinear propagation parameter of the region of the object.

87. The instrument according to claim 85, wherein the means for forming includes an instrument controller configured to select a processing method for best performance under constraints that are preset or set by the operator.

88. The instrument according to claim 85, wherein the means for forming comprises means for producing tomographic image reconstructions from the HF receive signals.

89. The instrument according to claim 88, wherein the means for forming bases the tomographic image reconstructions on estimates of signals that represent at least one of linear scattering from the region of the object, nonlinear scattering from the region of the object, a local nonlinear propagation parameter of the region of the object, a local nonlinear scattering parameter of the region of the object, a quantitative, local nonlinear propagation parameter of the region of the object, and a quantitative, local nonlinear scattering parameter of the region of the object.

90. A method for measurement or imaging of nonlinear acoustic propagation properties in a region of an object, including:

a) transmitting at least two acoustic pulse complexes in beams toward the region of the object, each of the at least two pulse complexes includes at least one high frequency (HF) pulse and at least one low frequency (LF) pulse with the same or overlapping beam directions, wherein for each of the at least two pulse complexes, at least one of a frequency, an amplitude and a phase of the at least one LF pulse varies, and the amplitude of the at least one LF pulse of at least one of the at least two pulse complexes is nonzero;

b) receiving HF receive signals with a HF transducer that at least picks up acoustic waves of the at least two HF pulses that have propagated through the object, and c) estimating differences in nonlinear propagation delay between the HF pulses based on the HF receive signals, and forming measurement or image signals that represent nonlinear propagation parameters in the region of the object at least based on said estimated propagation delays.

91. A method according to claim 90, where said measurement or image signals that represent nonlinear propagation parameters in the region of the object are formed in processes that include tomographic image reconstruction.

92. An instrument for measurement or imaging of acoustic nonlinear propagation properties in a region of an object, comprising:

a) means for transmitting acoustic pulse complexes, each of the acoustic pulse complexes comprising at least one high frequency (HF) pulse and at least one low frequency (LF) pulse with the same or overlapping beam directions;

b) HF transducer and receiver means for receiving HF receive signals at least from acoustic waves of the at least one HF pulse that have propagated through the object, and c) processing means for processing the HF receive signals from at least two of the transmitted pulse complexes, wherein for each of the at least two pulse complexes, at least one of a frequency, an amplitude and a phase of the at least one LF pulse varies where the amplitude of the at least one LF pulse of at least one of the at least two pulse complexes is nonzero; and d) the processing means further comprising means for estimating nonlinear propagation delays between the HF received signals, and forming measurement or image signals that represent nonlinear propagation parameters in the region of the object based on at least said estimated nonlinear propagation delays.

93. An instrument according to claim 92, where said processing means further comprises means for tomographic image reconstruction that presents measurement or image signals that represent nonlinear propagation parameters in the region of the object.

* * * * *